US008048995B2

(12) United States Patent
Fujiwara et al.

(10) Patent No.: US 8,048,995 B2
(45) Date of Patent: *Nov. 1, 2011

(54) HUMAN SKELETAL MUSCLE-SPECIFIC UBIQUITIN-CONJUGATING ENZYME

(75) Inventors: Tsutomu Fujiwara, Naruto (JP); Takeshi Watanabe, Itano-gun (JP); Masato Horie, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/689,917

(22) Filed: Jan. 19, 2010

(65) Prior Publication Data
US 2010/0160611 A1 Jun. 24, 2010

Related U.S. Application Data

(62) Division of application No. 11/593,525, filed on Nov. 7, 2006, now Pat. No. 7,674,889, which is a division of application No. 10/781,841, filed on Feb. 20, 2004, now abandoned, which is a division of application No. 10/342,276, filed on Jan. 15, 2003, now Pat. No. 7,420,048, which is a division of application No. 09/976,165, filed on Oct. 15, 2001, now Pat. No. 6,562,947, which is a division of application No. 09/565,538, filed on May 5, 2000, now Pat. No. 6,333,404, which is a division of application No. 09/273,565, filed on Mar. 22, 1999, now Pat. No. 6,166,190, which is a division of application No. 09/055,699, filed on Apr. 7, 1998, now Pat. No. 6,005,088, which is a division of application No. 08/820,170, filed on Mar. 19, 1997, now Pat. No. 5,831,058.

(30) Foreign Application Priority Data

Mar. 19, 1996 (JP) ................................. 1996-063410
Mar. 5, 1997 (JP) ................................. 1997-069163

(51) Int. Cl.
C07K 16/40 (2006.01)
C07K 16/00 (2006.01)
(52) U.S. Cl. ............. 530/388.26; 530/387.1; 530/388.1; 530/389.1
(58) Field of Classification Search .................. None
See application file for complete search history.

(56) References Cited

U.S. PATENT DOCUMENTS 5,863,779 A 1/1999 Lal
5,952,181 A 9/1999 Lal

FOREIGN PATENT DOCUMENTS

WO 96/36709 11/1996
WO 2004072100 A2 8/2004

OTHER PUBLICATIONS

Database EMBL (Online), 1996, Database Accession No. U4824.
Watanabe T K, et al, "Cloning and Characterization of Two Novel Human cDNAS (NELL1 and NELL2) Encoding Proteins with Six EGF-Like Repeats," Genomics, 1996, 38(3): 273-276.
Kuroda S, et al, "Biochemical Characterization and Expression Analysis of Neural Thrombospondin-1-like Proteins Nell1 and Nell2," Biochemical and Biophysical Research Communications, vol. 265, No. 1, 1999, pp. 79-86, Academic Press Inc., Orlando, FL.
Kuroda S, et al, "Involvement of Epidermal Growth Factor-Like Domain of Nell Proteins in the Novel Protein Interaction with Protein Kinase C," Biochemical and Biophysical Research Communications, vol. 265, No. 3, 1999, pp. 752-757, Academic Press Inc., Orlando, FL.
Okamoto K, et al, "Identification of NAD$^+$-Dependent Isocitrate Dehyrdogenase 3 γ-Like (IDH3GL) Gene and Its Genetic Polymorphisms," Gene, 2003, 323: 141-148.
Zhang X, et al, "Craniosynostosis in Transgenic Mice Overexpressing *Nell-1*," Journal of Clinical Investigation, 2002, 110(6): 861-870.
Zhang X, et al, "Overexpression of *NELL-1*, a Craniosynostosis-Associated Gene, Induces Apoptosis in Osteoblasts During Craniofacial Development," Journal of Bone and Mineral Research, 2003, 18(12): 2126-2134.
Luce M J, et al, "The Neuronal EGF-Related Genes *NELL1* and *NELL2* are Expressed in Hemapoietic Cells and Developmentally Regulated in the B Lineage," Gene, 1999, 231: 121-126.
Ting K, et al, "Human *NELL-1* Expressed in Unilateral Coronal Synostosis," Journal of Bone and Mineral Research, 1999, 14(1): 80-89.
Clone GEN-501D08, Moffett et al, *EMBO J.*, 12:339-347 (1993).
Clone Gene-080G1, Genbank Database Accession No. D49738 (1997).
Clone GEN-025F07, Genbank Database Accession Nos. Z4991, L34070, U19530 and X59720 (1994).
Clone GEN-076C09, Franzé et al, *Genomics*, 9(4):728-736 (1991), Abstract.
Clone GEN-331G07, Shibuya et al, *Nature*, 357(6380):700-702 (1992), Abstract.
Clone GEN-163D09, Genbank Database Accession No. Z49154 (1999).
Clone GEN-078D05, Simon et al, *Biochem. J.*, 297(Pt2):389-397 (1994), Abstract.
Clone GEN-432A12, Genschik et al, *Mol. Gen. Genet.*, 244(5):548-556 (1994), Abstract.
Clone GEN-092E10, Genbank Database Accession No. U19878 (1995).
Clone GEN-428B12, Sun et al, *Mol. Cell Biol.*, 15(1):564-565 (1995), Abstract.

(Continued)

Primary Examiner — Sharon Wen
(74) Attorney, Agent, or Firm — Sughrue Mion, PLLC

(57) ABSTRACT

The present invention provides novel human genes, for example a novel human gene comprising a nucleotide sequence coding for the amino acid sequence shown under SEQ ID NO:1. The use of the genes makes it possible to detect the expression of the same in various tissues, analyze their structures and functions, and produce the human proteins encoded by the genes by the technology of genetic engineering. Through these, it becomes possible to analyze the corresponding expression products, elucidate the pathology of diseases associated with the genes, for example hereditary diseases and cancer, and diagnose and treat such diseases.

2 Claims, 2 Drawing Sheets

OTHER PUBLICATIONS

Clone GEN-073E05, Spritz et al, *Genomics*, 22(2):425-430 (1994), Abstract.

Clone GEN-093E05, Matshuhashi et al, *Dev. Dyn.*, 203(2):212-222 (1995), Abstract.

Clone GEN-077A09, Hoshino et al, *EMBO J.*, 8(12):3807-3814 (1989), Abstract.

Takahashi et al, *Hum. Genet.*, 86:14-16 (1990).

Cherif et al, *Proc. Natl. Sci*, USA, 87:6634-6638 (1990).

Fujiwara et al, *DNA Research*, 2:107-111 (1995).

Takashi et al, *Human Genet.*, 88:119-121 (1991).

Peterson et al, *J. Biol. Chem.*, 271(47):29903-29908 (1996).

Eib et al, "A novel Transmembrane Protein Containing Two Follistatin Modules and an EGF Domain", Database Accession No. U19878.1, Abstract XP002289426 (Apr. 2, 1995).

Rupp et al, "Structure and Chromosomal Localization of the Mammalian Agrin Gene", J. of Neuroscience, 1992, 12(9):3535-3544.

Uchida et al, "A Novel Epidermal Growth Factor-like Molecule Containing Two Follistatin Modules Stimulates Tyrosine Phosphorylation of erbB-4 in MKN28 Gastric Cancer Cells", Biochemical and Biophysical Res. Comm., 1999, 266: 593-602.

Glynne-Jones et al, "TENB2, A Proteoglycan Identified in Prostate Cancer that is Associated with Disease Progression and Androgen Independence", Int'l. J. of Cancer, 2001, 94(2): 178-184.

Liang et al, "The Gene for a Novel Transmembrane Protein Containing Epidermal Growth Factor and Follistain Domains Is Frequently Hypermethylated in Human Tumor Cells", *Cancer Res.*, 2000, 60(17): 4907-4912.

Attwood, T, Science, "The Babel of Bioinformatics", 2000, 290(5491): 471-473.

Gerhold et al, "It's the genes! EST access to human genome content", BioEssays, 1996, 18(12): 973-981.

Russell et al, "Structural Features can be Unconserved in Proteins with Similar Folds", Journal of Molecular Biology, 1994, 244: 332-350.

Wells et al, "The chemokine information source: identification and characterization of novel chemokines using the WorldWideWeb and Expressed Sequence Tag Databases", Journal of Leukocyte Biology, 1997, 61(5): 545-550.

Guo et al, "Protein tolerance to random amino acid change", PNAS, USA, 2004, 101(25): 9205-9210.

Aihara Koutoku et al: "A neuron-specific EGF family protein, NELL2, promotes survival of neurons through mitogen-activated protein kinases."Brain Research Molecular Brain Research Aug. 19, 2003 LNKD-PUBMED:12941464, vol. 116, No. 1-2, (Aug. 19, 2003), pp. 86-93, ISSN: 0169-328X, Abstract.

Maeda K et al: "Brain specific human genes, NELL1 and NELL2, are predominantly expressed in neuroblastoma and other embryonal neuroepithelial tumors."Neurologia Medico-Chirurgica Dec. 2001 LNKD-PUBMED:11803583, vol. 41, No. 12, Dec. 2001, pp. 582-588: DIS, ISSN: 0470-8105, Abstract.

Matsuhashi S.; et al, 1995, "New gene, nel, encoding a M(r) 93 K protein with EGF-like repeats is strongly expressed in neural tissues of early stage chick embryos.", Developmental dynamics, Jun. 1995, vol. 203, NR-2, PG-212-222, XP0009057037.

Office Action dated Feb. 16, 2011 issued in corresponding European Patent Application No. 07014998.4.

European Search Report issued in application No. 10182760.8-1212 dated Dec. 8, 2010.

Database EMBL,"Rattus norbegicus protein kinase C-binding protein NELL1 mRNA, complete cds," Feb. 23, 1996, Accession No. EMBL U48246.

Lichter et al. Proc. Natl. Acad. Sci., USA 87: 6634-6638 (1990).

Lucentini, The Scientist, 2004, 18:20.

Watanabe et al.: "Molecular cloning of UBE2G, encoding a human skeletal muscle-specific ubiquitin-conjugating enzyme homologous to UBC7 of C. elegans," Cytogenet Cell Genet 1996;74:146-148.

Japanese Office Action issued in JP 2004-041767 issued May 16, 2007.

Wilson R. et al.: "2.2 Mb of contiguous nucleotide sequence from chromosome III of C. elegans", Nature 368 (6466), 32-38 (1994).

Wilson R. et al., "Probable Ubiquitin-Conjugating Enzyme E2-19 KD (Ubiquitin-Protein Ligase) (Ubiquitin Carrier Protein)" DATABASE GenBank accession No. P34477, Jun. 1994.

Comparison showing the revision history of Genbank accession No. P34477: the top row is the present information of the "LIVE" P34477 dated Mar. 8, 2011 and the bottom row is the information of P34477 at the point of Mar. 25, 1994.

Comparison showing changes made to the Genbank accession No. P34477 record from the present information with respect to the information at the point of Jun. 1, 1994 (marked in blue, updated on Mar. 25, 1994 10:46 PM) cited from the Database Genbank accession No. P34477.

Database accession No. AA113903, Nov. 30, 1996, EBI accession No. EM_EST:AA113903.

Database accession No. D78514, Dec. 21, 1996, EBI accession No. EM_HUM:D78514.

Database accession No. P34477, Feb. 1, 1994, EBI accession No. UNIPROT: P34477.

European Search Report dated Jun. 8, 2011, for European Patent Application No. 10185775.3.

Hillier, Ladeana, et al., "Generation and Analysis of 280,000 Human Expressed Sequence Tags", Genome Research, (1996), vol. 6, pp. 807-828.

Watanabe, T. K. et al., "Molecular cloning of UBE2G, encoding a human skeletal muscle-specific ubiquitin-conjugating enzyme homologous to UBC7 of C. elegans", Cytogenetics and Cell Genetics, (1996), 74: pp. 146-148.

Wilson, R., et al., "2.2 Mb of contiguous nucleotide sequence from chromosome III of C. elegans", Nature, (1994), vol. 368, pp. 32-38.

1 2

SEQUENCE LISTING

<160> NUMBER OF SEQ ID NOS: 96

<210> SEQ ID NO 1
<211> LENGTH: 122
<212> TYPE: PRT
<213> ORGANISM: Homo sapiens

<400> SEQUENCE: 1

```
Met Glu Leu Gly Glu Asp Gly Ser Val Tyr Lys Ser Ile Leu Val Thr
  1               5                  10                  15

Ser Gln Asp Lys Ala Pro Ser Val Ile Ser Arg Val Leu Lys Lys Asn
             20                  25                  30

Asn Arg Asp Ser Ala Val Ala Ser Glu Tyr Glu Leu Val Gln Leu Leu
         35                  40                  45

Pro Gly Glu Arg Glu Leu Thr Ile Pro Ala Ser Ala Asn Val Phe Tyr
     50                  55                  60

Pro Met Asp Gly Ala Ser His Asp Phe Leu Leu Arg Gln Arg Arg Arg
 65                  70                  75                  80

Ser Ser Thr Ala Thr Pro Gly Val Thr Ser Gly Pro Ser Ala Ser Gly
                 85                  90                  95

Thr Pro Pro Ser Glu Gly Gly Gly Ser Phe Pro Arg Ile Lys Ala
            100                 105                 110

Thr Gly Arg Lys Ile Ala Arg Ala Leu Phe
        115                 120
```

<210> SEQ ID NO 2
<211> LENGTH: 366
<212> TYPE: DNA
<213> ORGANISM: Homo sapiens

<400> SEQUENCE: 2

```
atggagttgg gggaagatgg cagtgtctat aagagcattt tggtgacaag ccaggacaag      60
gctccaagtg tcatcagtcg tgtccttaag aaaaacaatc gtgactctgc agtggcttca     120
gagtatgagc tggtacagct gctaccaggg gagcgagagc tgactatccc agcctcggct     180
aatgtattct acccccatgga tggagcttca cacgatttcc tcctgcggca gcggcgaagg     240
tcctctactg ctacacctgg cgtcaccagt ggcccgtctg cctcaggaac tcctccgagt     300
gagggaggag ggggctcctt tccaggatc aaggccacag ggaggaagat tgcacgggca      360
``` ctgttc                                                                    366

<210> SEQ ID NO 3
<211> LENGTH: 842
<212> TYPE: DNA
<213> ORGANISM: Homo sapiens
<220> FEATURE:
<221> NAME/KEY: CDS
<222> LOCATION: (28)..(393)

<400> SEQUENCE: 3

```
cccacgagcc gtatcatccg agtccag atg gag ttg ggg gaa gat ggc agt gtc      54
                        Met Glu Leu Gly Glu Asp Gly Ser Val
                         1               5 tat aag agc att ttg gtg aca agc cag gac aag gct cca agt gtc atc       102
Tyr Lys Ser Ile Leu Val Thr Ser Gln Asp Lys Ala Pro Ser Val Ile
 10              15                  20                  25 agt cgt gtc ctt aag aaa aac aat cgt gac tct gca gtg gct tca gag       150
Ser Arg Val Leu Lys Lys Asn Asn Arg Asp Ser Ala Val Ala Ser Glu
             30                  35                  40 tat gag ctg gta cag ctg cta cca ggg gag cga gag ctg act atc cca       198
Tyr Glu Leu Val Gln Leu Leu Pro Gly Glu Arg Glu Leu Thr Ile Pro
         45                  50                  55 gcc tcg gct aat gta ttc tac ccc atg gat gga gct tca cac gat ttc       246
Ala Ser Ala Asn Val Phe Tyr Pro Met Asp Gly Ala Ser His Asp Phe
     60                  65                  70 ctc ctg cgg cag cgg cga agg tcc tct act gct aca cct ggc gtc acc       294
Leu Leu Arg Gln Arg Arg Arg Ser Ser Thr Ala Thr Pro Gly Val Thr
 75                  80                  85 agt ggc ccg tct gcc tca gga act cct ccg agt gag gga gga ggg ggc       342
Ser Gly Pro Ser Ala Ser Gly Thr Pro Pro Ser Glu Gly Gly Gly Gly
             90                  95                 100             105 tcc ttt ccc agg atc aag gcc aca ggg agg aag att gca cgg gca ctg       390
Ser Phe Pro Arg Ile Lys Ala Thr Gly Arg Lys Ile Ala Arg Ala Leu
                    110                 115                 120 ttc tgaggaggaa gccccttttt ttacagaagt catggtgttc ataccagatg            443
Phe tgggtagcca tcctgaatgg tggcaattat atcacattga acagaaatt cagaaaggga      503 gccagccacc ctggggcagt gaagtgccac tggtttacca gacagctgag aaatccagcc     563
ctgtcggaac tggtgtctta taccaagtt ggatacctgt gtatagcttg ccaccttcca      623
tgagtgcagc acacaggtag tgctggaaaa acgcatcagt ttctgattct tggccatatc     683
ctaacatgca agggccaagc aaaggcttca aggctctgag ccccagggca gaggggaatg     743
gcaaaatgta ggtcctggca ggagctcttc ttcccactct ggggggtttct atcactgtga   803 caacactaag ataataaacc aaaacactac ctgaattct                             842
```

<210> SEQ ID NO 4
<211> LENGTH: 193
<212> TYPE: PRT
<213> ORGANISM: Homo sapiens

<400> SEQUENCE: 4

```
Met Glu Leu Glu Leu Tyr Gly Val Asp Asp Lys Phe Tyr Ser Lys Leu
 1               5                  10                  15

Asp Gln Glu Asp Ala Leu Leu Gly Ser Tyr Pro Val Asp Asp Gly Cys
             20                  25                  30

Arg Ile His Val Ile Asp His Ser Gly Ala Arg Leu Gly Glu Tyr Glu
         35                  40                  45
```

```
Asp Val Ser Arg Val Glu Lys Tyr Thr Ile Ser Gln Glu Ala Tyr Asp
    50                  55                  60

Gln Arg Gln Asp Thr Val Arg Ser Phe Leu Lys Arg Ser Lys Leu Gly
65                  70                  75                  80

Arg Tyr Asn Glu Glu Glu Arg Ala Gln Gln Glu Ala Glu Ala Ala Gln
                85                  90                  95

Arg Leu Ala Glu Glu Lys Ala Gln Ala Ser Ser Ile Pro Val Gly Ser
                100                 105                 110

Arg Cys Glu Val Arg Ala Ala Gly Gln Ser Pro Arg Gly Thr Val
                115                 120                 125

Met Tyr Val Gly Leu Thr Asp Phe Lys Pro Gly Tyr Trp Ile Gly Val
    130                 135                 140

Arg Tyr Asp Glu Pro Leu Gly Lys Asn Asp Gly Ser Val Asn Gly Lys
145                 150                 155                 160

Arg Tyr Phe Glu Cys Gln Ala Lys Tyr Gly Ala Phe Val Lys Pro Ala
                165                 170                 175

Val Val Thr Val Gly Asp Phe Pro Glu Glu Asp Tyr Gly Leu Asp Glu
                180                 185                 190

Ile

<210> SEQ ID NO 5
<211> LENGTH: 579
<212> TYPE: DNA
<213> ORGANISM: Homo sapiens

<400> SEQUENCE: 5
atggaactgg agctgtatgg agttgacgac aagttctaca gcaagctgga tcaagaggat      60
gcgctcctgg ctcctaccc tgtagatgac ggctgccgca tccacgtcat tgaccacagt     120
ggcgcccgcc ttggtgagta tgaggacgtg tcccgggtgg agaagtacac gatctcacaa     180
gaagcctacg accagaggca agacacggtc cgctctttcc tgaagcgcag caagctcggc     240
cggtacaacg aggaggagcg ggctcagcag gaggccgagg ccgcccagcg cctggccgag     300
gagaaggccc aggccagctc catccccgtg ggcagccgct gtgaggtgcg gcggcggga     360 caatcccctc gccggggcac cgtcatgtat gtaggtctca cagatttcaa gcctggctac     420
tggattggtg tccgctatga tgagccactg gggaaaaatg atggcagtgt gaatgggaaa     480
cgctacttcg aatgccaggc caagtatggc gcctttgtca agccagcagt cgtgacggtg     540
ggggacttcc cggaggagga ctacgggttg acgagata                             579

<210> SEQ ID NO 6
<211> LENGTH: 1015
<212> TYPE: DNA
<213> ORGANISM: Homo sapiens
<220> FEATURE:
<221> NAME/KEY: CDS
<222> LOCATION: (274)..(852)

<400> SEQUENCE: 6
tgattggtca ggcacggagc aggaggcggg ctgatagccc agcagcagca gcggcggcgg      60
cggctgcgga gcgggtgtga ggcggctgga ccgcgctgca ggcatccgcg ggcgcggcaa     120
gatggaggtg acggggtgt cggcaccacg gtgaccgttt tcatcagcag ctccctcagc     180
accttccgct ccgagaagcg atacagccgc agcctcacca tcgctgagtt caagtgtaaa     240
ctggagttgc tggtgggcag ccctgcttcc tgc atg gaa ctg gag ctg tat gga    294
                                    Met Glu Leu Glu Leu Tyr Gly
                                    1               5
```

| | | | | | | | | | | | | | | | |
|---|---|---|---|---|---|---|---|---|---|---|---|---|---|---|---|
| gtt | gac | gac | aag | ttc | tac | agc | aag | ctg | gat | caa | gag | gat | gcg | ctc | ctg | 342 |
| Val | Asp | Asp | Lys | Phe | Tyr | Ser | Lys | Leu | Asp | Gln | Glu | Asp | Ala | Leu | Leu | |
| | | 10 | | | | 15 | | | | 20 | | | | | | |

```
gtt gac gac aag ttc tac agc aag ctg gat caa gag gat gcg ctc ctg    342
Val Asp Asp Lys Phe Tyr Ser Lys Leu Asp Gln Glu Asp Ala Leu Leu
        10                  15                  20 ggc tcc tac cct gta gat gac ggc tgc cgc atc cac gtc att gac cac    390
Gly Ser Tyr Pro Val Asp Asp Gly Cys Arg Ile His Val Ile Asp His
 25                  30                  35 agt ggc gcc cgc ctt ggt gag tat gag gac gtg tcc cgg gtg gag aag    438
Ser Gly Ala Arg Leu Gly Glu Tyr Glu Asp Val Ser Arg Val Glu Lys
 40                  45                  50                  55 tac acg atc tca caa gaa gcc tac gac cag agg caa gac acg gtc cgc    486
Tyr Thr Ile Ser Gln Glu Ala Tyr Asp Gln Arg Gln Asp Thr Val Arg
             60                  65                  70 tct ttc ctg aag cgc agc aag ctc ggc cgg tac aac gag gag gag cgg    534
Ser Phe Leu Lys Arg Ser Lys Leu Gly Arg Tyr Asn Glu Glu Glu Arg
             75                  80                  85 gct cag cag gag gcc gag gcc gcc cag cgc ctg gcc gag gag aag gcc    582
Ala Gln Gln Glu Ala Glu Ala Ala Gln Arg Leu Ala Glu Glu Lys Ala
             90                  95                 100 cag gcc agc tcc atc ccc gtg ggc agc cgc tgt gag gtg cgg gcg gcg    630
Gln Ala Ser Ser Ile Pro Val Gly Ser Arg Cys Glu Val Arg Ala Ala
        105                 110                 115 gga caa tcc cct cgc cgg ggc acc gtc atg tat gta ggt ctc aca gat    678
Gly Gln Ser Pro Arg Arg Gly Thr Val Met Tyr Val Gly Leu Thr Asp
120                 125                 130                 135 ttc aag cct ggc tac tgg att ggt gtc cgc tat gat gag cca ctg ggg    726
Phe Lys Pro Gly Tyr Trp Ile Gly Val Arg Tyr Asp Glu Pro Leu Gly
             140                 145                 150 aaa aat gat ggc agt gtg aat ggg aaa cgc tac ttc gaa tgc cag gcc    774
Lys Asn Asp Gly Ser Val Asn Gly Lys Arg Tyr Phe Glu Cys Gln Ala
             155                 160                 165 aag tat ggc gcc ttt gtc aag cca gca gtc gtg acg gtg ggg gac ttc    822
Lys Tyr Gly Ala Phe Val Lys Pro Ala Val Val Thr Val Gly Asp Phe
             170                 175                 180 ccg gag gag gac tac ggg ttg gac gag ata tgacacctaa ggaattcccc      872
Pro Glu Glu Asp Tyr Gly Leu Asp Glu Ile
        185                 190 tgcttcagct cctagctcag ccactgactg ccccctcctgt gtgtgcccat ggccttttc    932 tcctgacccc attttaattt tattcatttt ttcctttgcc attgatttt gagactcatg    992 cattaaattc actagaaacc cag                                          1015

<210> SEQ ID NO 7
<211> LENGTH: 128
<212> TYPE: PRT
<213> ORGANISM: Homo sapiens

<400> SEQUENCE: 7

Met Thr Glu Ala Asp Val Asn Pro Lys Ala Tyr Pro Leu Ala Asp Ala
 1               5                  10                  15

His Leu Thr Lys Lys Leu Leu Asp Leu Val Gln Gln Ser Cys Asn Tyr
             20                  25                  30

Lys Gln Leu Arg Lys Gly Ala Asn Glu Ala Thr Lys Thr Leu Asn Arg
         35                  40                  45

Gly Ile Ser Glu Phe Ile Val Met Ala Ala Asp Ala Glu Pro Leu Glu
     50                  55                  60

Ile Ile Leu His Leu Pro Leu Leu Cys Glu Asp Lys Asn Val Pro Tyr
 65                  70                  75                  80

Val Phe Val Arg Ser Lys Gln Ala Leu Gly Arg Ala Cys Gly Val Ser
                 85                  90                  95
```

```
Arg Pro Val Ile Ala Cys Ser Val Thr Ile Lys Glu Gly Ser Gln Leu
            100                 105                 110

Lys Gln Gln Ile Gln Ser Ile Gln Gln Ser Ile Glu Arg Leu Leu Val
            115                 120                 125

<210> SEQ ID NO 8
<211> LENGTH: 384
<212> TYPE: DNA
<213> ORGANISM: Homo sapiens

<400> SEQUENCE: 8
atgactgagg ctgatgtgaa tccaaaggcc tatccccttg ccgatgccca cctcaccaag      60
aagctactgg acctcgttca gcagtcatgt aactataagc agcttcggaa aggagccaat     120
gaggccacca aaaccctcaa caggggcatc tctgagttca tcgtgatggc tgcagacgcc     180
gagccactgg agatcattct gcacctgccg ctgctgtgtg aagacaagaa tgtgccctac     240
gtgtttgtgc gctccaagca ggccctgggg agagcctgtg ggtctccag  gcctgtcatc     300 gcctgttctg tcaccatcaa agaaggctcg cagctgaaaa cagcagatcc atccattcag     360
cagtccattg aaaggctctt agtc                                           384

<210> SEQ ID NO 9
<211> LENGTH: 1493
<212> TYPE: DNA
<213> ORGANISM: Homo sapiens
<220> FEATURE:
<221> NAME/KEY: CDS
<222> LOCATION: (95)..(478)

<400> SEQUENCE: 9
atccgtgtcc ttgcggtgct gggcagcaga ccgtccaaac cgacacgcgt ggtatcctcg      60
cggtgtccgg caagagacta ccaagacaga cgct atg act gag gct gat gtg aat    115
                                    Met Thr Glu Ala Asp Val Asn
                                      1               5 cca aag gcc tat ccc ctt gcc gat gcc cac ctc acc aag aag cta ctg      163
Pro Lys Ala Tyr Pro Leu Ala Asp Ala His Leu Thr Lys Lys Leu Leu
        10                  15                  20 gac ctc gtt cag cag tca tgt aac tat aag cag ctt cgg aaa gga gcc      211
Asp Leu Val Gln Gln Ser Cys Asn Tyr Lys Gln Leu Arg Lys Gly Ala
    25                  30                  35 aat gag gcc acc aaa acc ctc aac agg ggc atc tct gag ttc atc gtg      259
Asn Glu Ala Thr Lys Thr Leu Asn Arg Gly Ile Ser Glu Phe Ile Val
40                  45                  50                  55 atg gct gca gac gcc gag cca ctg gag atc att ctg cac ctg ccg ctg      307
Met Ala Ala Asp Ala Glu Pro Leu Glu Ile Ile Leu His Leu Pro Leu
                60                  65                  70 ctg tgt gaa gac aag aat gtg ccc tac gtg ttt gtg cgc tcc aag cag      355
Leu Cys Glu Asp Lys Asn Val Pro Tyr Val Phe Val Arg Ser Lys Gln
            75                  80                  85 gcc ctg ggg aga gcc tgt ggg gtc tcc agg cct gtc atc gcc tgt tct      403
Ala Leu Gly Arg Ala Cys Gly Val Ser Arg Pro Val Ile Ala Cys Ser
        90                  95                 100 gtc acc atc aaa gaa ggc tcg cag ctg aaa cag cag atc caa tcc att      451
Val Thr Ile Lys Glu Gly Ser Gln Leu Lys Gln Gln Ile Gln Ser Ile
    105                 110                 115 cag cag tcc att gaa agg ctc tta gtc taaacctgtg gcctctgcca             498
Gln Gln Ser Ile Glu Arg Leu Leu Val
120                 125 cgtgctccct gccagcttcc ccctgaggt tgtgtatcat attatctgtg ttagcatgta     558
gtattttcag ctactctcta ttgttataaa atgtagtact aaatctggtt tctggatttt    618
```

```
tgtgttgttt tgttctgtt ttacagggtt gctatccccc ttcctttcct ccctccctct    678
gccatccttc atccttttat cctccctttt tggaacaagt gttcagagca gacagaagca    738
gggtggtggc accgttgaaa ggcagaaaga gccaggagaa agctgatgga gccaggacag    798
agatctggtt ccagctttca gccactagct tcctgttgtg tgcggggtgt ggtggaatta    858
aacagcattc attgtgtgtc cctgtgcctg gcacacagaa tcattcatac gtgttcaagt    918
gatcaagggg tttcatttgc tcttgggggga ttaggtatca tttggggagg aagcatgtgt    978
tctgtgaggt tgttcggcta tgtccaagtg tcgtttacta atgtacccct gctgtttgct   1038
tttggtaatg tgatgttgat gttctccccc tacccacaac catgcccttg agggtagcag   1098
ggcagcagca taccaaagag atgtgctgca ggactccgga ggcagcctgg gtgggtgagc   1158
catggggcag ttgacctggg tcttgaaaga gtcgggagtg acaagctcag agagcatgaa   1218
ctgatgctgg catgaaggat tccaggaaga tcatggagac ctggctggta gctgtaacag   1278
agatggtgga gtccaaggaa acagcctgtc tctggtgaat gggacttctct ttggtggaca   1338
cttggcacca gctctgagag ccccttcccct gtgtcctgcc accatgtggg tcagatgtac   1398
tctctgtcac atgaggagag tgctagttca tgtgttctcc attcttgtga gcatcctaat   1458
aaatctgttc cattttgaaa aaaaaaaaaa aaaaa                              1493
```

<210> SEQ ID NO 10
<211> LENGTH: 711
<212> TYPE: PRT
<213> ORGANISM: Homo sapiens
<400> SEQUENCE: 10

```
Met Pro Ala Asp Val Asn Leu Ser Gln Lys Pro Gln Val Leu Gly Pro
 1               5                  10                  15

Glu Lys Gln Asp Gly Ser Cys Glu Ala Ser Val Ser Phe Glu Asp Val
                20                  25                  30

Thr Val Asp Phe Ser Arg Glu Glu Trp Gln Gln Leu Asp Pro Ala Gln
            35                  40                  45

Arg Cys Leu Tyr Arg Asp Val Met Leu Glu Leu Tyr Ser His Leu Phe
        50                  55                  60

Ala Val Gly Tyr His Ile Pro Asn Pro Glu Val Ile Phe Arg Met Leu
    65                  70                  75                  80

Lys Glu Lys Glu Pro Arg Val Glu Glu Ala Glu Val Ser His Gln Arg
                85                  90                  95

Cys Gln Glu Arg Glu Phe Gly Leu Glu Ile Pro Gln Lys Glu Ile Ser
               100                 105                 110

Lys Lys Ala Ser Phe Gln Lys Asp Met Val Gly Glu Phe Thr Arg Asp
           115                 120                 125

Gly Ser Trp Cys Ser Ile Leu Glu Glu Leu Arg Leu Asp Ala Asp Arg
       130                 135                 140

Thr Lys Lys Asp Glu Gln Asn Gln Ile Gln Pro Met Ser His Ser Ala
145                 150                 155                 160

Phe Phe Asn Lys Lys Thr Leu Asn Thr Glu Ser Asn Cys Glu Tyr Lys
               165                 170                 175

Asp Pro Gly Lys Met Ile Arg Thr Arg Pro His Leu Ala Ser Ser Gln
           180                 185                 190

Lys Gln Pro Gln Lys Cys Cys Leu Phe Thr Glu Ser Leu Lys Leu Asn
       195                 200                 205

Leu Glu Val Asn Gly Gln Asn Glu Ser Asn Asp Thr Glu Gln Leu Asp
   210                 215                 220
```

```
Asp Val Val Gly Ser Gly Gln Leu Phe Ser His Ser Ser Asp Ala
225                 230                 235                 240

Cys Ser Lys Asn Ile His Thr Gly Glu Thr Phe Cys Lys Gly Asn Gln
            245                 250                 255

Cys Arg Lys Val Cys Gly His Lys Gln Ser Leu Lys Gln His Gln Ile
                260                 265                 270

His Thr Gln Lys Lys Pro Asp Gly Cys Ser Glu Cys Gly Lys Ser Phe
        275                 280                 285

Thr Gln Lys Ser His Leu Phe Ala Gln Gln Arg Ile His Ser Val Gly
    290                 295                 300

Asn Leu His Glu Cys Gly Lys Cys Gly Lys Ala Phe Met Pro Gln Leu
305                 310                 315                 320

Lys Leu Ser Val Tyr Leu Thr Asp His Thr Gly Asp Ile Pro Cys Ile
                325                 330                 335

Cys Lys Glu Cys Gly Lys Val Phe Ile Gln Arg Ser Glu Leu Leu Thr
                340                 345                 350

His Gln Lys Thr His Thr Arg Lys Lys Pro Tyr Lys Cys His Asp Cys
        355                 360                 365

Gly Lys Ala Phe Phe Gln Met Leu Ser Leu Phe Arg His Gln Arg Thr
    370                 375                 380

His Ser Arg Glu Lys Leu Tyr Glu Cys Ser Glu Cys Gly Lys Gly Phe
385                 390                 395                 400

Ser Gln Asn Ser Thr Leu Ile Ile His Gln Lys Ile His Thr Gly Glu
                405                 410                 415

Arg Gln Tyr Ala Cys Ser Glu Cys Gly Lys Ala Phe Thr Gln Lys Ser
                420                 425                 430

Thr Leu Ser Leu His Gln Arg Ile His Ser Gly Gln Lys Ser Tyr Val
            435                 440                 445

Cys Ile Glu Cys Gly Gln Ala Phe Ile Gln Lys Ala His Leu Ile Val
            450                 455                 460

His Gln Arg Ser His Thr Gly Glu Lys Pro Tyr Gln Cys His Asn Cys
465                 470                 475                 480

Gly Lys Ser Phe Ile Ser Lys Ser Gln Leu Asp Ile His Arg Ile
                485                 490                 495

His Thr Gly Glu Lys Pro Tyr Cys Ser Asp Cys Gly Lys Thr Phe
            500                 505                 510

Thr Gln Lys Ser His Leu Asn Ile His Gln Lys Ile His Thr Gly Glu
        515                 520                 525

Arg His His Val Cys Ser Glu Cys Gly Lys Ala Phe Asn Gln Lys Ser
        530                 535                 540

Ile Leu Ser Met His Gln Arg Ile His Thr Gly Glu Lys Pro Tyr Lys
545                 550                 555                 560

Cys Ser Glu Cys Gly Lys Ala Phe Thr Ser Lys Ser Gln Phe Lys Glu
                565                 570                 575

His Gln Arg Ile His Thr Gly Glu Lys Pro Tyr Val Cys Thr Glu Cys
            580                 585                 590

Gly Lys Ala Phe Asn Gly Arg Ser Asn Phe His Lys His Gln Ile Thr
            595                 600                 605

His Thr Arg Glu Arg Pro Phe Val Cys Tyr Lys Cys Gly Lys Ala Phe
        610                 615                 620

Val Gln Lys Ser Glu Leu Ile Thr His Gln Arg Thr His Met Gly Glu
625                 630                 635                 640

Lys Pro Tyr Glu Cys Leu Asp Cys Gly Lys Ser Phe Ser Lys Lys Pro
```

| | | 645 | | | 650 | | | | 655 | | |
|---|---|---|---|---|---|---|---|---|---|---|---|
Gln Leu Lys Val His Gln Arg Ile His Thr Gly Glu Arg Pro Tyr Val
            660                 665                 670

Cys Ser Glu Cys Gly Lys Ala Phe Asn Asn Arg Ser Asn Phe Asn Lys
            675                 680                 685

His Gln Thr Thr His Thr Arg Asp Lys Ser Tyr Lys Cys Ser Tyr Ser
            690                 695                 700

Val Lys Gly Phe Thr Lys Gln
705                 710

<210> SEQ ID NO 11
<211> LENGTH: 2133
<212> TYPE: DNA
<213> ORGANISM: Homo sapiens

<400> SEQUENCE: 11

```
atgcctgctg atgtgaattt atcccagaag cctcaggtcc tgggtccaga gaagcaggat      60
ggatcttgcg aggcatcagt gtcatttgag acgtgaccg tggacttcag cagggaggag     120
tggcagcaac tggaccctgc ccagagatgc ctgtaccggg atgtgatgct ggagctctat    180
agccatctct tcgcagtggg gtatcacatt cccaacccag aggtcatctt cagaatgcta    240
aaagaaaagg agccgcgtgt ggaggaggct gaagtctcac atcagaggtg tcaagaaagg    300
gagtttgggc ttgaaatccc acaaaaggag atttctaaga aagcttcatt tcaaaaggat    360
atggtaggtg agttcacaag agatggttca tgtgttcca ttttagaaga actgaggctg    420
gatgctgacc gcacaaagaa agatgagcaa atcaaattc aacccatgag tcacagtgct    480
ttcttcaaca gaaaacatt gaacacagaa agcaattgtg aatataagga ccctgggaaa    540
atgattcgca cgaggcccca ccttgcttct tcacagaaac aacctcagaa atgttgctta    600
tttacagaaa gtttgaagct gaacctagaa gtgaacggtc agaatgaaag caatgacaca    660
gaacagcttg atgacgttgt tgggtctggt cagctattca gccatagctc ttctgatgcc    720
tgcagcaaga atattcatac aggagagaca ttttgcaaag gtaaccagtg tagaaaagtc    780
tgtggccata acagtcact caagcaacat caaattcata ctcagaagaa accagatgga    840
tgttctgaat gtgggggag cttcacccag aagtcacacc tctttgccca acagagaatt    900
catagtgtag aaaacctcca tgaatgtggc aaatgtggaa aagccttcat gccacaacta    960
aaactcagtg tatatctgac agatcataca ggtgatatac cctgtatatg caaggaatgt   1020
gggaaggtct ttattcagag atcagaattg cttacgcacc agaaaacaca cactagaaag   1080
aagcccctata atgccatga ctgtggaaaa gccttttcc agatgttatc tctcttcaga   1140
catcagagaa ctcacagtag agaaaaactc tatgaatgca gtgaatgtgg caaaggcttc   1200
tcccaaaact caaccctcat tatacatcag aaaattcata ctggtgagag acagtatgca   1260
tgcagtgaat gtgggaaagc ctttacccag aagtcaacac tcagcttgca ccagagaatc   1320
cactcagggc agaagtccta tgtgtgtatc gaatgcgggc aggccttcat ccagaaggca   1380
cacctgattg tccatcaaag aagccacaca ggagaaaaac cttatcagtg ccacaactgt   1440
gggaaatcct tcatttccaa gtcacagctt gatatacatc atcgaattca tacaggggag   1500
aaaccttatg aatgcagtga ctgtggaaaa accttcaccc aaaagtcaca cctgaatata   1560
caccagaaaa ttcatactgg agaaagacac catgtatgca gtgaatgcgg aaagccttc   1620
aaccagaagt caatactcag catgcatcag agaattcaca ccggagagaa gccttacaaa   1680
tgcagtgaat gtgggaaagc cttcacttct aagtctcaat tcaaagagca tcagcgaatt   1740
```

```
cacacgggtg agaaaccccta tgtgtgcact gaatgtggga aggccttcaa cggcaggtca   1800
aatttccata acatcaaat aactcacact agagagaggc ttttgtctg ttacaaatgt     1860 gggaaggctt ttgtccagaa atcagagttg attacccatc aaagaactca tgggagag    1920 aaaccctatg aatgccttga ctgtgggaaa tcgttcagta agaaaccaca actcaaggtg   1980
catcagcgaa ttcacacggg agaaagacct tatgtgtgtt ctgaatgtgg aaaggccttc   2040
aacaacaggt caaacttcaa taaacaccaa acaactcata ccagagacaa atcttacaaa   2100
tgcagttatt ctgtgaaagg ctttaccaag caa                                2133

<210> SEQ ID NO 12
<211> LENGTH: 3754
<212> TYPE: DNA
<213> ORGANISM: Homo sapiens
<220> FEATURE:
<221> NAME/KEY: CDS
<222> LOCATION: (346)..(2478)

<400> SEQUENCE: 12
gctaagccta tgtcgcttac tggacgctga agtgattggg aatattagca gtggggttc    60 tgtagggtca ggaaggggcg ctggctttg ggggagtgat gaggggcttg ttggggtgg    120 gggtgcgtga taaagggatt tctcggctga agacgaggct gtgaggcttc tgcagaaccc   180
ccaggtcagg ccacatcatt gaggctgcag gatctctctt catagcccag tacgactctc   240
cgccgtgtcc ctggttggaa atccaaaca cctatccagc ttctggctcc tgggaaaagt    300
ggagttgtca gcaagagaga ccgagagtag aagcccagag tggag atg cct gct gat   357
                                                  Met Pro Ala Asp
                                                   1 gtg aat tta tcc cag aag cct cag gtc ctg ggt cca gag aag cag gat    405
Val Asn Leu Ser Gln Lys Pro Gln Val Leu Gly Pro Glu Lys Gln Asp
 5                  10                  15                  20 gga tct tgc gag gca tca gtg tca ttt gag gac gtg acc gtg gac ttc   453
Gly Ser Cys Glu Ala Ser Val Ser Phe Glu Asp Val Thr Val Asp Phe
                 25                  30                  35 agc agg gag gag tgg cag caa ctg gac cct gcc cag aga tgc ctg tac   501
Ser Arg Glu Glu Trp Gln Gln Leu Asp Pro Ala Gln Arg Cys Leu Tyr
             40                  45                  50 cgg gat gtg atg ctg gag ctc tat agc cat ctc ttc gca gtg ggg tat   549
Arg Asp Val Met Leu Glu Leu Tyr Ser His Leu Phe Ala Val Gly Tyr
         55                  60                  65 cac att ccc aac cca gag gtc atc ttc aga atg cta aaa gaa aag gag   597
His Ile Pro Asn Pro Glu Val Ile Phe Arg Met Leu Lys Glu Lys Glu
     70                  75                  80 ccg cgt gtg gag gag gct gaa gtc tca cat cag agg tgt caa gaa agg   645
Pro Arg Val Glu Glu Ala Glu Val Ser His Gln Arg Cys Gln Glu Arg
 85                  90                  95                 100 gag ttt ggg ctt gaa atc cca caa aag gag att tct aag aaa gct tca   693
Glu Phe Gly Leu Glu Ile Pro Gln Lys Glu Ile Ser Lys Lys Ala Ser
                105                 110                 115 ttt caa aag gat atg gta ggt gag ttc aca aga gat ggt tca tgg tgt   741
Phe Gln Lys Asp Met Val Gly Glu Phe Thr Arg Asp Gly Ser Trp Cys
            120                 125                 130 tcc att tta gaa gaa ctg agg ctg gat gct gac cgc aca aag aaa gat   789
Ser Ile Leu Glu Glu Leu Arg Leu Asp Ala Asp Arg Thr Lys Lys Asp
        135                 140                 145 gag caa aat caa att caa ccc atg agt cac agt gct ttc ttc aac aag   837
Glu Gln Asn Gln Ile Gln Pro Met Ser His Ser Ala Phe Phe Asn Lys
    150                 155                 160 aaa aca ttg aac aca gaa agc aat tgt gaa tat aag gac cct ggg aaa   885
```

```
Lys Thr Leu Asn Thr Glu Ser Asn Cys Glu Tyr Lys Asp Pro Gly Lys
165                 170                 175                 180 atg att cgc acg agg ccc cac ctt gct tct tca cag aaa caa cct cag        933
Met Ile Arg Thr Arg Pro His Leu Ala Ser Ser Gln Lys Gln Pro Gln
                185                 190                 195 aaa tgt tgc tta ttt aca gaa agt ttg aag ctg aac cta gaa gtg aac        981
Lys Cys Cys Leu Phe Thr Glu Ser Leu Lys Leu Asn Leu Glu Val Asn
            200                 205                 210 ggt cag aat gaa agc aat gac aca gaa cag ctt gat gac gtt gtt ggg       1029
Gly Gln Asn Glu Ser Asn Asp Thr Glu Gln Leu Asp Asp Val Val Gly
        215                 220                 225 tct ggt cag cta ttc agc cat agc tct tct gat gcc tgc agc aag aat       1077
Ser Gly Gln Leu Phe Ser His Ser Ser Ser Asp Ala Cys Ser Lys Asn
230                 235                 240 att cat aca gga gag aca ttt tgc aaa ggt aac cag tgt aga aaa gtc       1125
Ile His Thr Gly Glu Thr Phe Cys Lys Gly Asn Gln Cys Arg Lys Val
245                 250                 255                 260 tgt ggc cat aaa cag tca ctc aag caa cat caa att cat act cag aag       1173
Cys Gly His Lys Gln Ser Leu Lys Gln His Gln Ile His Thr Gln Lys
                265                 270                 275 aaa cca gat gga tgt tct gaa tgt ggg ggg agc ttc acc cag aag tca       1221
Lys Pro Asp Gly Cys Ser Glu Cys Gly Gly Ser Phe Thr Gln Lys Ser
            280                 285                 290 cac ctc ttt gcc caa cag aga att cat agt gta gga aac ctc cat gaa       1269
His Leu Phe Ala Gln Gln Arg Ile His Ser Val Gly Asn Leu His Glu
        295                 300                 305 tgt ggc aaa tgt gga aaa gcc ttc atg cca caa cta aaa ctc agt gta       1317
Cys Gly Lys Cys Gly Lys Ala Phe Met Pro Gln Leu Lys Leu Ser Val
310                 315                 320 tat ctg aca gat cat aca ggt gat ata ccc tgt ata tgc aag gaa tgt       1365
Tyr Leu Thr Asp His Thr Gly Asp Ile Pro Cys Ile Cys Lys Glu Cys
325                 330                 335                 340 ggg aag gtc ttt att cag aga tca gaa ttg ctt acg cac cag aaa aca       1413
Gly Lys Val Phe Ile Gln Arg Ser Glu Leu Leu Thr His Gln Lys Thr
                345                 350                 355 cac act aga aag aag ccc tat aaa tgc cat gac tgt gga aaa gcc ttt       1461
His Thr Arg Lys Lys Pro Tyr Lys Cys His Asp Cys Gly Lys Ala Phe
            360                 365                 370 ttc cag atg tta tct ctc ttc aga cat cag aga act cac agt aga gaa       1509
Phe Gln Met Leu Ser Leu Phe Arg His Gln Arg Thr His Ser Arg Glu
        375                 380                 385 aaa ctc tat gaa tgc agt gaa tgt ggc aaa ggc ttc tcc caa aac tca       1557
Lys Leu Tyr Glu Cys Ser Glu Cys Gly Lys Gly Phe Ser Gln Asn Ser
390                 395                 400 acc ctc att ata cat cag aaa att cat act ggt gag aga cag tat gca       1605
Thr Leu Ile Ile His Gln Lys Ile His Thr Gly Glu Arg Gln Tyr Ala
405                 410                 415                 420 tgc agt gaa tgt ggg aaa gcc ttt acc cag aag tca aca ctc agc ttg       1653
Cys Ser Glu Cys Gly Lys Ala Phe Thr Gln Lys Ser Thr Leu Ser Leu
                425                 430                 435 cac cag aga atc cac tca ggg cag aag tcc tat gtg tgt atc gaa tgc       1701
His Gln Arg Ile His Ser Gly Gln Lys Ser Tyr Val Cys Ile Glu Cys
            440                 445                 450 ggg cag gcc ttc atc cag aag gca cac ctg att gtc cat caa aga agc       1749
Gly Gln Ala Phe Ile Gln Lys Ala His Leu Ile Val His Gln Arg Ser
        455                 460                 465 cac aca gga gaa aaa cct tat cag tgc cac aac tgt ggg aaa tcc ttc       1797
His Thr Gly Glu Lys Pro Tyr Gln Cys His Asn Cys Gly Lys Ser Phe
470                 475                 480 att tcc aag tca cag ctt gat ata cat cat cga att cat aca ggg gag       1845
```

```
Ile Ser Lys Ser Gln Leu Asp Ile His His Arg Ile His Thr Gly Glu
485                 490                 495                 500 aaa cct tat gaa tgc agt gac tgt gga aaa acc ttc acc caa aag tca    1893
Lys Pro Tyr Glu Cys Ser Asp Cys Gly Lys Thr Phe Thr Gln Lys Ser
                505                 510                 515 cac ctg aat ata cac cag aaa att cat act gga gaa aga cac cat gta    1941
His Leu Asn Ile His Gln Lys Ile His Thr Gly Glu Arg His His Val
            520                 525                 530 tgc agt gaa tgc ggg aaa gcc ttc aac cag aag tca ata ctc agc atg    1989
Cys Ser Glu Cys Gly Lys Ala Phe Asn Gln Lys Ser Ile Leu Ser Met
        535                 540                 545 cat cag aga att cac acc gga gag aag cct tac aaa tgc agt gaa tgt    2037
His Gln Arg Ile His Thr Gly Glu Lys Pro Tyr Lys Cys Ser Glu Cys
    550                 555                 560 ggg aaa gcc ttc act tct aag tct caa ttc aaa gag cat cag cga att    2085
Gly Lys Ala Phe Thr Ser Lys Ser Gln Phe Lys Glu His Gln Arg Ile
565                 570                 575                 580 cac acg ggt gag aaa ccc tat gtg tgc act gaa tgt ggg aag gcc ttc    2133
His Thr Gly Glu Lys Pro Tyr Val Cys Thr Glu Cys Gly Lys Ala Phe
                585                 590                 595 aac ggc agg tca aat ttc cat aaa cat caa ata act cac act aga gag    2181
Asn Gly Arg Ser Asn Phe His Lys His Gln Ile Thr His Thr Arg Glu
            600                 605                 610 agg cct ttt gtc tgt tac aaa tgt ggg aag gct ttt gtc cag aaa tca    2229
Arg Pro Phe Val Cys Tyr Lys Cys Gly Lys Ala Phe Val Gln Lys Ser
        615                 620                 625 gag ttg att acc cat caa aga act cac atg gga gag aaa ccc tat gaa    2277
Glu Leu Ile Thr His Gln Arg Thr His Met Gly Glu Lys Pro Tyr Glu
    630                 635                 640 tgc ctt gac tgt ggg aaa tcg ttc agt aag aaa cca caa ctc aag gtg    2325
Cys Leu Asp Cys Gly Lys Ser Phe Ser Lys Lys Pro Gln Leu Lys Val
645                 650                 655                 660 cat cag cga att cac acg gga gaa aga cct tat gtg tgt tct gaa tgt    2373
His Gln Arg Ile His Thr Gly Glu Arg Pro Tyr Val Cys Ser Glu Cys
                665                 670                 675 gga aag gcc ttc aac aac agg tca aac ttc aat aaa cac caa aca act    2421
Gly Lys Ala Phe Asn Asn Arg Ser Asn Phe Asn Lys His Gln Thr Thr
            680                 685                 690 cat acc aga gac aaa tct tac aaa tgc agt tat tct gtg aaa ggc ttt    2469
His Thr Arg Asp Lys Ser Tyr Lys Cys Ser Tyr Ser Val Lys Gly Phe
        695                 700                 705 acc aag caa tgaattccta gtgcatcagc atattcataa atgaaatata           2518
Thr Lys Gln
    710 ctccgagttt cttgaagaag agaacatctt ctcagaatca ggtctaatta tatgttattg  2578 aattcatgct tcagaaaaac tctagggatg cactgcatgt gtgaacacat gataaaaaag  2638 tcatgcttta ttttagtgag ggcaattaca gagaaaagag taagcagaaa tgtccttctg  2698 agtactggcc tcattaagga ttataaattt tctccccggg aagaaccct gactaacgca   2758 ttgagaaaag cctttctgta aagaatggta caagacaggt tgttactcga ttatttatag  2818 taaaatatgt gggaaattat atcaatgata accctgttta ttgtgggata tcaatatttt  2878 taaagtgcca acacagtcat gataggacaa tattttatgt gtgtgtgtgc gccttatgta  2938 tataagcata tataatat ataagcatat tattatatac aggttgagta tcccttctcc    2998 aaaatgcctg ggatcagaag cattttggat ttcagatact tacagatttt ggaatatttg  3058 cattatattt attggttgag catccctaat ctgaaaatcc aagattaaat gctccaatta  3118 gcatttcctt tgagcgtcat gttagagttc aaaaagtttc agattttggg ttttcagatt  3178
```

```
aggaataccc aacctgtatg tacgtatatt tctgtatcta tgtatgtata tatatgcata    3238
tgcagacata tgtatatggt ctggtcagca tatgtgtatg tatgcgtatg tatgtatgta    3298
tgtatgccct cagtgcagtg gggtttgctg cagaattcac tgcatagcag gagatgtaag    3358
cagatgagtt attttttaag agaatctaat ctaattgttt ttataaaaat tattccctat    3418
tgaatattta taatgaggg ttgtatcaac aatgattaac tcctttatta tacatacaca    3478
tgaatgtgca tttttggtaa atgcataaat gagattctat aatgtttact gatctttata    3538
ttacagattt tctcttcttt taggattagc tcagcttgcc cccctttcc atctccacca    3598 tctatagtga gcctctccat aattagtgcc aaccattagt ctcgttcata ttttttacacc   3658 aggagtcaac aaactgtgcc attggccaaa tatggcctcc caactgtttt tttaaaataa    3718
agttttattg gaacacaaaa aaaaaaaaaa aaaaaa                              3754
```

<210> SEQ ID NO 13
<211> LENGTH: 389
<212> TYPE: PRT
<213> ORGANISM: Homo sapiens

<400> SEQUENCE: 13

```
Met Ala Asp Pro Arg Asp Lys Ala Leu Gln Asp Tyr Arg Lys Lys Leu
 1               5                  10                  15

Leu Glu His Lys Glu Ile Asp Gly Arg Leu Lys Glu Leu Arg Glu Gln
             20                  25                  30

Leu Lys Glu Leu Thr Lys Gln Tyr Glu Lys Ser Glu Asn Asp Leu Lys
         35                  40                  45

Ala Leu Gln Ser Val Gly Gln Ile Val Gly Glu Val Leu Lys Gln Leu
     50                  55                  60

Thr Glu Glu Lys Phe Ile Val Lys Ala Thr Asn Gly Pro Arg Tyr Val
 65                  70                  75                  80

Val Gly Cys Arg Arg Gln Leu Asp Lys Ser Lys Leu Lys Pro Gly Thr
                 85                  90                  95

Arg Val Ala Leu Asp Met Thr Thr Leu Thr Ile Met Arg Tyr Leu Pro
            100                 105                 110

Arg Glu Val Asp Pro Leu Val Tyr Asn Met Ser His Glu Asp Pro Gly
        115                 120                 125

Asn Val Ser Tyr Ser Glu Ile Gly Gly Leu Ser Glu Gln Ile Arg Glu
    130                 135                 140

Leu Arg Glu Val Ile Glu Leu Pro Leu Thr Asn Pro Glu Leu Phe Gln
145                 150                 155                 160

Arg Val Gly Ile Ile Pro Pro Lys Gly Cys Leu Leu Tyr Gly Pro Pro
                165                 170                 175

Gly Thr Gly Lys Thr Leu Leu Ala Arg Ala Val Ala Ser Gln Leu Asp
            180                 185                 190

Cys Asn Phe Leu Lys Val Val Ser Ser Ile Val Asp Lys Tyr Ile
        195                 200                 205

Gly Glu Ser Ala Arg Leu Ile Arg Glu Met Phe Asn Tyr Ala Arg Asp
    210                 215                 220

His Gln Pro Cys Ile Ile Phe Met Asp Glu Ile Asp Ala Ile Gly Gly
225                 230                 235                 240

Arg Arg Phe Ser Glu Gly Thr Ser Ala Asp Arg Glu Ile Gln Arg Thr
                245                 250                 255

Leu Met Glu Leu Leu Asn Gln Met Asp Gly Phe Asp Thr Leu His Arg
            260                 265                 270
```

```
Val Lys Met Thr Met Ala Thr Asn Arg Pro Asp Thr Leu Asp Pro Ala
        275                 280                 285

Leu Leu Arg Pro Gly Arg Leu Asp Arg Lys Ile His Ile Asp Leu Pro
    290                 295                 300

Asn Glu Gln Ala Arg Leu Asp Ile Leu Lys Ile His Ala Gly Pro Ile
305                 310                 315                 320

Thr Lys His Gly Glu Ile Asp Tyr Glu Ala Ile Val Lys Leu Ser Asp
                325                 330                 335

Gly Phe Asn Gly Ala Asp Leu Arg Asn Val Cys Thr Glu Ala Gly Met
                340                 345                 350

Phe Ala Ile Arg Ala Asp His Asp Phe Val Val Gln Glu Asp Phe Met
            355                 360                 365

Lys Ala Val Arg Lys Val Ala Asp Ser Lys Lys Leu Glu Ser Lys Leu
    370                 375                 380

Asp Tyr Lys Pro Val
385

<210> SEQ ID NO 14
<211> LENGTH: 1167
<212> TYPE: DNA
<213> ORGANISM: Homo sapiens

<400> SEQUENCE: 14
atggcggacc ctagagataa ggcgcttcag gactaccgca agaagttgct tgaacacaag      60
gagatcgacg gccgtcttaa ggagttaagg gaacaattaa agaacttac caagcagtat     120 gaaaagtctg aaaatgatct gaaggcccta cagagtgttg ggcagatcgt gggtgaagtg     180
cttaaacagt taactgaaga aaaattcatt gttaaagcta ccaatggacc aagatatgtt     240
gtgggttgtc gtcgacagct tgacaaaagt aagctgaagc caggaacaag agttgctttg     300
gatatgacta cactaactat catgagatat ttgccgagag aggtggatcc actggtttat     360
aacatgtctc atgaggaccc tgggaatgtt tcttattctg agattggagg ctatcagaa     420 cagatccggg aattaagaga ggtgatagaa ttacctctta caaacccaga gttatttcag     480
cgtgtaggaa taatacctcc aaaaggctgt tgttatatg gaccaccagg tacgggaaaa     540
acactcttgg cacgagccgt tgctagccag ctggactgca atttcttaaa ggttgtatct     600
agttctattg tagacaagta cattggtgaa agtgctcgtt tgatcagaga atgtttaat     660 tatgctagag atcatcaacc atgcatcatt tttatggatg aaatagatgc tattggtggt     720
cgtcggtttt ctgagggtac ttcagctgac agagagattc agagaacgtt aatgagtta     780 ctgaatcaaa tggatggatt tgatactctg catagagtta aaatgaccat ggctacaaac     840
agaccagata cactggatcc tgctttgctg cgtccaggaa gattagatag aaaaatacat     900
attgatttgc caatgaaca agcaagatta gacatactga aaatccatgc aggtcccatt     960
acaaagcatg gtgaaataga ttatgaagca attgtgaagc tttcggatgg ctttaatgga    1020
gcagatctga aaatgtttg tactgaagca ggtatgttcg caattcgtgc tgatcatgat    1080
tttgtagtac aggaagactt catgaaagca gtcagaaaag tggctgattc taagaagctg    1140
gagtctaaat tggactacaa acctgtg                                       1167

<210> SEQ ID NO 15
<211> LENGTH: 1566
<212> TYPE: DNA
<213> ORGANISM: Homo sapiens
<220> FEATURE:
<221> NAME/KEY: CDS
<222> LOCATION: (17)..(1183)
```

<400> SEQUENCE: 15

```
gagacggctt ctcatc atg gcg gac cct aga gat aag gcg ctt cag gac tac        52
                  Met Ala Asp Pro Arg Asp Lys Ala Leu Gln Asp Tyr
                   1               5                  10 cgc aag aag ttg ctt gaa cac aag gag atc gac ggc cgt ctt aag gag           100
Arg Lys Lys Leu Leu Glu His Lys Glu Ile Asp Gly Arg Leu Lys Glu
         15                  20                  25 tta agg gaa caa tta aaa gaa ctt acc aag cag tat gaa aag tct gaa           148
Leu Arg Glu Gln Leu Lys Glu Leu Thr Lys Gln Tyr Glu Lys Ser Glu
 30                  35                  40 aat gat ctg aag gcc cta cag agt gtt ggg cag atc gtg ggt gaa gtg           196
Asn Asp Leu Lys Ala Leu Gln Ser Val Gly Gln Ile Val Gly Glu Val
 45                  50                  55                  60 ctt aaa cag tta act gaa gaa aaa ttc att gtt aaa gct acc aat gga           244
Leu Lys Gln Leu Thr Glu Glu Lys Phe Ile Val Lys Ala Thr Asn Gly
                 65                  70                  75 cca aga tat gtt gtg ggt tgt cgt cga cag ctt gac aaa agt aag ctg           292
Pro Arg Tyr Val Val Gly Cys Arg Arg Gln Leu Asp Lys Ser Lys Leu
             80                  85                  90 aag cca gga aca aga gtt gct ttg gat atg act aca cta act atc atg           340
Lys Pro Gly Thr Arg Val Ala Leu Asp Met Thr Thr Leu Thr Ile Met
         95                 100                 105 aga tat ttg ccg aga gag gtg gat cca ctg gtt tat aac atg tct cat           388
Arg Tyr Leu Pro Arg Glu Val Asp Pro Leu Val Tyr Asn Met Ser His
110                 115                 120 gag gac cct ggg aat gtt tct tat tct gag att gga ggg cta tca gaa           436
Glu Asp Pro Gly Asn Val Ser Tyr Ser Glu Ile Gly Gly Leu Ser Glu
125                 130                 135                 140 cag atc cgg gaa tta aga gag gtg ata gaa tta cct ctt aca aac cca           484
Gln Ile Arg Glu Leu Arg Glu Val Ile Glu Leu Pro Leu Thr Asn Pro
                145                 150                 155 gag tta ttt cag cgt gta gga ata ata cct cca aaa ggc tgt ttg tta           532
Glu Leu Phe Gln Arg Val Gly Ile Ile Pro Pro Lys Gly Cys Leu Leu
            160                 165                 170 tat gga cca cca ggt acg gga aaa aca ctc ttg gca cga gcc gtt gct           580
Tyr Gly Pro Pro Gly Thr Gly Lys Thr Leu Leu Ala Arg Ala Val Ala
        175                 180                 185 agc cag ctg gac tgc aat ttc tta aag gtt gta tct agt tct att gta           628
Ser Gln Leu Asp Cys Asn Phe Leu Lys Val Val Ser Ser Ser Ile Val
    190                 195                 200 gac aag tac att ggt gaa agt gct cgt ttg atc aga gaa atg ttt aat           676
Asp Lys Tyr Ile Gly Glu Ser Ala Arg Leu Ile Arg Glu Met Phe Asn
205                 210                 215                 220 tat gct aga gat cat caa cca tgc atc att ttt atg gat gaa ata gat           724
Tyr Ala Arg Asp His Gln Pro Cys Ile Ile Phe Met Asp Glu Ile Asp
                225                 230                 235 gct att ggt ggt cgt cgg ttt tct gag ggt act tca gct gac aga gag           772
Ala Ile Gly Gly Arg Arg Phe Ser Glu Gly Thr Ser Ala Asp Arg Glu
            240                 245                 250 att cag aga acg tta atg gag tta ctg aat caa atg gat gga ttt gat           820
Ile Gln Arg Thr Leu Met Glu Leu Leu Asn Gln Met Asp Gly Phe Asp
        255                 260                 265 act ctg cat aga gtt aaa atg acc atg gct aca aac aga cca gat aca           868
Thr Leu His Arg Val Lys Met Thr Met Ala Thr Asn Arg Pro Asp Thr
    270                 275                 280 ctg gat cct gct ttg ctg cgt cca gga aga tta gat aga aaa ata cat           916
Leu Asp Pro Ala Leu Leu Arg Pro Gly Arg Leu Asp Arg Lys Ile His
285                 290                 295                 300 att gat ttg cca aat gaa caa gca aga tta gac ata ctg aaa atc cat           964
```

```
                Ile Asp Leu Pro Asn Glu Gln Ala Arg Leu Asp Ile Leu Lys Ile His
                                305                 310                 315 gca ggt ccc att aca aag cat ggt gaa ata gat tat gaa gca att gtg         1012
Ala Gly Pro Ile Thr Lys His Gly Glu Ile Asp Tyr Glu Ala Ile Val
            320                 325                 330 aag ctt tcg gat ggc ttt aat gga gca gat ctg aga aat gtt tgt act         1060
Lys Leu Ser Asp Gly Phe Asn Gly Ala Asp Leu Arg Asn Val Cys Thr
        335                 340                 345 gaa gca ggt atg ttc gca att cgt gct gat cat gat ttt gta gta cag         1108
Glu Ala Gly Met Phe Ala Ile Arg Ala Asp His Asp Phe Val Val Gln
    350                 355                 360 gaa gac ttc atg aaa gca gtc aga aaa gtg gct gat tct aag aag ctg         1156
Glu Asp Phe Met Lys Ala Val Arg Lys Val Ala Asp Ser Lys Lys Leu
365                 370                 375                 380 gag tct aaa ttg gac tac aaa cct gtg taatttactg taagattttt               1203
Glu Ser Lys Leu Asp Tyr Lys Pro Val
                385 gatggctgca tgacagatgt tggcttattg taaaaataaa gttaaagaaa ataatgtatg       1263 tattggcaat gatgtcatta aaagtatatg aataaaaata tgagtaacat cataaaaatt      1323 agtaattcaa cttttaagat acagaagaaa tttgtatgtt tgttaaagtt gcatttattg      1383 cagcaagtta caagggaaa gtgttgaagc ttttcatatt tgctgcgtga gcattttgta       1443 aaatattgaa agtggtttga gatagtggta taagaaagca tttcttatga cttattttgt      1503 atcatttgtt ttcctcatct aaaagttgaa ataaaatctg tttgattcag ttctcctaaa      1563 aaa                                                                    1566

<210> SEQ ID NO 16
<211> LENGTH: 223
<212> TYPE: PRT
<213> ORGANISM: Homo sapiens

<400> SEQUENCE: 16

Met Ser Asp Glu Glu Ala Arg Gln Ser Gly Ser Ser Gln Ala Gly
1               5                   10                  15

Val Val Thr Val Ser Asp Val Gln Glu Leu Met Arg Arg Lys Glu Glu
            20                  25                  30

Ile Glu Ala Gln Ile Lys Ala Asn Tyr Asp Val Leu Glu Ser Gln Lys
        35                  40                  45

Gly Ile Gly Met Asn Glu Pro Leu Val Asp Cys Glu Gly Tyr Pro Arg
    50                  55                  60

Ser Asp Val Asp Leu Tyr Gln Val Arg Thr Ala Arg His Asn Ile Ile
65                  70                  75                  80

Cys Leu Gln Asn Asp His Lys Ala Val Met Lys Gln Val Glu Glu Ala
                85                  90                  95

Leu His Gln Leu His Ala Arg Asp Lys Glu Lys Gln Ala Arg Asp Met
            100                 105                 110

Ala Glu Ala His Lys Glu Ala Met Ser Arg Lys Leu Gly Gln Ser Glu
        115                 120                 125

Ser Gln Gly Pro Pro Arg Ala Phe Ala Lys Val Asn Ser Ile Ser Pro
    130                 135                 140

Gly Ser Pro Ala Ser Ile Ala Gly Leu Gln Val Asp Asp Glu Ile Val
145                 150                 155                 160

Glu Phe Gly Ser Val Asn Thr Gln Asn Phe Gln Ser Leu His Asn Ile
                165                 170                 175

Gly Ser Val Val Gln His Ser Glu Gly Lys Pro Leu Asn Val Thr Val
            180                 185                 190
```

```
Ile Arg Arg Gly Glu Lys His Gln Leu Arg Leu Val Pro Thr Arg Trp
    195                 200                 205

Ala Gly Lys Gly Leu Leu Gly Cys Asn Ile Ile Pro Leu Gln Arg
    210                 215                 220

<210> SEQ ID NO 17
<211> LENGTH: 669
<212> TYPE: DNA
<213> ORGANISM: Homo sapiens

<400> SEQUENCE: 17
atgtccgacg aggaagcgag gcagagcgga ggctcctcgc aggccggcgt cgtgactgtc      60
agcgacgtcc aggagctgat gcggcgcaag gaggagatag aagcgcagat caaggccaac     120
tatgacgtgc tggaaagcca aaaaggcatt gggatgaacg agccgctggt ggactgtgag     180
ggctaccccc ggtcagacgt ggacctgtac caagtccgca ccgccaggca caacatcata     240
tgcctgcaga atgatcacaa ggcagtgatg aagcaggtgg aggaggccct gcaccagctg     300
cacgctcgcg acaaggagaa gcaggcccgg gacatggctg aggcccacaa agaggccatg     360
agccgcaaac tgggtcagag tgagagccag ggccctccac gggccttcgc caaagtgaac     420
agcatcagcc ccggctcccc agccagcatc gcgggtctgc aagtggatga tgagattgtg     480
gagttcggct ctgtgaacac ccagaacttc cagtcactgc ataacattgg cagtgtggtg     540
cagcacagtg aggggaagcc cctgaatgtg acagtgatcc gcagggggga aaaacaccag     600
cttagacttg ttccaacacg ctgggcagga aaggactgc tgggctgcaa cattattcct      660
ctgcaaaga                                                              669

<210> SEQ ID NO 18
<211> LENGTH: 1128
<212> TYPE: DNA
<213> ORGANISM: Homo sapiens
<220> FEATURE:
<221> NAME/KEY: CDS
<222> LOCATION: (125)..(793)

<400> SEQUENCE: 18
actgttctcg cgttcgcgga cggctgtggt gttttggcgc atgggcggag cgtagttacg      60
gtcgactggg gcgtcgtccc tagcccggga gccgggtctc tggagtcgcg gcccggggtt    120 cacg atg tcc gac gag gaa gcg agg cag agc gga ggc tcc tcg cag gcc     169
     Met Ser Asp Glu Glu Ala Arg Gln Ser Gly Gly Ser Ser Gln Ala
     1               5                   10                  15 ggc gtc gtg act gtc agc gac gtc cag gag ctg atg cgg cgc aag gag     217
Gly Val Val Thr Val Ser Asp Val Gln Glu Leu Met Arg Arg Lys Glu
            20                  25                  30 gag ata gaa gcg cag atc aag gcc aac tat gac gtg ctg gaa agc caa     265
Glu Ile Glu Ala Gln Ile Lys Ala Asn Tyr Asp Val Leu Glu Ser Gln
        35                  40                  45 aaa ggc att ggg atg aac gag ccg ctg gtg gac tgt gag ggc tac ccc     313
Lys Gly Ile Gly Met Asn Glu Pro Leu Val Asp Cys Glu Gly Tyr Pro
    50                  55                  60 cgg tca gac gtg gac ctg tac caa gtc cgc acc gcc agg cac aac atc     361
Arg Ser Asp Val Asp Leu Tyr Gln Val Arg Thr Ala Arg His Asn Ile
65                  70                  75 ata tgc ctg cag aat gat cac aag gca gtg atg aag cag gtg gag gag     409
Ile Cys Leu Gln Asn Asp His Lys Ala Val Met Lys Gln Val Glu Glu
                80                  85                  90              95 gcc ctg cac cag ctg cac gct cgc gac aag gag aag cag gcc cgg gac     457
Ala Leu His Gln Leu His Ala Arg Asp Lys Glu Lys Gln Ala Arg Asp
```

```
            100               105                110
atg gct gag gcc cac aaa gag gcc atg agc cgc aaa ctg ggt cag agt      505
Met Ala Glu Ala His Lys Glu Ala Met Ser Arg Lys Leu Gly Gln Ser
            115               120                125 gag agc cag ggc cct cca cgg gcc ttc gcc aaa gtg aac agc atc agc      553
Glu Ser Gln Gly Pro Pro Arg Ala Phe Ala Lys Val Asn Ser Ile Ser
        130               135                140 ccc ggc tcc cca gcc agc atc gcg ggt ctg caa gtg gat gat gag att      601
Pro Gly Ser Pro Ala Ser Ile Ala Gly Leu Gln Val Asp Asp Glu Ile
    145               150                155 gtg gag ttc ggc tct gtg aac acc cag aac ttc cag tca ctg cat aac      649
Val Glu Phe Gly Ser Val Asn Thr Gln Asn Phe Gln Ser Leu His Asn
160               165                170                175 att ggc agt gtg gtg cag cac agt gag ggg aag ccc ctg aat gtg aca      697
Ile Gly Ser Val Val Gln His Ser Glu Gly Lys Pro Leu Asn Val Thr
            180               185                190 gtg atc cgc agg ggg gaa aaa cac cag ctt aga ctt gtt cca aca cgc      745
Val Ile Arg Arg Gly Glu Lys His Gln Leu Arg Leu Val Pro Thr Arg
        195               200                205 tgg gca gga aaa gga ctg ctg ggc tgc aac att att cct ctg caa aga      793
Trp Ala Gly Lys Gly Leu Leu Gly Cys Asn Ile Ile Pro Leu Gln Arg
    210               215                220 tgattgtccc tggggaacag taacaggaaa gcatcttccc ttgccctgga cttgggtcta    853
gggatttcca acttgtcttc tctccctgaa gcataaggat ctggaagagg cttgtaacct    913
gaacttctgt gtggtggcag tactgtggcc caccagtgta atctccctgg attaaggcat    973
tcttaaaaac ttaggcttgg cctctttcac aaattaggcc acggccctaa ataggaattc   1033
cctggattgt gggcaagtgg gcggaagtta ttctggcagg tactggtgtg attattatta   1093
ttattttttaa taaagagttt tacagtgctg atatg                             1128

<210> SEQ ID NO 19
<211> LENGTH: 506
<212> TYPE: PRT
<213> ORGANISM: Homo sapiens

<400> SEQUENCE: 19

Met Ala Glu Ala Asp Phe Lys Met Val Ser Glu Pro Val Ala His Gly
 1               5                  10                  15

Val Ala Glu Glu Glu Met Ala Ser Ser Thr Ser Asp Ser Gly Glu Glu
            20                  25                  30

Ser Asp Ser Ser Ser Ser Ser Ser Thr Ser Asp Ser Ser Ser Ser
        35                  40                  45

Ser Ser Thr Ser Gly Ser Ser Gly Ser Gly Ser Ser Ser Ser
    50                  55                  60

Ser Gly Ser Thr Ser Ser Arg Ser Arg Leu Tyr Arg Lys Arg Val
65                  70                  75                  80

Pro Glu Pro Ser Arg Arg Ala Arg Arg Ala Pro Leu Gly Thr Asn Phe
                85                  90                  95

Val Asp Arg Leu Pro Gln Ala Val Arg Asn Arg Val Gln Ala Leu Arg
            100                 105                 110

Asn Ile Gln Asp Glu Cys Asp Lys Val Asp Thr Leu Phe Leu Lys Ala
        115                 120                 125

Ile His Asp Leu Glu Arg Lys Tyr Ala Glu Leu Asn Lys Pro Leu Tyr
    130                 135                 140

Asp Arg Arg Phe Gln Ile Ile Asn Ala Glu Tyr Glu Pro Thr Glu Glu
145                 150                 155                 160
```

Glu Cys Glu Trp Asn Ser Gly Asp Glu Glu Phe Ser Ser Asp Glu Glu
                165                 170                 175

Val Gln Asp Asn Thr Pro Ser Glu Met Pro Pro Leu Glu Gly Glu Glu
        180                 185                 190

Glu Glu Asn Pro Lys Glu Asn Pro Glu Val Lys Ala Glu Glu Lys Glu
    195                 200                 205

Val Pro Lys Glu Ile Pro Glu Val Lys Asp Glu Glu Lys Glu Val Ala
210                 215                 220

Lys Glu Ile Pro Glu Val Lys Ala Glu Glu Lys Ala Asp Ser Lys Asp
225                 230                 235                 240

Cys Met Glu Ala Thr Pro Glu Val Lys Glu Asp Pro Lys Glu Val Pro
                245                 250                 255

Gln Val Lys Ala Asp Asp Lys Glu Gln Pro Lys Ala Thr Glu Ala Lys
        260                 265                 270

Ala Arg Ala Ala Val Arg Glu Thr His Lys Arg Val Pro Glu Glu Arg
    275                 280                 285

Leu Arg Asp Ser Val Asp Leu Lys Arg Ala Arg Lys Gly Lys Pro Lys
290                 295                 300

Arg Glu Asp Pro Lys Gly Ile Pro Asp Tyr Trp Leu Ile Val Leu Lys
305                 310                 315                 320

Asn Val Asp Lys Leu Gly Pro Met Ile Gln Lys Tyr Asp Glu Pro Ile
                325                 330                 335

Leu Lys Phe Leu Ser Asp Val Ser Leu Lys Phe Ser Lys Pro Gly Gln
        340                 345                 350

Pro Val Ser Tyr Thr Phe Glu His Phe Leu Pro Asn Pro Tyr Phe
    355                 360                 365

Arg Asn Glu Val Leu Val Lys Thr Tyr Ile Ile Lys Ala Lys Pro Asp
370                 375                 380

His Asn Asp Pro Phe Phe Ser Trp Gly Trp Glu Ile Glu Asp Cys Lys
385                 390                 395                 400

Gly Cys Lys Ile Asp Arg Arg Gly Lys Asp Val Thr Val Thr Thr
                405                 410                 415

Thr Gln Ser Arg Thr Thr Ala Thr Gly Glu Ile Glu Ile Gln Pro Arg
        420                 425                 430

Val Val Pro Asn Ala Ser Phe Phe Asn Phe Phe Ser Pro Pro Glu Ile
    435                 440                 445

Pro Met Ile Gly Lys Leu Glu Pro Arg Glu Asp Ala Ile Leu Asp Glu
450                 455                 460

Asp Phe Glu Ile Gly Gln Ile Leu His Asp Asn Val Ile Leu Lys Ser
465                 470                 475                 480

Ile Tyr Tyr Tyr Thr Gly Glu Val Asn Gly Thr Tyr Tyr Gln Phe Gly
                485                 490                 495

Lys His Tyr Gly Asn Lys Lys Tyr Arg Lys
        500                 505

<210> SEQ ID NO 20
<211> LENGTH: 1518
<212> TYPE: DNA
<213> ORGANISM: Homo sapiens

<400> SEQUENCE: 20
atggcagaag cagattttaa aatggtctcg gaacctgtcg cccatggggt tgccgaagag      60
gagatggcta gctcgactag tgattctggg gaagaatctg acagcagtag ctctagcagc     120
agcactagtg acagcagcag cagcagcagc actagtggca gcagcagcgg cagcggcagc     180

-continued

| | |
|---|---|
| agcagcagca gcagcggcag cactagcagc cgcagccgct tgtatagaaa gaagagggta | 240 |
| cctgagcctt ccagaagggc gcggcgggcc ccgttgggaa caaatttcgt ggataggctg | 300 |
| cctcaggcag ttagaaatcg tgtgcaagcg cttagaaaca ttcaagatga atgtgacaag | 360 |
| gtagataccc tgttcttaaa agcaattcat gatcttgaaa gaaatatatgc tgaactcaac | 420 |
| aagcctctgt atgataggcg gtttcaaatc atcaatgcag aatacgagcc tacagaagaa | 480 |
| gaatgtgaat ggaattcaga ggatgaggag ttcagcagtg atgaggaggt gcaggataac | 540 |
| acccctagtg aaatgcctcc cttagagggt gaggaagaag aaaaccctaa agaaaaccca | 600 |
| gaggtgaaag ctgaagagaa ggaagttcct aaagaaattc ctgaggtgaa ggatgaagaa | 660 |
| aaggaagttg ctaaagaaat tcctgaggta aaggctgaag aaaaagcaga ttctaaagac | 720 |
| tgtatggagg caaccctga gtaaaagaa gatcctaaag aagtccccca ggtaaaggca | 780 |
| gatgataaag aacagcctaa agcaacagag gctaaggcaa gggctgcagt aagagagact | 840 |
| cataaaagag ttcctgagga aaggcttcgg gacagtgtag atcttaaaag gctaggaag | 900 |
| ggaaagccta aagagaaga ccctaaaggc attcctgact attggctgat tgttttaaag | 960 |
| aatgttgaca gctcgggcc tatgattcag aagtatgatg agcccattct gaagttcttg | 1020 |
| tcggatgtta gcctgaagtt ctcaaaacct ggccagcctg taagttacac ctttgaattt | 1080 |
| cattttctac ccaacccata cttcagaaat gaggtgctgg tgaagacata tataataaag | 1140 |
| gcaaaccag atcacaatga tcccttcttt tcttggggat gggaaattga agattgcaaa | 1200 |
| ggctgcaaga tagaccggag aagaggaaaa gatgttactg tgacaactac ccagagtcgc | 1260 |
| acaactgcta ctggagaaat tgaaatccag ccaagagtgg ttcctaatgc atcattcttc | 1320 |
| aacttcttta gtcctcctga gattcctatg attgggaagc tggaaccacg agaagatgct | 1380 |
| atcctggatg aggactttga aattgggcag atttttacatg ataatgtcat cctgaaatca | 1440 |
| atctattact atactggaga agtcaatggt acctactatc aatttggcaa acattatgga | 1500 |
| aacaagaaat acagaaaaa | 1518 |

<210> SEQ ID NO 21
<211> LENGTH: 2636
<212> TYPE: DNA
<213> ORGANISM: Homo sapiens
<220> FEATURE:
<221> NAME/KEY: CDS
<222> LOCATION: (266)..(1783)

<400> SEQUENCE: 21

| | |
|---|---|
| gattcggctg cggtacatct cggcactcta gctgcagccg ggagaggcct tgccgccacc | 60 |
| gctgtcgccc aagcctccac tgccgctgcc acctcagcgc cggcctctgc atccccagct | 120 |
| ccagctccgc tctgcgccgc tgctgccatc gccgctgcca cctccgcagc ccgggcctcc | 180 |
| gccgccgcca cccaagcatc cgtgagtcat tttctgccca tctctggtcg cgcggtctcc | 240 |
| ctggtagagt ttgtaggctt gcaag atg gca gaa gca gat ttt aaa atg gtc | 292 |
|                              Met Ala Glu Ala Asp Phe Lys Met Val  |
|                               1               5                  |
| tcg gaa cct gtc gcc cat ggg gtt gcc gaa gag gag atg gct agc tcg  | 340 |
| Ser Glu Pro Val Ala His Gly Val Ala Glu Glu Glu Met Ala Ser Ser  |
|  10              15                  20                  25      |
| act agt gat tct ggg gaa gaa tct gac agc agt agc tct agc agc agc  | 388 |
| Thr Ser Asp Ser Gly Glu Glu Ser Asp Ser Ser Ser Ser Ser Ser Ser  |
|              30                  35                  40          |
| act agt gac agc agc agc agc agc agc act agt ggc agc agc agc ggc  | 436 |
| Thr Ser Asp Ser Ser Ser Ser Ser Ser Thr Ser Gly Ser Ser Ser Gly  |
|              45                  50                  55          |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| agc | ggc | agc | agc | agc | agc | agc | ggc | agc | act | agc | agc | cgc | agc | cgc |     | 484 |
| Ser | Gly | Ser | Ser | Ser | Ser | Ser | Gly | Ser | Thr | Ser | Ser | Arg | Ser | Arg |     |     |
|     |     | 60  |     |     |     |     | 65  |     |     |     |     | 70  |     |     |     |     |

| | | | | | | | | | | | | | | | | |
| --- | --- | --- | --- | --- | --- | --- | --- | --- | --- | --- | --- | --- | --- | --- | --- | --- |
| ttg | tat | aga | aag | aag | agg | gta | cct | gag | cct | tcc | aga | agg | gcg | cgg | cgg | 532 |
| Leu | Tyr | Arg | Lys | Lys | Arg | Val | Pro | Glu | Pro | Ser | Arg | Arg | Ala | Arg | Arg |     |
|     | 75  |     |     |     |     | 80  |     |     |     |     | 85  |     |     |     |     |     |

| | | | | | | | | | | | | | | | | |
| --- | --- | --- | --- | --- | --- | --- | --- | --- | --- | --- | --- | --- | --- | --- | --- | --- |
| gcc | ccg | ttg | gga | aca | aat | ttc | gtg | gat | agg | ctg | cct | cag | gca | gtt | aga | 580 |
| Ala | Pro | Leu | Gly | Thr | Asn | Phe | Val | Asp | Arg | Leu | Pro | Gln | Ala | Val | Arg |     |
| 90  |     |     |     |     | 95  |     |     |     |     | 100 |     |     |     |     | 105 |     |

| | | | | | | | | | | | | | | | | |
| --- | --- | --- | --- | --- | --- | --- | --- | --- | --- | --- | --- | --- | --- | --- | --- | --- |
| aat | cgt | gtg | caa | gcg | ctt | aga | aac | att | caa | gat | gaa | tgt | gac | aag | gta | 628 |
| Asn | Arg | Val | Gln | Ala | Leu | Arg | Asn | Ile | Gln | Asp | Glu | Cys | Asp | Lys | Val |     |
|     |     |     |     | 110 |     |     |     |     | 115 |     |     |     |     | 120 |     |     |

| | | | | | | | | | | | | | | | | |
| --- | --- | --- | --- | --- | --- | --- | --- | --- | --- | --- | --- | --- | --- | --- | --- | --- |
| gat | acc | ctg | ttc | tta | aaa | gca | att | cat | gat | ctt | gaa | aga | aaa | tat | gct | 676 |
| Asp | Thr | Leu | Phe | Leu | Lys | Ala | Ile | His | Asp | Leu | Glu | Arg | Lys | Tyr | Ala |     |
|     |     |     |     | 125 |     |     |     |     | 130 |     |     |     |     | 135 |     |     |

| | | | | | | | | | | | | | | | | |
| --- | --- | --- | --- | --- | --- | --- | --- | --- | --- | --- | --- | --- | --- | --- | --- | --- |
| gaa | ctc | aac | aag | cct | ctg | tat | gat | agg | cgg | ttt | caa | atc | atc | aat | gca | 724 |
| Glu | Leu | Asn | Lys | Pro | Leu | Tyr | Asp | Arg | Arg | Phe | Gln | Ile | Ile | Asn | Ala |     |
|     |     |     | 140 |     |     |     |     | 145 |     |     |     |     | 150 |     |     |     |

| | | | | | | | | | | | | | | | | |
| --- | --- | --- | --- | --- | --- | --- | --- | --- | --- | --- | --- | --- | --- | --- | --- | --- |
| gaa | tac | gag | cct | aca | gaa | gaa | gaa | tgt | gaa | tgg | aat | tca | gag | gat | gag | 772 |
| Glu | Tyr | Glu | Pro | Thr | Glu | Glu | Glu | Cys | Glu | Trp | Asn | Ser | Glu | Asp | Glu |     |
|     | 155 |     |     |     |     | 160 |     |     |     |     | 165 |     |     |     |     |     |

| | | | | | | | | | | | | | | | | |
| --- | --- | --- | --- | --- | --- | --- | --- | --- | --- | --- | --- | --- | --- | --- | --- | --- |
| gag | ttc | agc | agt | gat | gag | gag | gtg | cag | gat | aac | acc | cct | agt | gaa | atg | 820 |
| Glu | Phe | Ser | Ser | Asp | Glu | Glu | Val | Gln | Asp | Asn | Thr | Pro | Ser | Glu | Met |     |
| 170 |     |     |     |     | 175 |     |     |     |     | 180 |     |     |     |     | 185 |     |

| | | | | | | | | | | | | | | | | |
| --- | --- | --- | --- | --- | --- | --- | --- | --- | --- | --- | --- | --- | --- | --- | --- | --- |
| cct | ccc | tta | gag | ggt | gag | gaa | gaa | gaa | aac | cct | aaa | gaa | aac | cca | gag | 868 |
| Pro | Pro | Leu | Glu | Gly | Glu | Glu | Glu | Glu | Asn | Pro | Lys | Glu | Asn | Pro | Glu |     |
|     |     |     |     | 190 |     |     |     |     | 195 |     |     |     |     | 200 |     |     |

| | | | | | | | | | | | | | | | | |
| --- | --- | --- | --- | --- | --- | --- | --- | --- | --- | --- | --- | --- | --- | --- | --- | --- |
| gtg | aaa | gct | gaa | gag | aag | gaa | gtt | cct | aaa | gaa | att | cct | gag | gtg | aag | 916 |
| Val | Lys | Ala | Glu | Glu | Lys | Glu | Val | Pro | Lys | Glu | Ile | Pro | Glu | Val | Lys |     |
|     |     |     | 205 |     |     |     |     | 210 |     |     |     |     | 215 |     |     |     |

| | | | | | | | | | | | | | | | | |
| --- | --- | --- | --- | --- | --- | --- | --- | --- | --- | --- | --- | --- | --- | --- | --- | --- |
| gat | gaa | gaa | aag | gaa | gtt | gct | aaa | gaa | att | cct | gag | gta | aag | gct | gaa | 964 |
| Asp | Glu | Glu | Lys | Glu | Val | Ala | Lys | Glu | Ile | Pro | Glu | Val | Lys | Ala | Glu |     |
|     |     | 220 |     |     |     |     | 225 |     |     |     |     | 230 |     |     |     |     |

| | | | | | | | | | | | | | | | | |
| --- | --- | --- | --- | --- | --- | --- | --- | --- | --- | --- | --- | --- | --- | --- | --- | --- |
| gaa | aaa | gca | gat | tct | aaa | gac | tgt | atg | gag | gca | acc | cct | gaa | gta | aaa | 1012 |
| Glu | Lys | Ala | Asp | Ser | Lys | Asp | Cys | Met | Glu | Ala | Thr | Pro | Glu | Val | Lys |     |
|     | 235 |     |     |     |     | 240 |     |     |     |     | 245 |     |     |     |     |     |

| | | | | | | | | | | | | | | | | |
| --- | --- | --- | --- | --- | --- | --- | --- | --- | --- | --- | --- | --- | --- | --- | --- | --- |
| gaa | gat | cct | aaa | gaa | gtc | ccc | cag | gta | aag | gca | gat | gat | aaa | gaa | cag | 1060 |
| Glu | Asp | Pro | Lys | Glu | Val | Pro | Gln | Val | Lys | Ala | Asp | Asp | Lys | Glu | Gln |     |
| 250 |     |     |     |     | 255 |     |     |     |     | 260 |     |     |     |     | 265 |     |

| | | | | | | | | | | | | | | | | |
| --- | --- | --- | --- | --- | --- | --- | --- | --- | --- | --- | --- | --- | --- | --- | --- | --- |
| cct | aaa | gca | aca | gag | gct | aag | gca | agg | gct | gca | gta | aga | gag | act | cat | 1108 |
| Pro | Lys | Ala | Thr | Glu | Ala | Lys | Ala | Arg | Ala | Ala | Val | Arg | Glu | Thr | His |     |
|     |     |     | 270 |     |     |     |     | 275 |     |     |     |     | 280 |     |     |     |

| | | | | | | | | | | | | | | | | |
| --- | --- | --- | --- | --- | --- | --- | --- | --- | --- | --- | --- | --- | --- | --- | --- | --- |
| aaa | aga | gtt | cct | gag | gaa | agg | ctt | cgg | gac | agt | gta | gat | ctt | aaa | aga | 1156 |
| Lys | Arg | Val | Pro | Glu | Glu | Arg | Leu | Arg | Asp | Ser | Val | Asp | Leu | Lys | Arg |     |
|     |     |     | 285 |     |     |     |     | 290 |     |     |     |     | 295 |     |     |     |

| | | | | | | | | | | | | | | | | |
| --- | --- | --- | --- | --- | --- | --- | --- | --- | --- | --- | --- | --- | --- | --- | --- | --- |
| gct | agg | aag | gga | aag | cct | aaa | aga | gaa | gac | cct | aaa | ggc | att | cct | gac | 1204 |
| Ala | Arg | Lys | Gly | Lys | Pro | Lys | Arg | Glu | Asp | Pro | Lys | Gly | Ile | Pro | Asp |     |
|     |     | 300 |     |     |     |     | 305 |     |     |     |     | 310 |     |     |     |     |

| | | | | | | | | | | | | | | | | |
| --- | --- | --- | --- | --- | --- | --- | --- | --- | --- | --- | --- | --- | --- | --- | --- | --- |
| tat | tgg | ctg | att | gtt | tta | aag | aat | gtt | gac | aag | ctc | ggg | cct | atg | att | 1252 |
| Tyr | Trp | Leu | Ile | Val | Leu | Lys | Asn | Val | Asp | Lys | Leu | Gly | Pro | Met | Ile |     |
|     | 315 |     |     |     |     | 320 |     |     |     |     | 325 |     |     |     |     |     |

| | | | | | | | | | | | | | | | | |
| --- | --- | --- | --- | --- | --- | --- | --- | --- | --- | --- | --- | --- | --- | --- | --- | --- |
| cag | aag | tat | gat | gag | ccc | att | ctg | aag | ttc | ttg | tcg | gat | gtt | agc | ctg | 1300 |
| Gln | Lys | Tyr | Asp | Glu | Pro | Ile | Leu | Lys | Phe | Leu | Ser | Asp | Val | Ser | Leu |     |
| 330 |     |     |     |     | 335 |     |     |     |     | 340 |     |     |     |     | 345 |     |

| | | | | | | | | | | | | | | | | |
| --- | --- | --- | --- | --- | --- | --- | --- | --- | --- | --- | --- | --- | --- | --- | --- | --- |
| aag | ttc | tca | aaa | cct | ggc | cag | cct | gta | agt | tac | acc | ttt | gaa | ttt | cat | 1348 |
| Lys | Phe | Ser | Lys | Pro | Gly | Gln | Pro | Val | Ser | Tyr | Thr | Phe | Glu | Phe | His |     |
|     |     |     |     | 350 |     |     |     |     | 355 |     |     |     |     | 360 |     |     |

| | | | | | | | | | | | | | | | | |
| --- | --- | --- | --- | --- | --- | --- | --- | --- | --- | --- | --- | --- | --- | --- | --- | --- |
| ttt | cta | ccc | aac | cca | tac | ttc | aga | aat | gag | gtg | ctg | gtg | aag | aca | tat | 1396 |
| Phe | Leu | Pro | Asn | Pro | Tyr | Phe | Arg | Asn | Glu | Val | Leu | Val | Lys | Thr | Tyr |     |
|     |     |     | 365 |     |     |     |     | 370 |     |     |     |     | 375 |     |     |     |

-continued

```
ata ata aag gca aaa cca gat cac aat gat ccc ttc ttt tct tgg gga      1444
Ile Ile Lys Ala Lys Pro Asp His Asn Asp Pro Phe Phe Ser Trp Gly
        380                 385                 390 tgg gaa att gaa gat tgc aaa ggc tgc aag ata gac cgg aga aga gga      1492
Trp Glu Ile Glu Asp Cys Lys Gly Cys Lys Ile Asp Arg Arg Arg Gly
395                 400                 405 aaa gat gtt act gtg aca act acc cag agt cgc aca act gct act gga      1540
Lys Asp Val Thr Val Thr Thr Thr Gln Ser Arg Thr Thr Ala Thr Gly
410                 415                 420                 425 gaa att gaa atc cag cca aga gtg gtt cct aat gca tca ttc ttc aac      1588
Glu Ile Glu Ile Gln Pro Arg Val Val Pro Asn Ala Ser Phe Phe Asn
                430                 435                 440 ttc ttt agt cct cct gag att cct atg att ggg aag ctg gaa cca cga      1636
Phe Phe Ser Pro Pro Glu Ile Pro Met Ile Gly Lys Leu Glu Pro Arg
            445                 450                 455 gaa gat gct atc ctg gat gag gac ttt gaa att ggg cag att tta cat      1684
Glu Asp Ala Ile Leu Asp Glu Asp Phe Glu Ile Gly Gln Ile Leu His
        460                 465                 470 gat aat gtc atc ctg aaa tca atc tat tac tat act gga gaa gtc aat      1732
Asp Asn Val Ile Leu Lys Ser Ile Tyr Tyr Tyr Thr Gly Glu Val Asn
475                 480                 485 ggt acc tac tat caa ttt ggc aaa cat tat gga aac aag aaa tac aga      1780
Gly Thr Tyr Tyr Gln Phe Gly Lys His Tyr Gly Asn Lys Lys Tyr Arg
490                 495                 500                 505 aaa taagtcaatc tgaaagattt ttcaagaatc ttaaaatctc aagaagtgaa           1833
Lys gcagattcat acagccttga aaaaagtaaa accctgacct gtaacctgaa cactattatt   1893
ccttatagtc aagttttgt ggtttcttgg tagtctatat tttaaaaata gtcctaaaaa    1953
gtgtctaagt gccagtttat tctatctagg ctgttgtagt ataatattct tcaaaatatg   2013
taagctgttg tcaattatct aaagcatgtt agtttggtgc tacacagtgt tgattttgt    2073 gatgtccttt ggtcatgttt ctgttagact gtagctgtga aactgtcaga attgttaact   2133
gaaacaaata tttgcttgaa aaaaaaagtt catgaagtac caatgcaagt gttttatttt   2193
ttttcttttt tccagcccat aagactaagg gtttaaatct gcttgcacta gctgtgcctt   2253
cattagtttg ctatagaaat ccagtactta tagtaaataa aacagtgtat tttgaagttt   2313
gactgcttga aaaagattag catacatcta atgtgaaaag accacatttg attcaactga   2373
gaccttgtgt atgtgacata tagtggccta taaatttaat cataatgatg ttattgttta   2433
ccactgaggt gttaatataa catagtattt ttgaaaaagt ttcttcatct tatattgtgt   2493
aattgtaaac taaagatacc gtgttttctt tgtattgtgt tctaccttcc ctttcactga   2553
aaatgatcac ttcatttgat actgtttttc atgttcttgt attgcaacct aaaataaata   2613
aatattaaag tgtgttatac tat                                           2636

<210> SEQ ID NO 22
<211> LENGTH: 170
<212> TYPE: PRT
<213> ORGANISM: Homo sapiens

<400> SEQUENCE: 22

Met Thr Glu Leu Gln Ser Ala Leu Leu Leu Arg Arg Gln Leu Ala Glu
 1               5                  10                  15

Leu Asn Lys Asn Pro Val Glu Gly Phe Ser Ala Gly Leu Ile Asp Asp
                20                  25                  30

Asn Asp Leu Tyr Arg Trp Glu Val Leu Ile Ile Gly Pro Pro Asp Thr
            35                  40                  45
```

Leu Tyr Glu Gly Gly Val Phe Lys Ala His Leu Thr Phe Pro Lys Asp
            50                  55                  60

Tyr Pro Leu Arg Pro Pro Lys Met Lys Phe Ile Thr Glu Ile Trp His
 65                  70                  75                  80

Pro Asn Val Asp Lys Asn Gly Asp Val Cys Ile Ser Ile Leu His Glu
                 85                  90                  95

Pro Gly Glu Asp Lys Tyr Gly Tyr Lys Pro Glu Gly Arg Trp Leu
                100                 105                 110

Pro Ile His Thr Val Glu Thr Ile Met Ile Ser Val Ile Ser Met Leu
            115                 120                 125

Ala Asp Pro Asn Gly Asp Ser Pro Ala Asn Val Asp Ala Ala Lys Glu
130                 135                 140

Trp Arg Glu Asp Arg Asn Gly Glu Phe Lys Arg Lys Val Ala Arg Cys
145                 150                 155                 160

Val Arg Lys Ser Gln Glu Thr Ala Phe Glu
                165                 170

<210> SEQ ID NO 23
<211> LENGTH: 510
<212> TYPE: DNA
<213> ORGANISM: Homo sapiens

<400> SEQUENCE: 23

```
atgacggagc tgcagtcggc actgctactg cgaagacagc tggcagaact caacaaaaat      60
ccagtggaag cttttctgc aggtttaata gatgacaatg atctctaccg atgggaagtc     120
cttattattg gccctccaga tacactttat gaaggtggtg ttttttaaggc tcatcttact     180 ttcccaaaag attatcccct ccgacctcct aaaatgaaat tcattacaga aatctggcac     240
ccaaatgttg ataaaaatgg tgatgtgtgc atttctattc ttcatgagcc tggggaagat     300
aagtatggtt atgaaaagcc agaggaacgc tggctcccta ccacactgt ggaaaccatc      360 atgattagtg tcatttctat gctggcagac cctaatggag actcacctgc taatgttgat     420
gctgcgaaag aatggaggga agatagaaat ggagaattta aagaaaagt tgcccgctgt      480 gtaagaaaaa gccaagagac tgcttttgag                                      510
```

<210> SEQ ID NO 24
<211> LENGTH: 617
<212> TYPE: DNA
<213> ORGANISM: Homo sapiens
<220> FEATURE:
<221> NAME/KEY: CDS
<222> LOCATION: (19)..(528)

<400> SEQUENCE: 24
gggccctcgg cagggagg atg acg gag ctg cag tcg gca ctg cta ctg cga    51
                    Met Thr Glu Leu Gln Ser Ala Leu Leu Leu Arg
                     1               5                  10 aga cag ctg gca gaa ctc aac aaa aat cca gtg gaa ggc ttt tct gca    99
Arg Gln Leu Ala Glu Leu Asn Lys Asn Pro Val Glu Gly Phe Ser Ala
             15                  20                  25 ggt tta ata gat gac aat gat ctc tac cga tgg gaa gtc ctt att att   147
Gly Leu Ile Asp Asp Asn Asp Leu Tyr Arg Trp Glu Val Leu Ile Ile
         30                  35                  40 ggc cct cca gat aca ctt tat gaa ggt ggt gtt ttt aag gct cat ctt   195
Gly Pro Pro Asp Thr Leu Tyr Glu Gly Gly Val Phe Lys Ala His Leu
     45                  50                  55 act ttc cca aaa gat tat ccc ctc cga cct cct aaa atg aaa ttc att   243
Thr Phe Pro Lys Asp Tyr Pro Leu Arg Pro Pro Lys Met Lys Phe Ile

```
                   60                  65                  70                  75
aca gaa atc tgg cac cca aat gtt gat aaa aat ggt gat gtg tgc att        291
Thr Glu Ile Trp His Pro Asn Val Asp Lys Asn Gly Asp Val Cys Ile
                    80                  85                  90 tct att ctt cat gag cct ggg gaa gat aag tat ggt tat gaa aag cca        339
Ser Ile Leu His Glu Pro Gly Glu Asp Lys Tyr Gly Tyr Glu Lys Pro
             95                 100                 105 gag gaa cgc tgg ctc cct atc cac act gtg gaa acc atc atg att agt        387
Glu Glu Arg Trp Leu Pro Ile His Thr Val Glu Thr Ile Met Ile Ser
        110                 115                 120 gtc att tct atg ctg gca gac cct aat gga gac tca cct gct aat gtt        435
Val Ile Ser Met Leu Ala Asp Pro Asn Gly Asp Ser Pro Ala Asn Val
    125                 130                 135 gat gct gcg aaa gaa tgg agg gaa gat aga aat gga gaa ttt aaa aga        483
Asp Ala Ala Lys Glu Trp Arg Glu Asp Arg Asn Gly Glu Phe Lys Arg
140                 145                 150                 155 aaa gtt gcc cgc tgt gta aga aaa agc caa gag act gct ttt gag            528
Lys Val Ala Arg Cys Val Arg Lys Ser Gln Glu Thr Ala Phe Glu
                160                 165                 170 tgacatttat ttagcagcta gtaacttcac ttatttcagg gtctccaatt gagaaacatg      588
gcactgtttt tcctgcactc tacccaccg                                        617

<210> SEQ ID NO 25
<211> LENGTH: 374
<212> TYPE: PRT
<213> ORGANISM: Homo sapiens

<400> SEQUENCE: 25

Met Val Leu Trp Glu Ser Pro Arg Gln Cys Ser Ser Trp Thr Leu Cys
 1               5                  10                  15

Glu Gly Phe Cys Trp Leu Leu Leu Pro Val Met Leu Leu Ile Val
                20                  25                  30

Ala Arg Pro Val Lys Leu Ala Ala Phe Pro Thr Ser Leu Ser Asp Cys
            35                  40                  45

Gln Thr Pro Thr Gly Trp Asn Cys Ser Gly Tyr Asp Asp Arg Glu Asn
        50                  55                  60

Asp Leu Phe Leu Cys Asp Thr Asn Thr Cys Lys Phe Asp Gly Glu Cys
65                  70                  75                  80

Leu Arg Ile Gly Asp Thr Val Thr Cys Val Cys Gln Phe Lys Cys Asn
                85                  90                  95

Asn Asp Tyr Val Pro Val Cys Gly Ser Asn Gly Glu Ser Tyr Gln Asn
            100                 105                 110

Glu Cys Tyr Leu Arg Gln Ala Ala Cys Lys Gln Gln Ser Glu Ile Leu
        115                 120                 125

Val Val Ser Glu Gly Ser Cys Ala Thr Asp Ala Gly Ser Gly Ser Gly
    130                 135                 140

Asp Gly Val His Glu Gly Ser Gly Glu Thr Ser Gln Lys Glu Thr Ser
145                 150                 155                 160

Thr Cys Asp Ile Cys Gln Phe Gly Ala Glu Cys Asp Glu Asp Ala Glu
                165                 170                 175

Asp Val Trp Cys Val Cys Asn Ile Asp Cys Ser Gln Thr Asn Phe Asn
            180                 185                 190

Pro Leu Cys Ala Ser Asp Gly Lys Ser Tyr Asp Asn Ala Cys Gln Ile
        195                 200                 205

Lys Glu Ala Ser Cys Gln Lys Gln Glu Lys Ile Glu Val Met Ser Leu
    210                 215                 220
```

-continued

| | | | | | | | | | | | | | | |
|---|---|---|---|---|---|---|---|---|---|---|---|---|---|---|
| Gly | Arg | Cys | Gln | Asp | Asn | Thr | Thr | Thr | Thr | Lys | Ser | Glu | Asp | Gly |
| 225 | | | | | 230 | | | | 235 | | | | | 240 |
| His | Tyr | Ala | Arg | Thr | Asp | Tyr | Ala | Glu | Asn | Ala | Asn | Lys | Leu | Glu | Glu |
| | | | | 245 | | | | | 250 | | | | | 255 | |
| Ser | Ala | Arg | Glu | His | His | Ile | Pro | Cys | Pro | Glu | His | Tyr | Asn | Gly | Phe |
| | | | 260 | | | | | 265 | | | | | 270 | | |
| Cys | Met | His | Gly | Lys | Cys | Glu | His | Ser | Ile | Asn | Met | Gln | Glu | Pro | Ser |
| | | 275 | | | | | 280 | | | | | 285 | | | |
| Cys | Arg | Cys | Asp | Ala | Gly | Tyr | Thr | Gly | Gln | His | Cys | Glu | Lys | Lys | Asp |
| | 290 | | | | | 295 | | | | | 300 | | | | |
| Tyr | Ser | Val | Leu | Tyr | Val | Val | Pro | Gly | Pro | Val | Arg | Phe | Gln | Tyr | Val |
| 305 | | | | | 310 | | | | | 315 | | | | | 320 |
| Leu | Ile | Ala | Ala | Val | Ile | Gly | Thr | Ile | Gln | Ile | Ala | Val | Ile | Cys | Val |
| | | | | 325 | | | | | 330 | | | | | 335 | |
| Val | Val | Leu | Cys | Ile | Thr | Arg | Lys | Cys | Pro | Arg | Ser | Asn | Arg | Ile | His |
| | | | 340 | | | | | 345 | | | | | 350 | | |
| Arg | Gln | Lys | Gln | Asn | Thr | Gly | His | Tyr | Ser | Ser | Asp | Asn | Thr | Thr | Arg |
| | | 355 | | | | | 360 | | | | | 365 | | | |
| Ala | Ser | Thr | Arg | Leu | Ile | | | | | | | | | | |
| | 370 | | | | | | | | | | | | | | |

<210> SEQ ID NO 26
<211> LENGTH: 1122
<212> TYPE: DNA
<213> ORGANISM: Homo sapiens

<400> SEQUENCE: 26

```
atggtgctgt gggagtcccc gcggcagtgc agcagctgga cactttgcga gggcttttgc      60
tggctgctgc tgctgcccgt catgctactc atcgtagccc gcccggtgaa gctcgctgct     120
ttccctacct ccttaagtga ctgccaaacg cccaccggct ggaattgctc tggttatgat     180
gacagagaaa atgatctctt cctctgtgac accaacacct gtaaatttga tgggaatgt      240
ttaagaattg agacactgt gacttgcgtc tgtcagttca agtgcaacaa tgactatgtg      300
cctgtgtgtg gctccaatgg ggagagctac cagaatgagt gttacctgcg acaggctgca    360
tgcaaacagc agagtgagat acttgtggtg tcagaaggat catgtgccac agatgcagga    420
tcaggatctg gagatggagt ccatgaaggc tctggagaaa ctagtcaaaa ggagacatcc    480
acctgtgata tttgccagtt tggtgcagaa tgtgacgaag atgccgagga tgtctggtgt    540
gtgtgtaata ttgactgttc tcaaaccaac ttcaatcccc tctgcgcttc tgatgggaaa    600
tcttatgata atgcatgcca aatcaaagaa gcatcgtgtc agaaacagga gaaaattgaa    660
gtcatgtctt tgggtcgatg tcaagataac acaactacaa ctactaagtc tgaagatggg    720
cattatgcaa gaacagatta tgcagagaat gctaacaaat tagaagaaag tgccagagaa    780
caccacatac cttgtccgga acattacaat ggcttctgca tgcatgggaa gtgtgagcat    840
tctatcaata tgcaggagcc atcttgcagg tgtgatgctg ttatactgg acaacactgt     900
gaaaaaaagg actacagtgt tctatacgtt gttcccggtc ctgtacgatt tcagtatgtc    960
ttaatcgcag ctgtgattgg aacaattcag attgctgtca tctgtgtggt ggtcctctgc   1020
atcacaagga aatgccccag aagcaacaga attcacagac agaagcaaaa tacagggcac   1080
tacagttcag acaatacaac aagagcgtcc acgaggttaa tc                      1122
```

<210> SEQ ID NO 27
<211> LENGTH: 1721
<212> TYPE: DNA

```
<213> ORGANISM: Homo sapiens
<220> FEATURE:
<221> NAME/KEY: CDS
<222> LOCATION: (368)..(1489)

<400> SEQUENCE: 27
ctgcggggcg ccttgactct ccctccaccc tgcctcctcg ggctccactc gtctgcccct      60
ggactcccgt ctcctcctgt cctccggctt cccagagctc cctccttatg gcagcagctt     120
cccgcgtctc cggcgcagct tctcagcgga cgaccctctc gctccggggc tgagccagtc     180
cctggatgtt gctgaaactc tcgagatcat gcgcgggttt ggctgctgct tcccgccgg      240 gtgccactgc caccgccgcc gcctctgctg ccgccgtccg cgggatgctc agtagcccgc     300 tgccggccc ccgcgatcct gtgttcctcg gaagccgttt gctgctgcag agttgcacga     360
```

| | | | | | | | | | | | | |
|---|---|---|---|---|---|---|---|---|---|---|---|---|
| actagtc | atg | gtg | ctg | tgg | gag | tcc | ccg | cgg | cag | tgc | agc | agc tgg aca | 409 |
| | Met | Val | Leu | Trp | Glu | Ser | Pro | Arg | Gln | Cys | Ser | Ser Trp Thr | |
| | 1 | | | 5 | | | | | 10 | | | | |

| ctt | tgc | gag | ggc | ttt | tgc | tgg | ctg | ctg | ctg | ccc | gtc | atg | cta | ctc | 457 |
|---|---|---|---|---|---|---|---|---|---|---|---|---|---|---|---|
| Leu | Cys | Glu | Gly | Phe | Cys | Trp | Leu | Leu | Leu | Pro | Val | Met | Leu | Leu | |
| 15 | | | | 20 | | | | | 25 | | | | | 30 | |

| atc | gta | gcc | cgc | ccg | gtg | aag | ctc | gct | gct | ttc | cct | acc | tcc | tta | agt | 505 |
|---|---|---|---|---|---|---|---|---|---|---|---|---|---|---|---|---|
| Ile | Val | Ala | Arg | Pro | Val | Lys | Leu | Ala | Ala | Phe | Pro | Thr | Ser | Leu | Ser | |
| | | | 35 | | | | | 40 | | | | | 45 | | | |

| gac | tgc | caa | acg | ccc | acc | ggc | tgg | aat | tgc | tct | ggt | tat | gat | gac | aga | 553 |
|---|---|---|---|---|---|---|---|---|---|---|---|---|---|---|---|---|
| Asp | Cys | Gln | Thr | Pro | Thr | Gly | Trp | Asn | Cys | Ser | Gly | Tyr | Asp | Asp | Arg | |
| | | 50 | | | | | 55 | | | | | 60 | | | | |

| gaa | aat | gat | ctc | ttc | ctc | tgt | gac | acc | aac | acc | tgt | aaa | ttt | gat | ggg | 601 |
|---|---|---|---|---|---|---|---|---|---|---|---|---|---|---|---|---|
| Glu | Asn | Asp | Leu | Phe | Leu | Cys | Asp | Thr | Asn | Thr | Cys | Lys | Phe | Asp | Gly | |
| 65 | | | | | 70 | | | | | 75 | | | | | | |

| gaa | tgt | tta | aga | att | gga | gac | act | gtg | act | tgc | gtc | tgt | cag | ttc | aag | 649 |
|---|---|---|---|---|---|---|---|---|---|---|---|---|---|---|---|---|
| Glu | Cys | Leu | Arg | Ile | Gly | Asp | Thr | Val | Thr | Cys | Val | Cys | Gln | Phe | Lys | |
| 80 | | | | 85 | | | | | 90 | | | | | | | |

| tgc | aac | aat | gac | tat | gtg | cct | gtg | tgt | ggc | tcc | aat | ggg | gag | agc | tac | 697 |
|---|---|---|---|---|---|---|---|---|---|---|---|---|---|---|---|---|
| Cys | Asn | Asn | Asp | Tyr | Val | Pro | Val | Cys | Gly | Ser | Asn | Gly | Glu | Ser | Tyr | |
| 95 | | | | 100 | | | | | 105 | | | | | 110 | | |

| cag | aat | gag | tgt | tac | ctg | cga | cag | gct | gca | tgc | aaa | cag | cag | agt | gag | 745 |
|---|---|---|---|---|---|---|---|---|---|---|---|---|---|---|---|---|
| Gln | Asn | Glu | Cys | Tyr | Leu | Arg | Gln | Ala | Ala | Cys | Lys | Gln | Gln | Ser | Glu | |
| | | | 115 | | | | | 120 | | | | | 125 | | | |

| ata | ctt | gtg | gtg | tca | gaa | gga | tca | tgt | gcc | aca | gat | gca | gga | tca | gga | 793 |
|---|---|---|---|---|---|---|---|---|---|---|---|---|---|---|---|---|
| Ile | Leu | Val | Val | Ser | Glu | Gly | Ser | Cys | Ala | Thr | Asp | Ala | Gly | Ser | Gly | |
| | | | 130 | | | | | 135 | | | | | 140 | | | |

| tct | gga | gat | gga | gtc | cat | gaa | ggc | tct | gga | gaa | act | agt | caa | aag | gag | 841 |
|---|---|---|---|---|---|---|---|---|---|---|---|---|---|---|---|---|
| Ser | Gly | Asp | Gly | Val | His | Glu | Gly | Ser | Gly | Glu | Thr | Ser | Gln | Lys | Glu | |
| | | 145 | | | | | 150 | | | | | 155 | | | | |

| aca | tcc | acc | tgt | gat | att | tgc | cag | ttt | ggt | gca | gaa | tgt | gac | gaa | gat | 889 |
|---|---|---|---|---|---|---|---|---|---|---|---|---|---|---|---|---|
| Thr | Ser | Thr | Cys | Asp | Ile | Cys | Gln | Phe | Gly | Ala | Glu | Cys | Asp | Glu | Asp | |
| 160 | | | | | 165 | | | | | 170 | | | | | | |

| gcc | gag | gat | gtc | tgg | tgt | gtg | tgt | aat | att | gac | tgt | tct | caa | acc | aac | 937 |
|---|---|---|---|---|---|---|---|---|---|---|---|---|---|---|---|---|
| Ala | Glu | Asp | Val | Trp | Cys | Val | Cys | Asn | Ile | Asp | Cys | Ser | Gln | Thr | Asn | |
| 175 | | | | 180 | | | | | 185 | | | | | 190 | | |

| ttc | aat | ccc | ctc | tgc | gct | tct | gat | ggg | aaa | tct | tat | gat | aat | gca | tgc | 985 |
|---|---|---|---|---|---|---|---|---|---|---|---|---|---|---|---|---|
| Phe | Asn | Pro | Leu | Cys | Ala | Ser | Asp | Gly | Lys | Ser | Tyr | Asp | Asn | Ala | Cys | |
| | | | 195 | | | | | 200 | | | | | 205 | | | |

| caa | atc | aaa | gaa | gca | tcg | tgt | cag | aaa | cag | gag | aaa | att | gaa | gtc | atg | 1033 |
|---|---|---|---|---|---|---|---|---|---|---|---|---|---|---|---|---|
| Gln | Ile | Lys | Glu | Ala | Ser | Cys | Gln | Lys | Gln | Glu | Lys | Ile | Glu | Val | Met | |
| | | 210 | | | | | 215 | | | | | 220 | | | | |

| tct | ttg | ggt | cga | tgt | caa | gat | aac | aca | act | aca | act | aag | tct | gaa | | 1081 |
|---|---|---|---|---|---|---|---|---|---|---|---|---|---|---|---|---|
| Ser | Leu | Gly | Arg | Cys | Gln | Asp | Asn | Thr | Thr | Thr | Thr | Lys | Ser | Glu | | |
| 225 | | | | | 230 | | | | | 235 | | | | | | |

| gat | ggg | cat | tat | gca | aga | aca | gat | tat | gca | gag | aat | gct | aac | aaa | tta | 1129 |
|---|---|---|---|---|---|---|---|---|---|---|---|---|---|---|---|---|

-continued

| | | | | | | | | | | | | | | |
|---|---|---|---|---|---|---|---|---|---|---|---|---|---|---|
|Asp|Gly|His|Tyr|Ala|Arg|Thr|Asp|Tyr|Ala|Glu|Asn|Ala|Asn|Lys|Leu|
| |240| | | |245| | | |250| | | | | | |

```
gaa gaa agt gcc aga gaa cac cac ata cct tgt ccg gaa cat tac aat    1177
Glu Glu Ser Ala Arg Glu His His Ile Pro Cys Pro Glu His Tyr Asn
255             260                 265                 270 ggc ttc tgc atg cat ggg aag tgt gag cat tct atc aat atg cag gag    1225
Gly Phe Cys Met His Gly Lys Cys Glu His Ser Ile Asn Met Gln Glu
            275                 280                 285 cca tct tgc agg tgt gat gct ggt tat act gga caa cac tgt gaa aaa    1273
Pro Ser Cys Arg Cys Asp Ala Gly Tyr Thr Gly Gln His Cys Glu Lys
        290                 295                 300 aag gac tac agt gtt cta tac gtt gtt ccc ggt cct gta cga ttt cag    1321
Lys Asp Tyr Ser Val Leu Tyr Val Val Pro Gly Pro Val Arg Phe Gln
    305                 310                 315 tat gtc tta atc gca gct gtg att gga aca att cag att gct gtc atc    1369
Tyr Val Leu Ile Ala Ala Val Ile Gly Thr Ile Gln Ile Ala Val Ile
320                 325                 330 tgt gtg gtg gtc ctc tgc atc aca agg aaa tgc ccc aga agc aac aga    1417
Cys Val Val Val Leu Cys Ile Thr Arg Lys Cys Pro Arg Ser Asn Arg
335                 340                 345                 350 att cac aga cag aag caa aat aca ggg cac tac agt tca gac aat aca    1465
Ile His Arg Gln Lys Gln Asn Thr Gly His Tyr Ser Ser Asp Asn Thr
                355                 360                 365 aca aga gcg tcc acg agg tta atc taaagggagc atgtttcaca gtggctggac   1519
Thr Arg Ala Ser Thr Arg Leu Ile
                370 taccgagagc ttggactaca caatacagta ttatagacaa agaataaga caagagatct   1579 acacatgttg ccttgcattt gtggtaatct acaccaatga aacatgtac tacagctata   1639 tttgattatg tatggatata tttgaaatag tatacattgt cttgatgttt tttctgtaat  1699 gtaaataaac tatttatatc ac                                          1721
```

<210> SEQ ID NO 28
<211> LENGTH: 817
<212> TYPE: PRT
<213> ORGANISM: Homo sapiens

<400> SEQUENCE: 28

| | | | | | | | | | | | | | | |
|---|---|---|---|---|---|---|---|---|---|---|---|---|---|---|---|
|Met|Gly|Asp|Thr|Val|Val|Glu|Pro|Ala|Pro|Leu|Lys|Pro|Thr|Ser|Glu|
|1| | | |5| | | | |10| | | | |15| |

| | | | | | | | | | | | | | | |
|---|---|---|---|---|---|---|---|---|---|---|---|---|---|---|---|
|Pro|Thr|Ser|Gly|Pro|Pro|Gly|Asn|Asn|Gly|Gly|Ser|Leu|Leu|Ser|Val|
| | | |20| | | | |25| | | | |30| | |

| | | | | | | | | | | | | | | |
|---|---|---|---|---|---|---|---|---|---|---|---|---|---|---|---|
|Ile|Thr|Glu|Gly|Val|Gly|Glu|Leu|Ser|Val|Ile|Asp|Pro|Glu|Val|Ala|
| | | |35| | | | |40| | | | |45| | |

| | | | | | | | | | | | | | | |
|---|---|---|---|---|---|---|---|---|---|---|---|---|---|---|---|
|Gln|Lys|Ala|Cys|Gln|Glu|Val|Leu|Glu|Lys|Val|Lys|Leu|Leu|His|Gly|
| | |50| | | | |55| | | | |60| | | |

| | | | | | | | | | | | | | | |
|---|---|---|---|---|---|---|---|---|---|---|---|---|---|---|---|
|Gly|Val|Ala|Val|Ser|Ser|Arg|Gly|Thr|Pro|Leu|Glu|Leu|Val|Asn|Gly|
|65| | | | |70| | | | |75| | | | |80|

| | | | | | | | | | | | | | | |
|---|---|---|---|---|---|---|---|---|---|---|---|---|---|---|---|
|Asp|Gly|Val|Asp|Ser|Glu|Ile|Arg|Cys|Leu|Asp|Asp|Pro|Pro|Ala|Gln|
| | | | |85| | | | |90| | | | |95| |

| | | | | | | | | | | | | | | |
|---|---|---|---|---|---|---|---|---|---|---|---|---|---|---|---|
|Ile|Arg|Glu|Glu|Glu|Asp|Glu|Met|Gly|Ala|Ala|Val|Ala|Ser|Gly|Thr|
| | | | |100| | | | |105| | | | |110| |

| | | | | | | | | | | | | | | |
|---|---|---|---|---|---|---|---|---|---|---|---|---|---|---|---|
|Ala|Lys|Gly|Ala|Arg|Arg|Arg|Arg|Gln|Asn|Asn|Ser|Ala|Lys|Gln|Ser|
| | | |115| | | | |120| | | | |125| | |

| | | | | | | | | | | | | | | |
|---|---|---|---|---|---|---|---|---|---|---|---|---|---|---|---|
|Trp|Leu|Leu|Arg|Leu|Phe|Glu|Ser|Lys|Leu|Phe|Asp|Ile|Ser|Met|Ala|
| | |130| | | | |135| | | | |140| | | |

| | | | | | | | | | | | | | | |
|---|---|---|---|---|---|---|---|---|---|---|---|---|---|---|---|
|Ile|Ser|Tyr|Leu|Tyr|Asn|Ser|Lys|Glu|Pro|Gly|Val|Gln|Ala|Tyr|Ile|
|145| | | | |150| | | | |155| | | | |160|

```
Gly Asn Arg Leu Phe Cys Phe Arg Asn Glu Asp Val Asp Phe Tyr Leu
                165                 170                 175

Pro Gln Leu Leu Asn Met Tyr Ile His Met Asp Glu Asp Val Gly Asp
            180                 185                 190

Ala Ile Lys Pro Tyr Ile Val His Arg Cys Arg Gln Ser Ile Asn Phe
        195                 200                 205

Ser Leu Gln Cys Ala Leu Leu Leu Gly Ala Tyr Ser Ser Asp Met His
    210                 215                 220

Ile Ser Thr Gln Arg His Ser Arg Gly Thr Lys Leu Arg Lys Leu Ile
225                 230                 235                 240

Leu Ser Asp Glu Leu Lys Pro Ala His Arg Lys Arg Glu Leu Pro Ser
                245                 250                 255

Leu Ser Pro Ala Pro Asp Thr Gly Leu Ser Pro Ser Lys Arg Thr His
            260                 265                 270

Gln Arg Ser Lys Ser Asp Ala Thr Ala Ser Ile Ser Leu Ser Ser Asn
        275                 280                 285

Leu Lys Arg Thr Ala Ser Asn Pro Lys Val Glu Asn Glu Asp Glu Glu
    290                 295                 300

Leu Ser Ser Thr Glu Ser Ile Asp Asn Ser Phe Ser Ser Pro Val
305                 310                 315                 320

Arg Leu Ala Pro Glu Arg Glu Phe Ile Lys Ser Leu Met Ala Ile Gly
                325                 330                 335

Lys Arg Leu Ala Thr Leu Pro Thr Lys Glu Gln Lys Thr Gln Arg Leu
            340                 345                 350

Ile Ser Glu Leu Ser Leu Leu Asn His Lys Leu Pro Ala Arg Val Trp
        355                 360                 365

Leu Pro Thr Ala Gly Phe Asp His His Val Val Arg Val Pro His Thr
    370                 375                 380

Gln Ala Val Val Leu Asn Ser Lys Asp Lys Ala Pro Tyr Leu Ile Tyr
385                 390                 395                 400

Val Glu Val Leu Glu Cys Glu Asn Phe Asp Thr Thr Ser Val Pro Ala
                405                 410                 415

Arg Ile Pro Glu Asn Arg Ile Arg Ser Thr Arg Ser Val Glu Asn Leu
            420                 425                 430

Pro Glu Cys Gly Ile Thr His Glu Gln Arg Ala Gly Ser Phe Ser Thr
        435                 440                 445

Val Pro Asn Tyr Asp Asn Asp Asp Glu Ala Trp Ser Val Asp Asp Ile
    450                 455                 460

Gly Glu Leu Gln Val Glu Leu Pro Glu Val His Thr Asn Ser Cys Asp
465                 470                 475                 480

Asn Ile Ser Gln Phe Ser Val Asp Ser Ile Thr Ser Gln Glu Ser Lys
                485                 490                 495

Glu Pro Val Phe Ile Ala Ala Gly Asp Ile Arg Arg Arg Leu Ser Glu
            500                 505                 510

Gln Leu Ala His Thr Pro Thr Ala Phe Lys Arg Asp Pro Glu Asp Pro
        515                 520                 525

Ser Ala Val Ala Leu Lys Glu Pro Trp Gln Glu Lys Val Arg Arg Ile
    530                 535                 540

Arg Glu Gly Ser Pro Tyr Gly His Leu Pro Asn Trp Arg Leu Leu Ser
545                 550                 555                 560

Val Ile Val Lys Cys Gly Asp Asp Leu Arg Gln Glu Leu Leu Ala Phe
                565                 570                 575

Gln Val Leu Lys Gln Leu Gln Ser Ile Trp Glu Gln Glu Arg Val Pro
```

```
                        580             585               590
Leu Trp Ile Lys Pro Ile Gln Asp Ser Cys Glu Ile Thr Thr Asp Ser
                595                 600                 605
Gly Met Ile Glu Pro Val Val Asn Ala Val Ser Ile His Gln Val Lys
        610                 615                 620
Lys Gln Ser Gln Leu Ser Leu Leu Asp Tyr Phe Leu Gln Glu His Gly
625                 630                 635                 640
Ser Tyr Thr Thr Glu Ala Phe Leu Ser Ala Gln Arg Asn Phe Val Gln
                645                 650                 655
Ser Cys Ala Gly Tyr Cys Leu Val Cys Tyr Leu Leu Gln Val Lys Asp
            660                 665                 670
Arg His Asn Gly Asn Ile Leu Leu Asp Ala Glu Gly His Ile Ile His
                675                 680                 685
Ile Asp Phe Gly Phe Ile Leu Ser Ser Ser Pro Arg Asn Leu Gly Phe
            690                 695                 700
Glu Thr Ser Ala Phe Lys Leu Thr Thr Glu Phe Val Asp Val Met Gly
705                 710                 715                 720
Gly Leu Asp Gly Asp Met Phe Asn Tyr Tyr Lys Met Leu Met Leu Gln
                725                 730                 735
Gly Leu Ile Ala Ala Arg Lys His Met Asp Lys Val Val Gln Ile Val
            740                 745                 750
Glu Ile Met Gln Gln Gly Ser Gln Leu Pro Cys Phe His Gly Ser Ser
                755                 760                 765
Thr Ile Arg Asn Leu Lys Glu Arg Phe His Met Ser Met Thr Glu Glu
    770                 775                 780
Gln Leu Gln Leu Leu Val Glu Gln Met Val Asp Gly Ser Met Arg Ser
785                 790                 795                 800
Ile Thr Thr Lys Leu Tyr Asp Gly Phe Gln Tyr Leu Thr Asn Gly Ile
                805                 810                 815
Met

<210> SEQ ID NO 29
<211> LENGTH: 2451
<212> TYPE: DNA
<213> ORGANISM: Homo sapiens

<400> SEQUENCE: 29
atgggagata cagtagtgga gcctgccccc ttgaagccaa cttctgagcc cacttctggc    60
ccaccaggga ataatggggg gtccctgcta agtgtcatca cggagggggt cgggaactca   120
tcagtgattg accctgaggt ggcccagaag gcctgccagg aggtgttgga gaaagtcaag   180
cttttgcatg gaggcgtggc agtctctagc agaggcaccc cactggagtt ggtcaatggg   240
gatggtgtgg acagtgagat ccgttgccta gatgatccac ctgcccagat caggaggag   300 gaagatgaga tggggccgc tgtggcctca ggcacagcca aggagcaag aagacgcgg    360 cagaacaact cagctaaaca gtcttggctg ctgaggctgt ttgagtcaaa actgtttgac   420
atctccatgg ccatttcata cctgtataac tccaaggagc tggagtaca agcctacatt   480 ggcaaccggc tcttctgctt cgcaacgag acgtggact tctatctgcc ccagttgctt   540
aacatgtaca tccacatgga tgaggacgtg ggtgatgcca ttaagcccta catagtccac   600
cgttgccgcc agagcattaa cttttcctc cagtgtgccc tgttgcttgg ggcctattct   660
tcagacatgc acatttccac tcaacgacac tcccgtggga ccaagctacg gaagctgatc   720
ctctcagatg agctaaagcc agctcacagg aagagggagc tgcctccctt gagcccggc   780
```

```
cctgatacag ggctgtctcc ctccaaaagg actcaccagc gctctaagtc agatgccact    840
gccagcataa gtctcagcag caacctgaaa cgaacagcca gcaaccctaa agtggagaat    900
gaggatgagg agctctcctc cagcaccgag agtattgata attcattcag ttcccctgtt    960
cgactggctc ctgagagaga attcatcaag tccctgatgg cgatcggcaa gcggctggcc   1020
acgctcccca ccaaagagca gaaaacacag aggctgatct cagagctctc cctgctcaac   1080
cataagctcc ctgcccgagt ctggctgccc actgctggct tgaccaccac cgtggtccgt   1140
gtaccccaca cacaggctgt tgtcctcaac tccaaggaca aggctcccta cctgatttat   1200
gtggaagtcc ttgaatgtga aaactttgac accaccagtg tccctgcccg gatccccgag   1260
aaccgaattc ggagtacgag gtccgtagaa aacttgcccg aatgtggtat tacccatgag   1320
cagcgagctg gcagcttcag cactgtgccc aactatgaca cgatgatga ggcctggtcg    1380 gtggatgaca taggcgagct gcaagtggag ctccccgaag tgcataccaa cagctgtgac   1440
aacatctccc agttctctgt ggacagcatc accagccagg agagcaagga gcctgtgttc   1500
attgcagcag gggacatccg ccggcgcctt tcggaacagc tggctcatac cccgacagcc   1560
ttcaaacgag acccgaagaa tccttctgca gttgctctca agagccctg gcaggagaaa    1620 gtacggcgga tcagagaggg ctcccccctac ggccatctcc ccaattggcg gctcctgtca   1680
gtcattgtca agtgtgggga tgaccttcgg caagagcttc tggcctttca ggtgttgaag   1740
caactgcagt ccatttggga acaggagcga gtgccccttt ggatcaagcc aatacaagat   1800
tcttgtgaaa ttacgactga tagtggcatg attgaaccag tggtcaatgc tgtgtccatc   1860
catcaggtga agaaacagtc acagctctcc ttgctcgatt acttcctaca ggagcacggc   1920
agttacacca ctgaggcatt cctcagtgca cagcgcaatt ttgtgcaaag ttgtgctggg   1980
tactgcttgg tctgctacct gctgcaagtc aaggacagac acaatgggaa tatccttttg   2040
gacgcagaag gccacatcat ccacatcgac tttggcttca tcctctccag ctcaccccga   2100
aatctgggct ttgagacgtc agccttaaag ctgaccacag agtttgtgga tgtgatgggc   2160
ggcctggatg cgacatgtt caactactat aagatgctga tgctgcaagg gctgattgcc    2220
gctcggaaac acatggacaa ggtggtgcag atcgtggaga tcatgcagca aggttctcag   2280
cttccttgct tccatggctc cagcaccatt cgaaacctca agagaggtt ccacatgagc    2340 atgactgagg agcagctgca gctgctggtg gagcagatgg tggatggcag tatgcggtct   2400
atcaccacca aactctatga cggcttccag tacctcacca acggcatcat g            2451
```

<210> SEQ ID NO 30
<211> LENGTH: 3602
<212> TYPE: DNA
<213> ORGANISM: Homo sapiens
<220> FEATURE:
<221> NAME/KEY: CDS
<222> LOCATION: (429)..(2879)

<400> SEQUENCE: 30

```
ggtggctcac gcctgtaatc ccagcacttt gggaggacaa ggcagatccc ttgagcccag     60
gaggtagagg ctgcagtgag ctgtgatggt gccactgcac tccagcctgg gcaatgaagc    120
aagaccctat ctgaaaaaaa aaattttaa aaaggcaaa gatgggcctg ggcaccaaa      180 tattccagag gaaagggaac gtgtgtactc cttgaggtgg ggaacatgac ccacttgagg    240
tgcagaaaga agacttgtat ggggctggtg cagcctccgc ggccgctgtc agggaagcgc    300
aggcggccaa tggaacccgg gagcggtcgc tgctgctgag gcggcagtgt cggcagtcca    360
accgcgactg cccgcacccc ctccgcgggg tccccagag cttggaagct cgaagtctgg     420
```

```
ctgtggcc atg gga gat aca gta gtg gag cct gcc ccc ttg aag cca act      470
         Met Gly Asp Thr Val Val Glu Pro Ala Pro Leu Lys Pro Thr
         1               5                   10 tct gag ccc act tct ggc cca cca ggg aat aat ggg ggg tcc ctg cta       518
Ser Glu Pro Thr Ser Gly Pro Pro Gly Asn Asn Gly Gly Ser Leu Leu
15              20                  25                  30 agt gtc atc acg gag ggg gtc ggg gaa cta tca gtg att gac cct gag       566
Ser Val Ile Thr Glu Gly Val Gly Glu Leu Ser Val Ile Asp Pro Glu
                35                  40                  45 gtg gcc cag aag gcc tgc cag gag gtg ttg gag aaa gtc aag ctt ttg       614
Val Ala Gln Lys Ala Cys Gln Glu Val Leu Glu Lys Val Lys Leu Leu
            50                  55                  60 cat gga ggc gtg gca gtc tct agc aga ggc acc cca ctg gag ttg gtc       662
His Gly Gly Val Ala Val Ser Ser Arg Gly Thr Pro Leu Glu Leu Val
        65                  70                  75 aat ggg gat ggt gtg gac agt gag atc cgt tgc cta gat gat cca cct       710
Asn Gly Asp Gly Val Asp Ser Glu Ile Arg Cys Leu Asp Asp Pro Pro
    80                  85                  90 gcc cag atc agg gag gag gaa gat gag atg ggg gcc gct gtg gcc tca       758
Ala Gln Ile Arg Glu Glu Glu Asp Glu Met Gly Ala Ala Val Ala Ser
95                  100                 105                 110 ggc aca gcc aaa gga gca aga aga cgg cgg cag aac aac tca gct aaa       806
Gly Thr Ala Lys Gly Ala Arg Arg Arg Arg Gln Asn Asn Ser Ala Lys
                115                 120                 125 cag tct tgg ctg ctg agg ctg ttt gag tca aaa ctg ttt gac atc tcc       854
Gln Ser Trp Leu Leu Arg Leu Phe Glu Ser Lys Leu Phe Asp Ile Ser
            130                 135                 140 atg gcc att tca tac ctg tat aac tcc aag gag cct gga gta caa gcc       902
Met Ala Ile Ser Tyr Leu Tyr Asn Ser Lys Glu Pro Gly Val Gln Ala
        145                 150                 155 tac att ggc aac cgg ctc ttc tgc ttt cgc aac gag gac gtg gac ttc       950
Tyr Ile Gly Asn Arg Leu Phe Cys Phe Arg Asn Glu Asp Val Asp Phe
    160                 165                 170 tat ctg ccc cag ttg ctt aac atg tac atc cac atg gat gag gac gtg       998
Tyr Leu Pro Gln Leu Leu Asn Met Tyr Ile His Met Asp Glu Asp Val
175                 180                 185                 190 ggt gat gcc att aag ccc tac ata gtc cac cgt tgc cgc cag agc att      1046
Gly Asp Ala Ile Lys Pro Tyr Ile Val His Arg Cys Arg Gln Ser Ile
                195                 200                 205 aac ttt tcc ctc cag tgt gcc ctg ttg ctt ggg gcc tat tct tca gac      1094
Asn Phe Ser Leu Gln Cys Ala Leu Leu Leu Gly Ala Tyr Ser Ser Asp
            210                 215                 220 atg cac att tcc act caa cga cac tcc cgt ggg acc aag cta cgg aag      1142
Met His Ile Ser Thr Gln Arg His Ser Arg Gly Thr Lys Leu Arg Lys
        225                 230                 235 ctg atc ctc tca gat gag cta aag cca gct cac agg aag agg gag ctg      1190
Leu Ile Leu Ser Asp Glu Leu Lys Pro Ala His Arg Lys Arg Glu Leu
    240                 245                 250 ccc tcc ttg agc ccg gcc cct gat aca ggg ctg tct ccc tcc aaa agg      1238
Pro Ser Leu Ser Pro Ala Pro Asp Thr Gly Leu Ser Pro Ser Lys Arg
255                 260                 265                 270 act cac cag cgc tct aag tca gat gcc act gcc agc ata agt ctc agc      1286
Thr His Gln Arg Ser Lys Ser Asp Ala Thr Ala Ser Ile Ser Leu Ser
                275                 280                 285 agc aac ctg aaa cga aca gcc agc aac cct aaa gtg gag aat gag gat      1334
Ser Asn Leu Lys Arg Thr Ala Ser Asn Pro Lys Val Glu Asn Glu Asp
            290                 295                 300 gag gag ctc tcc tcc agc acc gag agt att gat aat tca ttc agt tcc      1382
Glu Glu Leu Ser Ser Ser Thr Glu Ser Ile Asp Asn Ser Phe Ser Ser
        305                 310                 315
```

```
cct gtt cga ctg gct cct gag aga gaa ttc atc aag tcc ctg atg gcg    1430
Pro Val Arg Leu Ala Pro Glu Arg Glu Phe Ile Lys Ser Leu Met Ala
320             325                 330 atc ggc aag cgg ctg gcc acg ctc ccc acc aaa gag cag aaa aca cag    1478
Ile Gly Lys Arg Leu Ala Thr Leu Pro Thr Lys Glu Gln Lys Thr Gln
335             340                 345                 350 agg ctg atc tca gag ctc tcc ctg ctc aac cat aag ctc cct gcc cga    1526
Arg Leu Ile Ser Glu Leu Ser Leu Leu Asn His Lys Leu Pro Ala Arg
                355                 360                 365 gtc tgg ctg ccc act gct ggc ttt gac cac cac gtg gtc cgt gta ccc    1574
Val Trp Leu Pro Thr Ala Gly Phe Asp His His Val Val Arg Val Pro
            370                 375                 380 cac aca cag gct gtt gtc ctc aac tcc aag gac aag gct ccc tac ctg    1622
His Thr Gln Ala Val Val Leu Asn Ser Lys Asp Lys Ala Pro Tyr Leu
        385                 390                 395 att tat gtg gaa gtc ctt gaa tgt gaa aac ttt gac acc acc agt gtc    1670
Ile Tyr Val Glu Val Leu Glu Cys Glu Asn Phe Asp Thr Thr Ser Val
    400                 405                 410 cct gcc cgg atc ccc gag aac cga att cgg agt acg agg tcc gta gaa    1718
Pro Ala Arg Ile Pro Glu Asn Arg Ile Arg Ser Thr Arg Ser Val Glu
415                 420                 425                 430 aac ttg ccc gaa tgt ggt att acc cat gag cag cga gct ggc agc ttc    1766
Asn Leu Pro Glu Cys Gly Ile Thr His Glu Gln Arg Ala Gly Ser Phe
                435                 440                 445 agc act gtg ccc aac tat gac aac gat gat gag gcc tgg tcg gtg gat    1814
Ser Thr Val Pro Asn Tyr Asp Asn Asp Asp Glu Ala Trp Ser Val Asp
            450                 455                 460 gac ata ggc gag ctg caa gtg gag ctc ccc gaa gtg cat acc aac agc    1862
Asp Ile Gly Glu Leu Gln Val Glu Leu Pro Glu Val His Thr Asn Ser
        465                 470                 475 tgt gac aac atc tcc cag ttc tct gtg gac agc atc acc agc cag gag    1910
Cys Asp Asn Ile Ser Gln Phe Ser Val Asp Ser Ile Thr Ser Gln Glu
    480                 485                 490 agc aag gag cct gtg ttc att gca gca ggg gac atc cgc cgg cgc ctt    1958
Ser Lys Glu Pro Val Phe Ile Ala Ala Gly Asp Ile Arg Arg Arg Leu
495                 500                 505                 510 tcg gaa cag ctg gct cat acc ccg aca gcc ttc aaa cga gac cca gaa    2006
Ser Glu Gln Leu Ala His Thr Pro Thr Ala Phe Lys Arg Asp Pro Glu
                515                 520                 525 gat cct tct gca gtt gct ctc aaa gag ccc tgg cag gag aaa gta cgg    2054
Asp Pro Ser Ala Val Ala Leu Lys Glu Pro Trp Gln Glu Lys Val Arg
            530                 535                 540 cgg atc aga gag ggc tcc ccc tac ggc cat ctc ccc aat tgg cgg ctc    2102
Arg Ile Arg Glu Gly Ser Pro Tyr Gly His Leu Pro Asn Trp Arg Leu
        545                 550                 555 ctg tca gtc att gtc aag tgt ggg gat gac ctt cgg caa gag ctt ctg    2150
Leu Ser Val Ile Val Lys Cys Gly Asp Asp Leu Arg Gln Glu Leu Leu
    560                 565                 570 gcc ttt cag gtg ttg aag caa ctg cag tcc att tgg gaa cag gag cga    2198
Ala Phe Gln Val Leu Lys Gln Leu Gln Ser Ile Trp Glu Gln Glu Arg
575                 580                 585                 590 gtg ccc ctt tgg atc aag cca ata caa gat tct tgt gaa att acg act    2246
Val Pro Leu Trp Ile Lys Pro Ile Gln Asp Ser Cys Glu Ile Thr Thr
                595                 600                 605 gat agt ggc atg att gaa cca gtg gtc aat gct gtg tcc atc cat cag    2294
Asp Ser Gly Met Ile Glu Pro Val Val Asn Ala Val Ser Ile His Gln
            610                 615                 620 gtg aag aaa cag tca cag ctc tcc ttg ctc gat tac ttc cta cag gag    2342
Val Lys Lys Gln Ser Gln Leu Ser Leu Leu Asp Tyr Phe Leu Gln Glu
        625                 630                 635
```

```
cac ggc agt tac acc act gag gca ttc ctc agt gca cag cgc aat ttt      2390
His Gly Ser Tyr Thr Thr Glu Ala Phe Leu Ser Ala Gln Arg Asn Phe
        640             645                 650 gtg caa agt tgt gct ggg tac tgc ttg gtc tgc tac ctg ctc caa gtc      2438
Val Gln Ser Cys Ala Gly Tyr Cys Leu Val Cys Tyr Leu Leu Gln Val
655                 660                 665                 670 aag gac aga cac aat ggg aat atc ctt ttg gac gca gaa ggc cac atc      2486
Lys Asp Arg His Asn Gly Asn Ile Leu Leu Asp Ala Glu Gly His Ile
                675                 680                 685 atc cac atc gac ttt ggc ttc atc ctc tcc agc tca ccc cga aat ctg      2534
Ile His Ile Asp Phe Gly Phe Ile Leu Ser Ser Ser Pro Arg Asn Leu
            690                 695                 700 ggc ttt gag acg tca gcc ttt aag ctg acc aca gag ttt gtg gat gtg      2582
Gly Phe Glu Thr Ser Ala Phe Lys Leu Thr Thr Glu Phe Val Asp Val
        705                 710                 715 atg ggc ggc ctg gat ggc gac atg ttc aac tac tat aag atg ctg atg      2630
Met Gly Gly Leu Asp Gly Asp Met Phe Asn Tyr Tyr Lys Met Leu Met
720                 725                 730 ctg caa ggg ctg att gcc gct cgg aaa cac atg gac aag gtg gtg cag      2678
Leu Gln Gly Leu Ile Ala Ala Arg Lys His Met Asp Lys Val Val Gln
735                 740                 745                 750 atc gtg gag atc atg cag caa ggt tct cag ctt cct tgc ttc cat ggc      2726
Ile Val Glu Ile Met Gln Gln Gly Ser Gln Leu Pro Cys Phe His Gly
                755                 760                 765 tcc agc acc att cga aac ctc aaa gag agg ttc cac atg agc atg act      2774
Ser Ser Thr Ile Arg Asn Leu Lys Glu Arg Phe His Met Ser Met Thr
            770                 775                 780 gag gag cag ctg cag ctg ctg gtg gag cag atg gtg gat ggc agt atg      2822
Glu Glu Gln Leu Gln Leu Leu Val Glu Gln Met Val Asp Gly Ser Met
        785                 790                 795 cgg tct atc acc acc aaa ctc tat gac ggc ttc cag tac ctc acc aac      2870
Arg Ser Ile Thr Thr Lys Leu Tyr Asp Gly Phe Gln Tyr Leu Thr Asn
800                 805                 810 ggc atc atg tgacacgctc ctcagcccag gagtggtggg gggtccaggg              2919
Gly Ile Met
815 caccctccct agagggccct tgtctgagaa accccaaacc aggaaacccc acctacccaa    2979 ccatccaccc aagggaaatg gaaggcaaga aacacgaagg atcatgtggt aactgcgaga    3039 gcttgctgag gggtgggaga gccagctgtg gggtccagac ttgttggggc ttccctgccc    3099 ctcctggtct gtgtcagtat taccaccaga ctgactccag gactcactgc cctccagaaa    3159 acagaggtga caaatgtgag ggacactggg gcctttcttc tccttgtagg ggtctctcag    3219 aggttctttc cacaggccat cctcttattc cgttctgggg cccaggaagt ggggaagagt    3279 aggttctcgg tacttaggac ttgatcctgt ggttgccact ggccatgctg ctgcccagct    3339 ctaccctcc cagggaccta ccctcccag ggaccgaccc ctggcccaag ctccccttgc     3399 tggcgggcgc tgcgtgggcc ctgcacttgc tgaggttccc catcatgggc aaggcaaggg    3459 aattcccaca gccctccagt gtactgaggg tactggccta gccatgtgga attccctacc    3519 ctgactcctt ccccaaaccc agggaaaaga gctctcaatt ttttattttt aattttttgtt  3579 tgaaataaag tccttagtta gcc                                           3602
```

<210> SEQ ID NO 31
<211> LENGTH: 829
<212> TYPE: PRT
<213> ORGANISM: Homo sapiens

<400> SEQUENCE: 31

```
Met Arg Phe Leu Glu Ala Arg Ser Leu Ala Val Ala Met Gly Asp Thr
  1               5                  10                  15

Val Val Glu Pro Ala Pro Leu Lys Pro Thr Ser Glu Pro Thr Ser Gly
             20                  25                  30

Pro Pro Gly Asn Asn Gly Gly Ser Leu Leu Ser Val Ile Thr Glu Gly
             35                  40                  45

Val Gly Glu Leu Ser Val Ile Asp Pro Glu Val Ala Gln Lys Ala Cys
 50                  55                  60

Gln Glu Val Leu Glu Lys Val Lys Leu Leu His Gly Val Ala Val
 65                  70                  75                  80

Ser Ser Arg Gly Thr Pro Leu Glu Leu Val Asn Gly Asp Gly Val Asp
             85                  90                  95

Ser Glu Ile Arg Cys Leu Asp Asp Pro Ala Gln Ile Arg Glu Glu
            100                 105                 110

Glu Asp Glu Met Gly Ala Ala Val Ala Ser Gly Thr Ala Lys Gly Ala
            115                 120                 125

Arg Arg Arg Arg Gln Asn Asn Ser Ala Lys Gln Ser Trp Leu Leu Arg
130                 135                 140

Leu Phe Glu Ser Lys Leu Phe Asp Ile Ser Met Ala Ile Ser Tyr Leu
145                 150                 155                 160

Tyr Asn Ser Lys Glu Pro Gly Val Gln Ala Tyr Ile Gly Asn Arg Leu
            165                 170                 175

Phe Cys Phe Arg Asn Glu Asp Val Asp Phe Tyr Leu Pro Gln Leu Leu
            180                 185                 190

Asn Met Tyr Ile His Met Asp Glu Asp Val Gly Asp Ala Ile Lys Pro
            195                 200                 205

Tyr Ile Val His Arg Cys Arg Gln Ser Ile Asn Phe Ser Leu Gln Cys
210                 215                 220

Ala Leu Leu Leu Gly Ala Tyr Ser Ser Asp Met His Ile Ser Thr Gln
225                 230                 235                 240

Arg His Ser Arg Gly Thr Lys Leu Arg Lys Leu Ile Leu Ser Asp Glu
            245                 250                 255

Leu Lys Pro Ala His Arg Lys Arg Glu Leu Pro Ser Leu Ser Pro Ala
            260                 265                 270

Pro Asp Thr Gly Leu Ser Pro Ser Lys Arg Thr His Gln Arg Ser Lys
            275                 280                 285

Ser Asp Ala Thr Ala Ser Ile Ser Leu Ser Ser Asn Leu Lys Arg Thr
290                 295                 300

Ala Ser Asn Pro Lys Val Glu Asn Glu Asp Glu Glu Leu Ser Ser Ser
305                 310                 315                 320

Thr Glu Ser Ile Asp Asn Ser Phe Ser Ser Pro Val Arg Leu Ala Pro
            325                 330                 335

Glu Arg Glu Phe Ile Lys Ser Leu Met Ala Ile Gly Lys Arg Leu Ala
            340                 345                 350

Thr Leu Pro Thr Lys Glu Gln Lys Thr Gln Arg Leu Ile Ser Glu Leu
            355                 360                 365

Ser Leu Leu Asn His Lys Leu Pro Ala Arg Val Trp Leu Pro Thr Ala
370                 375                 380

Gly Phe Asp His His Val Val Arg Val Pro His Thr Gln Ala Val Val
385                 390                 395                 400

Leu Asn Ser Lys Asp Lys Ala Pro Tyr Leu Ile Tyr Val Glu Val Leu
            405                 410                 415

Glu Cys Glu Asn Phe Asp Thr Thr Ser Val Pro Ala Arg Ile Pro Glu
```

```
                420             425             430
Asn Arg Ile Arg Ser Thr Arg Ser Val Glu Asn Leu Pro Glu Cys Gly
            435             440             445

Ile Thr His Glu Gln Arg Ala Gly Ser Phe Ser Thr Val Pro Asn Tyr
            450             455             460

Asp Asn Asp Asp Glu Ala Trp Ser Val Asp Asp Ile Gly Glu Leu Gln
465             470             475             480

Val Glu Leu Pro Glu Val His Thr Asn Ser Cys Asp Asn Ile Ser Gln
            485             490             495

Phe Ser Val Asp Ser Ile Thr Ser Gln Glu Ser Lys Glu Pro Val Phe
            500             505             510

Ile Ala Ala Gly Asp Ile Arg Arg Leu Ser Glu Gln Leu Ala His
            515             520             525

Thr Pro Thr Ala Phe Lys Arg Asp Pro Glu Asp Pro Ser Ala Val Ala
            530             535             540

Leu Lys Glu Pro Trp Gln Glu Lys Val Arg Arg Ile Arg Glu Gly Ser
545             550             555             560

Pro Tyr Gly His Leu Pro Asn Trp Arg Leu Leu Ser Val Ile Val Lys
            565             570             575

Cys Gly Asp Asp Leu Arg Gln Glu Leu Leu Ala Phe Gln Val Leu Lys
            580             585             590

Gln Leu Gln Ser Ile Trp Glu Gln Arg Val Pro Leu Trp Ile Lys
            595             600             605

Pro Ile Gln Asp Ser Cys Glu Ile Thr Thr Asp Ser Gly Met Ile Glu
            610             615             620

Pro Val Val Asn Ala Val Ser Ile His Gln Val Lys Lys Gln Ser Gln
625             630             635             640

Leu Ser Leu Leu Asp Tyr Phe Leu Gln Glu His Gly Ser Tyr Thr Thr
            645             650             655

Glu Ala Phe Leu Ser Ala Gln Arg Asn Phe Val Gln Ser Cys Ala Gly
            660             665             670

Tyr Cys Leu Val Cys Tyr Leu Leu Gln Val Lys Asp Arg His Asn Gly
            675             680             685

Asn Ile Leu Leu Asp Ala Glu Gly His Ile Ile His Ile Asp Phe Gly
            690             695             700

Phe Ile Leu Ser Ser Ser Pro Arg Asn Leu Gly Phe Glu Thr Ser Ala
705             710             715             720

Phe Lys Leu Thr Thr Glu Phe Val Asp Val Met Gly Gly Leu Asp Gly
            725             730             735

Asp Met Phe Asn Tyr Tyr Lys Met Leu Met Leu Gln Gly Leu Ile Ala
            740             745             750

Ala Arg Lys His Met Asp Lys Val Val Gln Ile Val Glu Ile Met Gln
            755             760             765

Gln Gly Ser Gln Leu Pro Cys Phe His Gly Ser Ser Thr Ile Arg Asn
            770             775             780

Leu Lys Glu Arg Phe His Met Ser Met Thr Glu Glu Gln Leu Gln Leu
785             790             795             800

Leu Val Glu Gln Met Val Asp Gly Ser Met Arg Ser Ile Thr Thr Lys
            805             810             815

Leu Tyr Asp Gly Phe Gln Tyr Leu Thr Asn Gly Ile Met
            820             825

<210> SEQ ID NO 32
<211> LENGTH: 2487
```

<212> TYPE: DNA
<213> ORGANISM: Homo sapiens

<400> SEQUENCE: 32

| | | | | | |
|---|---|---|---|---|---|
| atgagattct | tggaagctcg | aagtctggct | gtggccatgg | gagatacagt | agtggagcct | 60 |
| gcccccttga | agccaacttc | tgagcccact | tctggcccac | cagggaataa | tgggggggtcc | 120 |
| ctgctaagtg | tcatcacgga | gggggtcggg | gaactatcag | tgattgaccc | tgaggtggcc | 180 |
| cagaaggcct | gccaggaggt | gttggagaaa | gtcaagcttt | tgcatggagg | cgtggcagtc | 240 |
| tctagcagag | gcaccccact | ggagttggtc | aatggggatg | tgtgtggacag | tgagatccgt | 300 |
| tgcctagatg | atccacctgc | ccagatcagg | gaggaggaag | atgagatggg | ggccgctgtg | 360 |
| gcctcaggca | cagccaaagg | agcaagaaga | cggcggcaga | caactcagc | taaacagtct | 420 |
| tggctgctga | ggctgtttga | gtcaaaactg | tttgacatct | ccatggccat | ttcatacctg | 480 |
| tataactcca | aggagcctgg | agtacaagcc | tacattggca | accggctctt | ctgctttcgc | 540 |
| aacgaggacg | tggacttcta | tctgccccag | ttgcttaaca | tgtacatcca | catggatgag | 600 |
| gacgtgggtg | atgccattaa | gccctacata | gtccaccgtt | gccgccagag | cattaacttt | 660 |
| tccctccagt | gtgccctgtt | gcttgggggcc | tattcttcag | acatgcacat | ttccactcaa | 720 |
| cgacactccc | gtgggaccaa | gctacggaag | ctgatcctct | cagatgagct | aaagccagct | 780 |
| cacaggaaga | gggagctgcc | ctccttgagc | ccggcccctg | atacagggct | gtctccctcc | 840 |
| aaaaggactc | accagcgctc | taagtcagat | gccactgcca | gcataagtct | cagcagcaac | 900 |
| ctgaaacgaa | cagccagcaa | ccctaaagtg | gagaatgagg | atgaggagct | ctcctccagc | 960 |
| accgagagta | ttgataattc | attcagttcc | cctgttcgac | tggctcctga | gagagaattc | 1020 |
| atcaagtccc | tgatggcgat | cggcaagcgg | ctggccacgc | tccccaccaa | agagcagaaa | 1080 |
| acacagaggc | tgatctcaga | gctctccctg | ctcaaccata | agctccctgc | ccgagtctgg | 1140 |
| ctgcccactg | ctggctttga | ccaccacgtg | gtccgtgtac | cccacacaca | ggctgttgtc | 1200 |
| ctcaactcca | aggacaaggc | tccctacctg | atttatgtgg | aagtccttga | atgtgaaaac | 1260 |
| tttgacacca | ccagtgtccc | tgcccggatc | cccgagaacc | gaattcggag | tacgaggtcc | 1320 |
| gtagaaaact | gcccgaatg | tggtattacc | catgagcagc | gagctggcag | cttcagcact | 1380 |
| gtgcccaact | atgacaacga | tgatgaggcc | tggtcggtgg | atgacatagg | cgagctgcaa | 1440 |
| gtggagctcc | ccgaagtgca | taccaacagc | tgtgacaaca | tctcccagtt | ctctgtggac | 1500 |
| agcatcacca | gccaggagag | caaggagcct | gtgttcattg | cagcagggga | catccgccgg | 1560 |
| cgcctttcgg | aacagctggc | tcataccccg | acagccttca | acgagaccc | agaagatcct | 1620 |
| tctgcagttg | ctctcaaaga | gccctggcag | gagaaagtac | ggcggatcag | agagggctcc | 1680 |
| ccctacggcc | atctccccaa | ttggcggctc | ctgtcagtca | ttgtcaagtg | tggggatgac | 1740 |
| cttcggcaag | agcttctggc | cttttcaggtg | ttgaagcaac | tgcagtccat | ttgggaacag | 1800 |
| gagcgagtgc | cccttttggat | caagccaata | caagattctt | gtgaaattac | gactgatagt | 1860 |
| ggcatgattg | aaccagtggt | caatgctgtg | tccatccatc | aggtgaagaa | acagtcacag | 1920 |
| ctctccttgc | tcgattactt | cctacaggag | cacggcagtt | acaccactga | ggcattcctc | 1980 |
| agtgcacagc | gcaattttgt | gcaaagttgt | gctgggtact | gcttggtctg | ctacctgctg | 2040 |
| caagtcaagg | acagacacaa | tgggaatatc | cttttggacg | cagaaggcca | catcatccac | 2100 |
| atcgactttg | gcttcatcct | ctccagctca | ccccgaaatc | tgggctttga | gacgtcagcc | 2160 |
| tttaagctga | ccacagagtt | tgtggatgtg | atgggcggcc | tggatggcga | catgttcaac | 2220 |
| tactataaga | tgctgatgct | gcaagggctg | attgccgctc | ggaaacacat | ggacaaggtg | 2280 |

```
gtgcagatcg tggagatcat gcagcaaggt tctcagcttc cttgcttcca tggctccagc    2340
accattcgaa acctcaaaga gaggttccac atgagcatga ctgaggagca gctgcagctg    2400
ctggtggagc agatggtgga tgcagtatg cggtctatca ccaccaaact ctatgacggc     2460
ttccagtacc tcaccaacgg catcatg                                        2487

<210> SEQ ID NO 33
<211> LENGTH: 3324
<212> TYPE: DNA
<213> ORGANISM: Homo sapiens
<220> FEATURE:
<221> NAME/KEY: CDS
<222> LOCATION: (115)..(2601)

<400> SEQUENCE: 33
ccggaattcc gggaaggccg gagcaagttt tgaagaagtc cctatcagat tacacttggt     60
tgactactcc ggagcagcca ctaagaggga tgaacaggcc tgcgtggaaa ttga atg     117
                                                              Met
                                                                1 aga ttc ttg gaa gct cga agt ctg gct gtg gcc atg gga gat aca gta    165
Arg Phe Leu Glu Ala Arg Ser Leu Ala Val Ala Met Gly Asp Thr Val
        5                   10                  15 gtg gag cct gcc ccc ttg aag cca act tct gag ccc act tct ggc cca    213
Val Glu Pro Ala Pro Leu Lys Pro Thr Ser Glu Pro Thr Ser Gly Pro
    20                  25                  30 cca ggg aat aat ggg ggg tcc ctg cta agt gtc atc acg gag ggg gtc    261
Pro Gly Asn Asn Gly Gly Ser Leu Leu Ser Val Ile Thr Glu Gly Val
 35                  40                  45 ggg gaa cta tca gtg att gac cct gag gtg gcc cag aag gcc tgc cag    309
Gly Glu Leu Ser Val Ile Asp Pro Glu Val Ala Gln Lys Ala Cys Gln
 50                  55                  60                  65 gag gtg ttg gag aaa gtc aag ctt ttg cat gga ggc gtg gca gtc tct    357
Glu Val Leu Glu Lys Val Lys Leu Leu His Gly Gly Val Ala Val Ser
             70                  75                  80 agc aga ggc acc cca ctg gag ttg gtc aat ggg gat ggt gtg gac agt    405
Ser Arg Gly Thr Pro Leu Glu Leu Val Asn Gly Asp Gly Val Asp Ser
         85                  90                  95 gag atc cgt tgc cta gat gat cca cct gcc cag atc agg gag gag gaa    453
Glu Ile Arg Cys Leu Asp Asp Pro Pro Ala Gln Ile Arg Glu Glu Glu
    100                 105                 110 gat gag atg ggg gcc gct gtg gcc tca ggc aca gcc aaa gga gca aga    501
Asp Glu Met Gly Ala Ala Val Ala Ser Gly Thr Ala Lys Gly Ala Arg
115                 120                 125 aga cgg cgg cag aac aac tca gct aaa cag tct tgg ctg ctg agg ctg    549
Arg Arg Arg Gln Asn Asn Ser Ala Lys Gln Ser Trp Leu Leu Arg Leu
130                 135                 140                 145 ttt gag tca aaa ctg ttt gac atc tcc atg gcc att tca tac ctg tat    597
Phe Glu Ser Lys Leu Phe Asp Ile Ser Met Ala Ile Ser Tyr Leu Tyr
                150                 155                 160 aac tcc aag gag cct gga gta caa gcc tac att gga aac cgg ctc ttc    645
Asn Ser Lys Glu Pro Gly Val Gln Ala Tyr Ile Gly Asn Arg Leu Phe
            165                 170                 175 tgc ttt cgc aac gag gac gtg gac ttc tat ctg ccc cag ttg ctt aac    693
Cys Phe Arg Asn Glu Asp Val Asp Phe Tyr Leu Pro Gln Leu Leu Asn
        180                 185                 190 atg tac atc cac atg gat gag gac gtg ggt gat gcc att aag ccc tac    741
Met Tyr Ile His Met Asp Glu Asp Val Gly Asp Ala Ile Lys Pro Tyr
    195                 200                 205 ata gtc cac cgt tgc cgc cag agc att aac ttt tcc ctc cag tgt gcc    789
Ile Val His Arg Cys Arg Gln Ser Ile Asn Phe Ser Leu Gln Cys Ala
210                 215                 220
```

```
                210                   215                   220                   225
ctg ttg ctt ggg gcc tat tct tca gac atg cac att tcc act caa cga           837
Leu Leu Leu Gly Ala Tyr Ser Ser Asp Met His Ile Ser Thr Gln Arg
                230                   235                   240 cac tcc cgt ggg acc aag cta cgg aag ctg atc ctc tca gat gag cta           885
His Ser Arg Gly Thr Lys Leu Arg Lys Leu Ile Leu Ser Asp Glu Leu
            245                   250                   255 aag cca gct cac agg aag agg gag ctg ccc tcc ttg agc ccg gcc cct           933
Lys Pro Ala His Arg Lys Arg Glu Leu Pro Ser Leu Ser Pro Ala Pro
        260                   265                   270 gat aca ggg ctg tct ccc tcc aaa agg act cac cag cgc tct aag tca           981
Asp Thr Gly Leu Ser Pro Ser Lys Arg Thr His Gln Arg Ser Lys Ser
    275                   280                   285 gat gcc act gcc agc ata agt ctc agc agc aac ctg aaa cga aca gcc          1029
Asp Ala Thr Ala Ser Ile Ser Leu Ser Ser Asn Leu Lys Arg Thr Ala
290                   295                   300                   305 agc aac cct aaa gtg gag aat gag gat gag gag ctc tcc tcc agc acc          1077
Ser Asn Pro Lys Val Glu Asn Glu Asp Glu Glu Leu Ser Ser Ser Thr
                310                   315                   320 gag agt att gat aat tca ttc agt tcc cct gtt cga ctg gct cct gag          1125
Glu Ser Ile Asp Asn Ser Phe Ser Ser Pro Val Arg Leu Ala Pro Glu
            325                   330                   335 aga gaa ttc atc aag tcc ctg atg gcg atc ggc aag cgg ctg gcc acg          1173
Arg Glu Phe Ile Lys Ser Leu Met Ala Ile Gly Lys Arg Leu Ala Thr
        340                   345                   350 ctc ccc acc aaa gag cag aaa aca cag agg ctg atc tca gag ctc tcc          1221
Leu Pro Thr Lys Glu Gln Lys Thr Gln Arg Leu Ile Ser Glu Leu Ser
    355                   360                   365 ctg ctc aac cat aag ctc cct gcc cga gtc tgg ctg ccc act gct ggc          1269
Leu Leu Asn His Lys Leu Pro Ala Arg Val Trp Leu Pro Thr Ala Gly
370                   375                   380                   385 ttt gac cac cac gtg gtc cgt gta ccc cac aca cag gct gtt gtc ctc          1317
Phe Asp His His Val Val Arg Val Pro His Thr Gln Ala Val Val Leu
                390                   395                   400 aac tcc aag gac aag gct ccc tac ctg att tat gtg gaa gtc ctt gaa          1365
Asn Ser Lys Asp Lys Ala Pro Tyr Leu Ile Tyr Val Glu Val Leu Glu
            405                   410                   415 tgt gaa aac ttt gac acc acc agt gtc cct gcc cgg atc ccc gag aac          1413
Cys Glu Asn Phe Asp Thr Thr Ser Val Pro Ala Arg Ile Pro Glu Asn
        420                   425                   430 cga att cgg agt acg agg tcc gta gaa aac ttg ccc gaa tgt ggt att          1461
Arg Ile Arg Ser Thr Arg Ser Val Glu Asn Leu Pro Glu Cys Gly Ile
    435                   440                   445 acc cat gag cag cga gct ggc agc ttc agc act gtg ccc aac tat gac          1509
Thr His Glu Gln Arg Ala Gly Ser Phe Ser Thr Val Pro Asn Tyr Asp
450                   455                   460                   465 aac gat gat gag gcc tgg tcg gtg gat gac ata ggc gag ctg caa gtg          1557
Asn Asp Asp Glu Ala Trp Ser Val Asp Asp Ile Gly Glu Leu Gln Val
                470                   475                   480 gag ctc ccc gaa gtg cat acc aac agc tgt gac aac atc tcc cag ttc          1605
Glu Leu Pro Glu Val His Thr Asn Ser Cys Asp Asn Ile Ser Gln Phe
            485                   490                   495 tct gtg gac agc atc acc agc cag gag agc aag gag cct gtg ttc att          1653
Ser Val Asp Ser Ile Thr Ser Gln Glu Ser Lys Glu Pro Val Phe Ile
        500                   505                   510 gca gca ggg gac atc cgc cgg cgc ctt tcg gaa cag ctg gct cat acc          1701
Ala Ala Gly Asp Ile Arg Arg Arg Leu Ser Glu Gln Leu Ala His Thr
    515                   520                   525 ccg aca gcc ttc aaa cga gac cca gaa gat cct tct gca gtt gct ctc          1749
Pro Thr Ala Phe Lys Arg Asp Pro Glu Asp Pro Ser Ala Val Ala Leu
```

```
                530              535              540              545
aaa gag ccc tgg cag gag aaa gta cgg cgg atc aga gag ggc tcc ccc    1797
Lys Glu Pro Trp Gln Glu Lys Val Arg Arg Ile Arg Glu Gly Ser Pro
                550                       555                560 tac ggc cat ctc ccc aat tgg cgg ctc ctg tca gtc att gtc aag tgt    1845
Tyr Gly His Leu Pro Asn Trp Arg Leu Leu Ser Val Ile Val Lys Cys
                565                       570                575 ggg gat gac ctt cgg caa gag ctt ctg gcc ttt cag gtg ttg aag caa    1893
Gly Asp Asp Leu Arg Gln Glu Leu Leu Ala Phe Gln Val Leu Lys Gln
                580                       585                590 ctg cag tcc att tgg gaa cag gag cga gtg ccc ctt tgg atc aag cca    1941
Leu Gln Ser Ile Trp Glu Gln Glu Arg Val Pro Leu Trp Ile Lys Pro
                595                       600                605 ata caa gat tct tgt gaa att acg act gat agt ggc atg att gaa cca    1989
Ile Gln Asp Ser Cys Glu Ile Thr Thr Asp Ser Gly Met Ile Glu Pro
610                       615                       620                625 gtg gtc aat gct gtg tcc atc cat cag gtg aag aaa cag tca cag ctc    2037
Val Val Asn Ala Val Ser Ile His Gln Val Lys Lys Gln Ser Gln Leu
                630                       635                640 tcc ttg ctc gat tac ttc cta cag gag cac ggc agt tac acc act gag    2085
Ser Leu Leu Asp Tyr Phe Leu Gln Glu His Gly Ser Tyr Thr Thr Glu
                645                       650                655 gca ttc ctc agt gca cag cgc aat ttt gtg caa agt tgt gct ggg tac    2133
Ala Phe Leu Ser Ala Gln Arg Asn Phe Val Gln Ser Cys Ala Gly Tyr
                660                       665                670 tgc ttg gtc tgc tac ctg ctg caa gtc aag gac aga cac aat ggg aat    2181
Cys Leu Val Cys Tyr Leu Leu Gln Val Lys Asp Arg His Asn Gly Asn
                675                       680                685 atc ctt ttg gac gca gaa ggc cac atc atc cac atc gac ttt ggc ttc    2229
Ile Leu Leu Asp Ala Glu Gly His Ile Ile His Ile Asp Phe Gly Phe
690                       695                       700                705 atc ctc tcc agc tca ccc cga aat ctg ggc ttt gag acg tca gcc ttt    2277
Ile Leu Ser Ser Ser Pro Arg Asn Leu Gly Phe Glu Thr Ser Ala Phe
                710                       715                720 aag ctg acc aca gag ttt gtg gat gtg atg ggc ggc ctg gat ggc gac    2325
Lys Leu Thr Thr Glu Phe Val Asp Val Met Gly Gly Leu Asp Gly Asp
                725                       730                735 atg ttc aac tac tat aag atg ctg atg ctg caa ggg ctg att gcc gct    2373
Met Phe Asn Tyr Tyr Lys Met Leu Met Leu Gln Gly Leu Ile Ala Ala
                740                       745                750 cgg aaa cac atg gac aag gtg gtg cag atc gtg gag atc atg cag caa    2421
Arg Lys His Met Asp Lys Val Val Gln Ile Val Glu Ile Met Gln Gln
                755                       760                765 ggt tct cag ctt cct tgc ttc cat ggc tcc agc acc att cga aac ctc    2469
Gly Ser Gln Leu Pro Cys Phe His Gly Ser Ser Thr Ile Arg Asn Leu
770                       775                       780                785 aaa gag agg ttc cac atg agc atg act gag gag cag ctg cag ctg ctg    2517
Lys Glu Arg Phe His Met Ser Met Thr Glu Glu Gln Leu Gln Leu Leu
                790                       795                800 gtg gag cag atg gtg gat ggc agt atg cgg tct atc acc acc aaa ctc    2565
Val Glu Gln Met Val Asp Gly Ser Met Arg Ser Ile Thr Thr Lys Leu
                805                       810                815 tat gac ggc ttc cag tac ctc acc aac ggc atc atg tgacacgctc         2611
Tyr Asp Gly Phe Gln Tyr Leu Thr Asn Gly Ile Met
                820                       825 ctcagcccag gagtggtggg gggtccaggg caccctccct agagggccct tgtctgagaa   2671 acccccaaacc aggaaacccc acctacccaa ccatccaccc aagggaaatg gaaggcaaga  2731
aacacgaagg atcatgtggt aactgcgaga gcttgctgag gggtgggaga gccagctgtg   2791
```

-continued

```
gggtccagac ttgttggggc ttccctgccc ctcctggtct gtgtcagtat taccaccaga    2851
ctgactccag gactcactgc cctccagaaa acagaggtga caaatgtgag ggacactggg    2911
gcctttcttc tccttgtagg ggtctctcag aggttctttc cacaggccat cctcttattc    2971
cgttctgggg cccaggaagt ggggaagagt aggttctcgg tacttaggac ttgatcctgt    3031
ggttgccact ggccatgctg ctgcccagct ctacccctcc cagggaccta ccctcccag     3091 ggaccgaccc ctggcccaag ctccccttgc tggcgggcgc tgcgtgggcc ctgcacttgc    3151
tgaggttccc catcatgggc aaggcaaggg aattcccaca gccctccagt gtactgaggg    3211
tactggccta gccatgtgga attccctacc ctgactcctt ccccaaaccc agggaaaaga   3271
gctctcaatt tttttatttttt aattttttgtt tgaaataaag tccttagtta gcc         3324
```

<210> SEQ ID NO 34
<211> LENGTH: 810
<212> TYPE: PRT
<213> ORGANISM: Homo sapiens

<400> SEQUENCE: 34

```
Met Pro Met Asp Leu Ile Leu Val Val Trp Phe Cys Val Cys Thr Ala
 1               5                  10                  15

Arg Thr Val Val Gly Phe Gly Met Asp Pro Asp Leu Gln Met Asp Ile
                20                  25                  30

Val Thr Glu Leu Asp Leu Val Asn Thr Thr Leu Gly Val Ala Gln Val
            35                  40                  45

Ser Gly Met His Asn Ala Ser Lys Ala Phe Leu Phe Gln Asp Ile Glu
        50                  55                  60

Arg Glu Ile His Ala Ala Pro His Val Ser Glu Lys Leu Ile Gln Leu
    65                  70                  75                  80

Phe Gln Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
    210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285
```

```
Gly Asp His Cys Arg Asn Cys Thr Cys Lys Ser Gly Ala Val Glu Cys
    290                 295                 300
Arg Arg Met Ser Cys Pro Pro Leu Asn Cys Ser Pro Asp Ser Leu Pro
305                 310                 315                 320
Val His Ile Ala Gly Gln Cys Cys Lys Val Cys Arg Pro Lys Cys Ile
                    325                 330                 335
Tyr Gly Gly Lys Val Leu Ala Glu Gly Gln Arg Ile Leu Thr Lys Ser
                340                 345                 350
Cys Arg Glu Cys Arg Gly Gly Val Leu Val Lys Ile Thr Glu Met Cys
            355                 360                 365
Pro Pro Leu Asn Cys Ser Glu Lys Asp His Ile Leu Pro Glu Asn Gln
        370                 375                 380
Cys Cys Arg Val Cys Arg Gly His Asn Phe Cys Ala Glu Gly Pro Lys
385                 390                 395                 400
Cys Gly Glu Asn Ser Glu Cys Lys Asn Trp Asn Thr Lys Ala Thr Cys
                    405                 410                 415
Glu Cys Lys Ser Gly Tyr Ile Ser Val Gln Gly Asp Ser Ala Tyr Cys
                420                 425                 430
Glu Asp Ile Asp Glu Cys Ala Ala Lys Met His Tyr Cys His Ala Asn
            435                 440                 445
Thr Val Cys Val Asn Leu Pro Gly Leu Tyr Arg Cys Asp Cys Val Pro
        450                 455                 460
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                    485                 490                 495
Val Gln Gly His Ser Cys Thr Cys Lys Pro Gly Tyr Val Gly Asn Gly
                500                 505                 510
Thr Ile Cys Arg Ala Phe Cys Glu Glu Gly Cys Arg Tyr Gly Gly Thr
            515                 520                 525
Cys Val Ala Pro Asn Lys Cys Val Cys Pro Ser Gly Phe Thr Gly Ser
        530                 535                 540
His Cys Glu Lys Asp Ile Asp Glu Cys Ser Glu Gly Ile Ile Glu Cys
545                 550                 555                 560
His Asn His Ser Arg Cys Val Asn Leu Pro Gly Trp Tyr His Cys Glu
                    565                 570                 575
Cys Arg Ser Gly Phe His Asp Asp Gly Thr Tyr Ser Leu Ser Gly Glu
                580                 585                 590
Ser Cys Ile Asp Ile Asp Glu Cys Ala Leu Arg Thr His Thr Cys Trp
            595                 600                 605
Asn Asp Ser Ala Cys Ile Asn Leu Ala Gly Gly Phe Asp Cys Leu Cys
        610                 615                 620
Pro Ser Gly Pro Ser Cys Ser Gly Asp Cys Pro His Glu Gly Gly Leu
625                 630                 635                 640
Lys His Asn Gly Gln Val Trp Thr Leu Lys Glu Asp Arg Cys Ser Val
                    645                 650                 655
Cys Ser Cys Lys Asp Gly Lys Ile Phe Cys Arg Arg Thr Ala Cys Asp
                660                 665                 670
Cys Gln Asn Pro Ser Ala Asp Leu Phe Cys Cys Pro Glu Cys Asp Thr
            675                 680                 685
Arg Val Thr Ser Gln Cys Leu Asp Gln Asn Gly His Lys Leu Tyr Arg
        690                 695                 700
Ser Gly Asp Asn Trp Thr His Ser Cys Gln Gln Cys Arg Cys Leu Glu
705                 710                 715                 720
```

-continued

```
Gly Glu Val Asp Cys Trp Pro Leu Thr Cys Pro Asn Leu Ser Cys Glu
                725                 730                 735
Tyr Thr Ala Ile Leu Glu Gly Glu Cys Cys Pro Arg Cys Val Ser Asp
            740                 745                 750
Pro Cys Leu Ala Asp Asn Ile Thr Tyr Asp Ile Arg Lys Thr Cys Leu
                755                 760                 765
Asp Ser Tyr Gly Val Ser Arg Leu Ser Gly Ser Val Trp Thr Met Ala
        770                 775                 780
Gly Ser Pro Cys Thr Thr Cys Lys Cys Lys Asn Gly Arg Val Cys Cys
785                 790                 795                 800
Ser Val Asp Phe Glu Cys Leu Gln Asn Asn
                805                 810
```

<210> SEQ ID NO 35
<211> LENGTH: 2430
<212> TYPE: DNA
<213> ORGANISM: Homo sapiens

<400> SEQUENCE: 35

| | | | | | |
|---|---|---|---|---|---|
| atgccgatgg | atttgatttt | agttgtgtgg | ttctgtgtgt | gcactgccag | gacagtggtg | 60 |
| ggctttggga | tggaccctga | ccttcagatg | gatatcgtca | ccgagcttga | ccttgtgaac | 120 |
| accaccctyg | gagttgctca | ggtgtctgga | atgcacaatg | ccagcaaagc | attttattt | 180 |
| caagacatag | aaagagagat | ccatgcagct | cctcatgtga | gtgagaaatt | aattcagctg | 240 |
| ttccagaaca | agagtgaatt | caccattttg | gccactgtac | agcagaagcc | atccacttca | 300 |
| ggagtgatac | tgtccattcg | agaactggag | cacagctatt | tgaactgga | gagcagtggc | 360 |
| ctgagggatg | agattcggta | tcactacata | cacaatggga | agccaaggac | agaggcactt | 420 |
| ccttaccgca | tggcagatgg | acaatggcac | aaggttgcac | tgtcagttag | cgcctctcat | 480 |
| ctcctgctcc | atgtcgactg | taacaggatt | tatgagcgtg | tgatagaccc | tccagatacc | 540 |
| aaccttcccc | caggaatcaa | tttatggctt | ggccagcgca | ccaaaagca | tggcttattc | 600 |
| aaagggatca | tccaagatgg | gaagatcatc | tttatgccga | atggatatat | aacacagtgt | 660 |
| ccaaatctaa | atcacacttg | cccaacctgc | agtgattct | taagcctggt | gcaaggaata | 720 |
| atggattac | aagagctttt | ggccaagatg | actgcaaaac | taaattatgc | agagacaaga | 780 |
| cttagtcaat | tggaaaactg | tcattgtgag | aagacttgtc | aagtgagtgg | actgctctat | 840 |
| cgagatcaag | actcttgggt | agatggtgac | cattgcagga | actgcacttg | caaaagtggt | 900 |
| gccgtggaat | gccgaaggat | gtcctgtccc | cctctcaatt | gctccccaga | ctccctccca | 960 |
| gtacacattg | ctggccagtg | ctgtaaggtc | tgccgaccaa | aatgtatcta | tggaggaaaa | 1020 |
| gttcttgcag | aaggccagcg | gattttaacc | aagagctgtc | gggaatgccg | aggtggagtt | 1080 |
| ttagtaaaaa | ttacagaaat | gtgtcctcct | ttgaactgct | cagaaaagga | tcacattctt | 1140 |
| cctgagaatc | agtgctgccg | tgtctgtaga | ggtcataact | tttgtgcaga | aggacctaaa | 1200 |
| tgtggtgaaa | actcagagtg | caaaaactgg | aatacaaaag | ctacttgtga | gtgcaagagt | 1260 |
| ggttacatct | ctgtccaggg | agactctgcc | tactgtgaag | atattgatga | gtgtgcagct | 1320 |
| aagatgcatt | actgtcatgc | caatactgtg | tgtgtcaacc | ttcctgggtt | atatcgctgt | 1380 |
| gactgtgtcc | caggatacat | tcgtgtggat | gacttctctt | gtacagaaca | cgatgaatgt | 1440 |
| ggcagcggcc | agcacaactg | tgatgagaat | gccatctgca | ccaacactgt | ccaggacac | 1500 |
| agctgcacct | gcaaaccggg | ctacgtgggg | aacgggacca | tctgcagagc | tttctgtgaa | 1560 |
| gagggctgca | gatacggtgg | aacgtgtgtg | gctcccaaca | aatgtgtctg | tccatctgga | 1620 |

```
ttcacaggaa gccactgcga gaaagatatt gatgaatgtt cagagggaat cattgagtgc   1680
cacaaccatt cccgctgcgt taacctgcca gggtggtacc actgtgagtg cagaagcggt   1740
ttccatgacg atgggaccta ttcactgtcc ggggagtcct gtattgacat tgatgaatgt   1800
gccttaagaa ctcacacctg ttggaacgat tctgcctgca tcaacctggc agggggtttt   1860
gactgtctct gccccctctgg gccctcctgc tctggtgact gtcctcatga agggggggctg   1920 aagcacaatg gccaggtgtg gaccttgaaa gaagacaggt gttctgtctg ctcctgcaag   1980
gatggcaaga tattctgccg acggacagct tgtgattgcc agaatccaag tgctgaccta   2040
ttctgttgcc cagaatgtga caccagagtc acaagtcaat gtttagacca aaatggtcac   2100
aagctgtatc gaagtggaga caattggacc catagctgtc agcagtgtcg gtgtctggaa   2160
ggagaggtag attgctggcc actcacttgc cccaacttga gctgtgagta tacagctatc   2220
ttagaagggg aatgttgtcc ccgctgtgtc agtgacccct gcctagctga taacatcacc   2280
tatgacatca gaaaaacttg cctggacagc tatggtgttt cacggcttag tggctcagtg   2340
tggacgatgg ctggatctcc ctgcacaacc tgtaaatgca agaatggaag agtctgttgt   2400
tctgtggatt ttgagtgtct tcaaaataat                                    2430
```

```
<210> SEQ ID NO 36
<211> LENGTH: 2977
<212> TYPE: DNA
<213> ORGANISM: Homo sapiens
<220> FEATURE:
<221> NAME/KEY: CDS
<222> LOCATION: (103)..(2532)

<400> SEQUENCE: 36
```

```
tagcaagttt ggcggctcca agccaggcgc gcctcaggat ccaggctcat ttgcttccac         60
ctagcttcgg tgccccctgc taggcgggga ccctcgagag cg atg ccg atg gat          114
                                                Met Pro Met Asp
                                                 1 ttg att tta gtt gtg tgg ttc tgt gtg tgc act gcc agg aca gtg gtg        162
Leu Ile Leu Val Val Trp Phe Cys Val Cys Thr Ala Arg Thr Val Val
  5                  10                  15                  20 ggc ttt ggg atg gac cct gac ctt cag atg gat atc gtc acc gag ctt        210
Gly Phe Gly Met Asp Pro Asp Leu Gln Met Asp Ile Val Thr Glu Leu
                 25                  30                  35 gac ctt gtg aac acc acc ctt gga gtt gct cag gtg tct gga atg cac        258
Asp Leu Val Asn Thr Thr Leu Gly Val Ala Gln Val Ser Gly Met His
             40                  45                  50 aat gcc agc aaa gca ttt tta ttt caa gac ata gaa aga gag atc cat        306
Asn Ala Ser Lys Ala Phe Leu Phe Gln Asp Ile Glu Arg Glu Ile His
         55                  60                  65 gca gct cct cat gtg agt gag aaa tta att cag ctg ttc cag aac aag        354
Ala Ala Pro His Val Ser Glu Lys Leu Ile Gln Leu Phe Gln Asn Lys
     70                  75                  80 agt gaa ttc acc att ttg gcc act gta cag cag aag cca tcc act tca        402
Ser Glu Phe Thr Ile Leu Ala Thr Val Gln Gln Lys Pro Ser Thr Ser
 85                  90                  95                 100 gga gtg ata ctg tcc att cga gaa ctg gag cac agc tat ttt gaa ctg        450
Gly Val Ile Leu Ser Ile Arg Glu Leu Glu His Ser Tyr Phe Glu Leu
                105                 110                 115 gag agc agt ggc ctg agg gat gag att cgg tat cac tac ata cac aat        498
Glu Ser Ser Gly Leu Arg Asp Glu Ile Arg Tyr His Tyr Ile His Asn
            120                 125                 130 ggg aag cca agg aca gag gca ctt cct tac cgc atg gca gat gga caa        546
Gly Lys Pro Arg Thr Glu Ala Leu Pro Tyr Arg Met Ala Asp Gly Gln
```

```
                         135                 140                 145
tgg cac aag gtt gca ctg tca gtt agc gcc tct cat ctc ctg ctc cat        594
Trp His Lys Val Ala Leu Ser Val Ser Ala Ser His Leu Leu Leu His
150                 155                 160 gtc gac tgt aac agg att tat gag cgt gtg ata gac cct cca gat acc        642
Val Asp Cys Asn Arg Ile Tyr Glu Arg Val Ile Asp Pro Pro Asp Thr
165                 170                 175                 180 aac ctt ccc cca gga atc aat tta tgg ctt ggc cag cgc aac caa aag        690
Asn Leu Pro Pro Gly Ile Asn Leu Trp Leu Gly Gln Arg Asn Gln Lys
                185                 190                 195 cat ggc tta ttc aaa ggg atc atc caa gat ggg aag atc atc ttt atg        738
His Gly Leu Phe Lys Gly Ile Ile Gln Asp Gly Lys Ile Ile Phe Met
            200                 205                 210 ccg aat gga tat ata aca cag tgt cca aat cta aat cac act tgc cca        786
Pro Asn Gly Tyr Ile Thr Gln Cys Pro Asn Leu Asn His Thr Cys Pro
        215                 220                 225 acc tgc agt gat ttc tta agc ctg gtg caa gga ata atg gat tta caa        834
Thr Cys Ser Asp Phe Leu Ser Leu Val Gln Gly Ile Met Asp Leu Gln
    230                 235                 240 gag ctt ttg gcc aag atg act gca aaa cta aat tat gca gag aca aga        882
Glu Leu Leu Ala Lys Met Thr Ala Lys Leu Asn Tyr Ala Glu Thr Arg
245                 250                 255                 260 ctt agt caa ttg gaa aac tgt cat tgt gag aag act tgt caa gtg agt        930
Leu Ser Gln Leu Glu Asn Cys His Cys Glu Lys Thr Cys Gln Val Ser
                265                 270                 275 gga ctg ctc tat cga gat caa gac tct tgg gta gat ggt gac cat tgc        978
Gly Leu Leu Tyr Arg Asp Gln Asp Ser Trp Val Asp Gly Asp His Cys
            280                 285                 290 agg aac tgc act tgc aaa agt ggt gcc gtg gaa tgc cga agg atg tcc       1026
Arg Asn Cys Thr Cys Lys Ser Gly Ala Val Glu Cys Arg Arg Met Ser
        295                 300                 305 tgt ccc cct ctc aat tgc tcc cca gac tcc ctc cca gta cac att gct       1074
Cys Pro Pro Leu Asn Cys Ser Pro Asp Ser Leu Pro Val His Ile Ala
    310                 315                 320 ggc cag tgc tgt aag gtc tgc cga cca aaa tgt atc tat gga gga aaa       1122
Gly Gln Cys Cys Lys Val Cys Arg Pro Lys Cys Ile Tyr Gly Gly Lys
325                 330                 335                 340 gtt ctt gca gaa ggc cag cgg att tta acc aag agc tgt cgg gaa tgc       1170
Val Leu Ala Glu Gly Gln Arg Ile Leu Thr Lys Ser Cys Arg Glu Cys
                345                 350                 355 cga ggt gga gtt tta gta aaa att aca gaa atg tgt cct cct ttg aac       1218
Arg Gly Gly Val Leu Val Lys Ile Thr Glu Met Cys Pro Pro Leu Asn
            360                 365                 370 tgc tca gaa aag gat cac att ctt cct gag aat cag tgc tgc cgt gtc       1266
Cys Ser Glu Lys Asp His Ile Leu Pro Glu Asn Gln Cys Cys Arg Val
        375                 380                 385 tgt aga ggt cat aac ttt tgt gca gaa gga cct aaa tgt ggt gaa aac       1314
Cys Arg Gly His Asn Phe Cys Ala Glu Gly Pro Lys Cys Gly Glu Asn
    390                 395                 400 tca gag tgc aaa aac tgg aat aca aaa gct act tgt gag tgc aag agt       1362
Ser Glu Cys Lys Asn Trp Asn Thr Lys Ala Thr Cys Glu Cys Lys Ser
405                 410                 415                 420 ggt tac atc tct gtc cag gga gac tct gcc tac tgt gaa gat att gat       1410
Gly Tyr Ile Ser Val Gln Gly Asp Ser Ala Tyr Cys Glu Asp Ile Asp
                425                 430                 435 gag tgt gca gct aag atg cat tac tgt cat gcc aat act gtg tgt gtc       1458
Glu Cys Ala Ala Lys Met His Tyr Cys His Ala Asn Thr Val Cys Val
            440                 445                 450 aac ctt cct ggg tta tat cgc tgt gac tgt gtc cca gga tac att cgt       1506
Asn Leu Pro Gly Leu Tyr Arg Cys Asp Cys Val Pro Gly Tyr Ile Arg
```

-continued

| | | |
|---|---|---|
| gtg gat gac ttc tct tgt aca gaa cac gat gaa tgt ggc agc ggc cag<br>Val Asp Asp Phe Ser Cys Thr Glu His Asp Glu Cys Gly Ser Gly Gln<br>470                                   475                           480 | 1554 |

```
                455                 460                 465
gtg gat gac ttc tct tgt aca gaa cac gat gaa tgt ggc agc ggc cag    1554
Val Asp Asp Phe Ser Cys Thr Glu His Asp Glu Cys Gly Ser Gly Gln
            470                 475                 480 cac aac tgt gat gag aat gcc atc tgc acc aac act gtc cag gga cac    1602
His Asn Cys Asp Glu Asn Ala Ile Cys Thr Asn Thr Val Gln Gly His
        485                 490                 495             500 agc tgc acc tgc aaa ccg ggc tac gtg ggg aac ggg acc atc tgc aga    1650
Ser Cys Thr Cys Lys Pro Gly Tyr Val Gly Asn Gly Thr Ile Cys Arg
                505                 510                 515 gct ttc tgt gaa gag ggc tgc aga tac ggt gga acg tgt gtg gct ccc    1698
Ala Phe Cys Glu Glu Gly Cys Arg Tyr Gly Gly Thr Cys Val Ala Pro
            520                 525                 530 aac aaa tgt gtc tgt cca tct gga ttc aca gga agc cac tgc gag aaa    1746
Asn Lys Cys Val Cys Pro Ser Gly Phe Thr Gly Ser His Cys Glu Lys
        535                 540                 545 gat att gat gaa tgt tca gag gga atc att gag tgc cac aac cat tcc    1794
Asp Ile Asp Glu Cys Ser Glu Gly Ile Ile Glu Cys His Asn His Ser
    550                 555                 560 cgc tgc gtt aac ctg cca ggg tgg tac cac tgt gag tgc aga agc ggt    1842
Arg Cys Val Asn Leu Pro Gly Trp Tyr His Cys Glu Cys Arg Ser Gly
565                 570                 575                 580 ttc cat gac gat ggg acc tat tca ctg tcc ggg gag tcc tgt att gac    1890
Phe His Asp Asp Gly Thr Tyr Ser Leu Ser Gly Glu Ser Cys Ile Asp
                585                 590                 595 att gat gaa tgt gcc tta aga act cac acc tgt tgg aac gat tct gcc    1938
Ile Asp Glu Cys Ala Leu Arg Thr His Thr Cys Trp Asn Asp Ser Ala
            600                 605                 610 tgc atc aac ctg gca ggg ggt ttt gac tgt ctc tgc ccc tct ggg ccc    1986
Cys Ile Asn Leu Ala Gly Gly Phe Asp Cys Leu Cys Pro Ser Gly Pro
        615                 620                 625 tcc tgc tct ggt gac tgt cct cat gaa ggg ggg ctg aag cac aat ggc    2034
Ser Cys Ser Gly Asp Cys Pro His Glu Gly Gly Leu Lys His Asn Gly
    630                 635                 640 cag gtg tgg acc ttg aaa gaa gac agg tgt tct gtc tgc tcc tgc aag    2082
Gln Val Trp Thr Leu Lys Glu Asp Arg Cys Ser Val Cys Ser Cys Lys
645                 650                 655                 660 gat ggc aag ata ttc tgc cga cgg aca gct tgt gat tgc cag aat cca    2130
Asp Gly Lys Ile Phe Cys Arg Arg Thr Ala Cys Asp Cys Gln Asn Pro
                665                 670                 675 agt gct gac cta ttc tgt tgc cca gaa tgt gac acc aga gtc aca agt    2178
Ser Ala Asp Leu Phe Cys Cys Pro Glu Cys Asp Thr Arg Val Thr Ser
            680                 685                 690 caa tgt tta gac caa aat ggt cac aag ctg tat cga agt gga gac aat    2226
Gln Cys Leu Asp Gln Asn Gly His Lys Leu Tyr Arg Ser Gly Asp Asn
        695                 700                 705 tgg acc cat agc tgt cag cag tgt cgg tgt ctg gaa gga gag gta gat    2274
Trp Thr His Ser Cys Gln Gln Cys Arg Cys Leu Glu Gly Glu Val Asp
    710                 715                 720 tgc tgg cca ctc act tgc ccc aac ttg agc tgt gag tat aca gct atc    2322
Cys Trp Pro Leu Thr Cys Pro Asn Leu Ser Cys Glu Tyr Thr Ala Ile
725                 730                 735                 740 tta gaa ggg gaa tgt tgt ccc cgc tgt gtc agt gac ccc tgc cta gct    2370
Leu Glu Gly Glu Cys Cys Pro Arg Cys Val Ser Asp Pro Cys Leu Ala
                745                 750                 755 gat aac atc acc tat gac atc aga aaa act tgc ctg gac agc tat ggt    2418
Asp Asn Ile Thr Tyr Asp Ile Arg Lys Thr Cys Leu Asp Ser Tyr Gly
            760                 765                 770 gtt tca cgg ctt agt ggc tca gtg tgg acg atg gct gga tct ccc tgc    2466
Val Ser Arg Leu Ser Gly Ser Val Trp Thr Met Ala Gly Ser Pro Cys
```

```
                 775                 780                 785
aca acc tgt aaa tgc aag aat gga aga gtc tgt tgt tct gtg gat ttt      2514
Thr Thr Cys Lys Cys Lys Asn Gly Arg Val Cys Cys Ser Val Asp Phe
        790                 795                 800 gag tgt ctt caa aat aat tgaagtattt acagtggact caacgcagaa              2562
Glu Cys Leu Gln Asn Asn
805             810 gaatggacga aatgaccatc caacgtgatt aaggatagga atcggtagtt tggttttttt     2622
gtttgttttg ttttttaac cacagataat tgccaaagtt tccacctgag gacggtgttt      2682
cggaggttgc cttttggacc taccactttg ctcattcttg ctaacctagt ctaggtgacc     2742
tacagtgccg tgcatttaag tcaatggttg ttaaagaag tttcccgtgt tgtaaatcat      2802
gtttccctta tcagatcatt tgcaaataca tttaaatgat ctcatggtaa atggttgatg    2862 tatttttgg gtttattttg tgtactaacc ataatagaga gagactcagc tccttttatt     2922
tattttgttg atttatggat caaattctaa aataaagttg cctgttgtga ctttt         2977
```

<210> SEQ ID NO 37
<211> LENGTH: 816
<212> TYPE: PRT
<213> ORGANISM: Homo sapiens

<400> SEQUENCE: 37

```
Met Glu Ser Arg Val Leu Leu Arg Thr Phe Cys Leu Ile Phe Gly Leu
 1               5                  10                  15

Gly Ala Val Trp Gly Leu Gly Val Asp Pro Ser Leu Gln Ile Asp Val
            20                  25                  30

Leu Thr Glu Leu Glu Leu Gly Glu Ser Thr Thr Gly Val Arg Gln Val
        35                  40                  45

Pro Gly Leu His Asn Gly Thr Lys Ala Phe Leu Phe Gln Asp Thr Pro
    50                  55                  60

Arg Ser Ile Lys Ala Ser Thr Ala Thr Ala Glu Gln Phe Phe Gln Lys
65                  70                  75                  80

Leu Arg Asn Lys His Glu Phe Thr Ile Leu Val Thr Leu Lys Gln Thr
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Val Arg Leu His
        115                 120                 125

Tyr Arg Ser Gly Ser His Arg Pro His Thr Glu Val Phe Pro Tyr Ile
    130                 135                 140

Leu Ala Asp Asp Lys Trp His Lys Leu Ser Leu Ala Ile Ser Ala Ser
145                 150                 155                 160

His Leu Ile Leu His Ile Asp Cys Asn Lys Ile Tyr Glu Arg Val Val
                165                 170                 175

Glu Lys Pro Ser Thr Asp Leu Pro Leu Gly Thr Thr Phe Trp Leu Gly
            180                 185                 190

Gln Arg Asn Asn Ala His Gly Tyr Phe Lys Gly Ile Met Gln Asp Val
        195                 200                 205

Gln Leu Leu Val Met Pro Gln Gly Phe Ile Ala Gln Cys Pro Asp Leu
    210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ala Lys Thr Ser Ala Lys Leu Ser
                245                 250                 255
```

-continued

```
Arg Ala Glu Gln Arg Met Asn Arg Leu Asp Gln Cys Tyr Cys Glu Arg
            260                 265                 270

Thr Cys Thr Met Lys Gly Thr Thr Tyr Arg Glu Phe Glu Ser Trp Ile
            275                 280                 285

Asp Gly Cys Lys Asn Cys Thr Cys Leu Asn Gly Thr Ile Gln Cys Glu
            290                 295                 300

Thr Leu Ile Cys Pro Asn Pro Asp Cys Pro Leu Lys Ser Ala Leu Ala
305                 310                 315                 320

Tyr Val Asp Gly Lys Cys Lys Glu Cys Lys Ser Ile Cys Gln Phe
                325                 330                 335

Gln Gly Arg Thr Tyr Phe Glu Gly Glu Arg Asn Thr Val Tyr Ser Ser
            340                 345                 350

Ser Gly Val Cys Val Leu Tyr Glu Cys Lys Asp Gln Thr Met Lys Leu
            355                 360                 365

Val Glu Ser Ser Gly Cys Pro Ala Leu Asp Cys Pro Glu Ser His Gln
            370                 375                 380

Ile Thr Leu Ser His Ser Cys Cys Lys Val Cys Lys Gly Tyr Asp Phe
385                 390                 395                 400

Cys Ser Glu Arg His Asn Cys Met Glu Asn Ser Ile Cys Arg Asn Leu
                405                 410                 415

Asn Asp Arg Ala Val Cys Ser Cys Arg Asp Gly Phe Arg Ala Leu Arg
                420                 425                 430

Glu Asp Asn Ala Tyr Cys Glu Asp Ile Asp Glu Cys Ala Glu Gly Arg
            435                 440                 445

His Tyr Cys Arg Glu Asn Thr Met Cys Val Asn Thr Pro Gly Ser Phe
            450                 455                 460

Met Cys Ile Cys Lys Thr Gly Tyr Ile Arg Ile Asp Asp Tyr Ser Cys
465                 470                 475                 480

Thr Glu His Asp Glu Cys Ile Thr Asn Gln His Asn Cys Asp Glu Asn
                485                 490                 495

Ala Leu Cys Phe Asn Thr Val Gly Gly His Asn Cys Val Cys Lys Pro
            500                 505                 510

Gly Tyr Thr Gly Asn Gly Thr Thr Cys Lys Ala Phe Cys Lys Asp Gly
            515                 520                 525

Cys Arg Asn Gly Gly Ala Cys Ile Ala Ala Asn Val Cys Ala Cys Pro
            530                 535                 540

Gln Gly Phe Thr Gly Pro Ser Cys Glu Thr Asp Ile Asp Glu Cys Ser
545                 550                 555                 560

Asp Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
            580                 585                 590

Phe Ser Pro Ser Gly Glu Ser Cys Glu Asp Ile Asp Glu Cys Gly Thr
            595                 600                 605

Gly Arg His Ser Cys Ala Asn Asp Thr Ile Cys Phe Asn Leu Asp Gly
            610                 615                 620

Gly Tyr Asp Cys Arg Cys Pro His Gly Lys Asn Cys Thr Gly Asp Cys
625                 630                 635                 640

Ile His Asp Gly Lys Val Lys His Asn Gly Gln Ile Trp Val Leu Glu
                645                 650                 655

Asn Asp Arg Cys Ser Val Cys Ser Cys Gln Asn Gly Phe Val Met Cys
            660                 665                 670

Arg Arg Met Val Cys Asp Cys Glu Asn Pro Thr Val Asp Leu Phe Cys
            675                 680                 685
```

```
Cys Pro Glu Cys Asp Pro Arg Leu Ser Ser Gln Cys Leu His Gln Asn
        690                 695                 700

Gly Glu Thr Leu Tyr Asn Ser Gly Asp Thr Trp Val Gln Asn Cys Gln
705                 710                 715                 720

Gln Cys Arg Cys Leu Gln Gly Glu Val Asp Cys Trp Pro Leu Pro Cys
                725                 730                 735

Pro Asp Val Glu Cys Glu Phe Ser Ile Leu Pro Glu Asn Glu Cys Cys
            740                 745                 750

Pro Arg Cys Val Thr Asp Pro Cys Gln Ala Asp Thr Ile Arg Asn Asp
            755                 760                 765

Ile Thr Lys Thr Cys Leu Asp Glu Met Asn Val Val Arg Phe Thr Gly
    770                 775                 780

Ser Ser Trp Ile Lys His Gly Thr Glu Cys Thr Leu Cys Gln Cys Lys
785                 790                 795                 800

Asn Gly His Ile Cys Cys Ser Val Asp Pro Gln Cys Leu Gln Glu Leu
                805                 810                 815

<210> SEQ ID NO 38
<211> LENGTH: 2448
<212> TYPE: DNA
<213> ORGANISM: Homo sapiens

<400> SEQUENCE: 38
atggagtctc gggtcttact gagaacattc tgtttgatct tcggtctcgg agcagtttgg      60
gggcttggtg tggacccttc cctacagatt gacgtcttaa cagagttaga acttggggag     120
tccacgaccg gagtgcgtca ggtcccgggg ctgcataatg ggacgaaagc ctttctcttt     180
caagatactc ccagaagcat aaaagcatcc actgctacag ctgaacagtt ttttcagaag     240
ctgagaaata acatgaattt actattttg gtgaccctaa acagaccca cttaaattca      300 ggagttattc tctcaattca ccacttggat cacaggtacc tggaactgga agtagtggc      360 catcggaatg aagtcagact gcattaccgc tcaggcagtc accgccctca cacagaagtg     420
tttccttaca ttttggctga tgacaagtgg cacaagctct ccttagccat cagtgcttcc     480
catttgattt tacacattga ctgcaataaa atttatgaaa gggtagtaga aaagccctcc     540
acagacttgc tctaggcac aacattttgg ctaggacaga gaataatgc gcatggatat      600 tttaagggta atgcaaga tgtccaatta cttgtcatgc cccagggatt tattgctcag      660
tgcccagatc ttaatcgcac ctgtccaact gcaatgact tccatggact tgtgcagaaa      720
atcatggagc tacaggatat tttagccaaa acatcagcca agctgtctcg agctgaacag     780
cgaatgaata gattggatca gtgctattgt gaaaggactt gcaccatgaa gggaaccacc     840
taccgagaat tgagtcctg gatagacggc tgtaagaact gcacatgcct gaatggaacc      900
atccagtgtg aaactctaat ctgcccaaat cctgactgcc acttaagtc ggctcttgcg      960 tatgtggatg gcaaatgctg taggaatgc aaatcgatat gccaattca aggacgaacc     1020 tactttgaag gagaaagaaa tacagtctat tcctcttctg gagtatgtgt tctctatgag     1080
tgcaaggacc agaccatgaa acttgttgag agttcaggct gtccagcttt ggattgtcca     1140
gagtctcatc agataacctt gtctcacagc tgttgcaaag tttgtaaagg ttatgacttt     1200
tgttctgaaa ggcataactg catggagaat tccatctgca gaaatctgaa tgacagggct     1260
gtttgtagct gtcgagatgg ttttagggct cttcgagagg ataatgccta ctgtgaagac     1320
atcgatgagt gtgctgaagg cgccattac tgtcgtgaaa atacaatgtg tgtcaacacc      1380
ccgggttctt ttatgtgcat ctgcaaaact ggatacatca gaattgatga ttattcatgt     1440
```

-continued

```
acagaacatg atgagtgtat cacaaatcag cacaactgtg atgaaaatgc tttatgcttc    1500
aacactgttg gaggacacaa ctgtgtttgc aagccgggct atacagggaa tggaacgaca    1560
tgcaaagcat tttgcaaaga tggctgtagg aatggaggag cctgtattgc cgctaatgtg    1620
tgtgcctgcc cacaaggctt cactggaccc agctgtgaaa cggacattga tgaatgctct    1680
gatggttttg ttcaatgtga cagtcgtgct aattgcatta acctgcctgg atggtaccac    1740
tgtgagtgca gagatggcta ccatgacaat gggatgtttt caccaagtgg agaatcgtgt    1800
gaagatattg atgagtgtgg gaccggggag cacagctgtg ccaatgatac catttgcttc    1860
aatttggatg gcggatatga ttgtcgatgt cctcatggaa agaattgcac aggggactgc    1920
atccatgatg gaaaagttaa gcacaatggt cagatttggg tgttggaaaa tgacaggtgc    1980
tctgtgtgct catgtcagaa tggattcgtt atgtgtcgac ggatggtctg tgactgtgag    2040
aatcccacag ttgatctttt ttgctgccct gaatgtgacc caaggcttag tagtcagtgc    2100
ctccatcaaa atggggaaac tttgtataac agtggtgaca cctgggtcca gaattgtcaa    2160
cagtgccgct gcttgcaagg ggaagttgat tgttggcccc tgccttgccc agatgtggag    2220
tgtgaattca gcattctccc agagaatgag tgctgcccgc gctgtgtcac agacccttgc    2280
caggctgaca ccatccgcaa tgacatcacc aagacttgcc tggacgaaat gaatgtggtt    2340
cgcttcaccg gtcctcttg gatcaaacat ggcactgagt gtactctctg ccagtgcaag    2400
aatggccaca tctgttgctc agtggatcca cagtgccttc aggaactg               2448
```

```
<210> SEQ ID NO 39
<211> LENGTH: 3198
<212> TYPE: DNA
<213> ORGANISM: Homo sapiens
<220> FEATURE:
<221> NAME/KEY: CDS
<222> LOCATION: (97)..(2544)

<400> SEQUENCE: 39
ttgggaggag cagtctctcc gctcgtctcc cggagctttc tccattgtct ctgcctttac      60
aacagaggga gacgatggac tgagctgatc cgcacc atg gag tct cgg gtc tta      114
                                       Met Glu Ser Arg Val Leu
                                         1               5 ctg aga aca ttc tgt ttg atc ttc ggt ctc gga gca gtt tgg ggg ctt      162
Leu Arg Thr Phe Cys Leu Ile Phe Gly Leu Gly Ala Val Trp Gly Leu
         10                  15                  20 ggt gtg gac cct tcc cta cag att gac gtc tta aca gag tta gaa ctt      210
Gly Val Asp Pro Ser Leu Gln Ile Asp Val Leu Thr Glu Leu Glu Leu
     25                  30                  35 ggg gag tcc acg acc gga gtg cgt cag gtc ccg ggg ctg cat aat ggg      258
Gly Glu Ser Thr Thr Gly Val Arg Gln Val Pro Gly Leu His Asn Gly
 40                  45                  50 acg aaa gcc ttt ctc ttt caa gat act ccc aga agc ata aaa gca tcc      306
Thr Lys Ala Phe Leu Phe Gln Asp Thr Pro Arg Ser Ile Lys Ala Ser
 55                  60                  65                  70 act gct aca gct gaa cag ttt ttt cag aag ctg aga aat aaa cat gaa      354
Thr Ala Thr Ala Glu Gln Phe Phe Gln Lys Leu Arg Asn Lys His Glu
             75                  80                  85 ttt act att ttg gtg acc cta aaa cag acc cac tta aat tca gga gtt      402
Phe Thr Ile Leu Val Thr Leu Lys Gln Thr His Leu Asn Ser Gly Val
         90                  95                 100 att ctc tca att cac cac ttg gat cac agg tac ctg gaa ctg gaa agt      450
Ile Leu Ser Ile His His Leu Asp His Arg Tyr Leu Glu Leu Glu Ser
        105                 110                 115
```

-continued

```
agt ggc cat cgg aat gaa gtc aga ctg cat tac cgc tca ggc agt cac      498
Ser Gly His Arg Asn Glu Val Arg Leu His Tyr Arg Ser Gly Ser His
        120                 125                 130 cgc cct cac aca gaa gtg ttt cct tac att ttg gct gat gac aag tgg      546
Arg Pro His Thr Glu Val Phe Pro Tyr Ile Leu Ala Asp Asp Lys Trp
135                 140                 145                 150 cac aag ctc tcc tta gcc atc agt gct tcc cat ttg att tta cac att      594
His Lys Leu Ser Leu Ala Ile Ser Ala Ser His Leu Ile Leu His Ile
                155                 160                 165 gac tgc aat aaa att tat gaa agg gta gta gaa aag ccc tcc aca gac      642
Asp Cys Asn Lys Ile Tyr Glu Arg Val Val Glu Lys Pro Ser Thr Asp
        170                 175                 180 ttg cct cta ggc aca aca ttt tgg cta gga cag aga aat aat gcg cat      690
Leu Pro Leu Gly Thr Thr Phe Trp Leu Gly Gln Arg Asn Asn Ala His
            185                 190                 195 gga tat ttt aag ggt ata atg caa gat gtc caa tta ctt gtc atg ccc      738
Gly Tyr Phe Lys Gly Ile Met Gln Asp Val Gln Leu Leu Val Met Pro
        200                 205                 210 cag gga ttt att gct cag tgc cca gat ctt aat cgc acc tgt cca act      786
Gln Gly Phe Ile Ala Gln Cys Pro Asp Leu Asn Arg Thr Cys Pro Thr
215                 220                 225                 230 tgc aat gac ttc cat gga ctt gtg cag aaa atc atg gag cta cag gat      834
Cys Asn Asp Phe His Gly Leu Val Gln Lys Ile Met Glu Leu Gln Asp
                235                 240                 245 att tta gcc aaa aca tca gcc aag ctg tct cga gct gaa cag cga atg      882
Ile Leu Ala Lys Thr Ser Ala Lys Leu Ser Arg Ala Glu Gln Arg Met
        250                 255                 260 aat aga ttg gat cag tgc tat tgt gaa agg act tgc acc atg aag gga      930
Asn Arg Leu Asp Gln Cys Tyr Cys Glu Arg Thr Cys Thr Met Lys Gly
            265                 270                 275 acc acc tac cga gaa ttt gag tcc tgg ata gac ggc tgt aag aac tgc      978
Thr Thr Tyr Arg Glu Phe Glu Ser Trp Ile Asp Gly Cys Lys Asn Cys
        280                 285                 290 aca tgc ctg aat gga acc atc cag tgt gaa act cta atc tgc cca aat     1026
Thr Cys Leu Asn Gly Thr Ile Gln Cys Glu Thr Leu Ile Cys Pro Asn
295                 300                 305                 310 cct gac tgc cca ctt aag tcg gct ctt gcg tat gtg gat ggc aaa tgc     1074
Pro Asp Cys Pro Leu Lys Ser Ala Leu Ala Tyr Val Asp Gly Lys Cys
                315                 320                 325 tgt aag gaa tgc aaa tcg ata tgc caa ttt caa gga cga acc tac ttt     1122
Cys Lys Glu Cys Lys Ser Ile Cys Gln Phe Gln Gly Arg Thr Tyr Phe
        330                 335                 340 gaa gga gaa aga aat aca gtc tat tcc tct tct gga gta tgt gtt ctc     1170
Glu Gly Glu Arg Asn Thr Val Tyr Ser Ser Ser Gly Val Cys Val Leu
            345                 350                 355 tat gag tgc aag gac cag acc atg aaa ctt gtt gag agt tca ggc tgt     1218
Tyr Glu Cys Lys Asp Gln Thr Met Lys Leu Val Glu Ser Ser Gly Cys
        360                 365                 370 cca gct ttg gat tgt cca gag tct cat cag ata acc ttg tct cac agc     1266
Pro Ala Leu Asp Cys Pro Glu Ser His Gln Ile Thr Leu Ser His Ser
375                 380                 385                 390 tgt tgc aaa gtt tgt aaa ggt tat gac ttt tgt tct gaa agg cat aac     1314
Cys Cys Lys Val Cys Lys Gly Tyr Asp Phe Cys Ser Glu Arg His Asn
                395                 400                 405 tgc atg gag aat tcc atc tgc aga aat ctg aat gac agg gct gtt tgt     1362
Cys Met Glu Asn Ser Ile Cys Arg Asn Leu Asn Asp Arg Ala Val Cys
        410                 415                 420 agc tgt cga gat ggt ttt agg gct ctt cga gag gat aat gcc tac tgt     1410
Ser Cys Arg Asp Gly Phe Arg Ala Leu Arg Glu Asp Asn Ala Tyr Cys
            425                 430                 435
```

-continued

```
gaa gac atc gat gag tgt gct gaa ggg cgc cat tac tgt cgt gaa aat          1458
Glu Asp Ile Asp Glu Cys Ala Glu Gly Arg His Tyr Cys Arg Glu Asn
440                 445                 450 aca atg tgt gtc aac acc ccg ggt tct ttt atg tgc atc tgc aaa act          1506
Thr Met Cys Val Asn Thr Pro Gly Ser Phe Met Cys Ile Cys Lys Thr
455                 460                 465                 470 gga tac atc aga att gat gat tat tca tgt aca gaa cat gat gag tgt          1554
Gly Tyr Ile Arg Ile Asp Asp Tyr Ser Cys Thr Glu His Asp Glu Cys
            475                 480                 485 atc aca aat cag cac aac tgt gat gaa aat gct tta tgc ttc aac act          1602
Ile Thr Asn Gln His Asn Cys Asp Glu Asn Ala Leu Cys Phe Asn Thr
490                 495                 500 gtt gga gga cac aac tgt gtt tgc aag ccg ggc tat aca ggg aat gga          1650
Val Gly Gly His Asn Cys Val Cys Lys Pro Gly Tyr Thr Gly Asn Gly
    505                 510                 515 acg aca tgc aaa gca ttt tgc aaa gat ggc tgt agg aat gga gga gcc          1698
Thr Thr Cys Lys Ala Phe Cys Lys Asp Gly Cys Arg Asn Gly Gly Ala
520                 525                 530 tgt att gcc gct aat gtg tgt gcc tgc cca caa ggc ttc act gga ccc          1746
Cys Ile Ala Ala Asn Val Cys Ala Cys Pro Gln Gly Phe Thr Gly Pro
535                 540                 545                 550 agc tgt gaa acg gac att gat gaa tgc tct gat ggt ttt gtt caa tgt          1794
Ser Cys Glu Thr Asp Ile Asp Glu Cys Ser Asp Gly Phe Val Gln Cys
            555                 560                 565 gac agt cgt gct aat tgc att aac ctg cct gga tgg tac cac tgt gag          1842
Asp Ser Arg Ala Asn Cys Ile Asn Leu Pro Gly Trp Tyr His Cys Glu
570                 575                 580 tgc aga gat ggc tac cat gac aat ggg atg ttt tca cca agt gga gaa          1890
Cys Arg Asp Gly Tyr His Asp Asn Gly Met Phe Ser Pro Ser Gly Glu
    585                 590                 595 tcg tgt gaa gat att gat gag tgt ggg acc ggg agg cac agc tgt gcc          1938
Ser Cys Glu Asp Ile Asp Glu Cys Gly Thr Gly Arg His Ser Cys Ala
600                 605                 610 aat gat acc att tgc ttc aat ttg gat ggc gga tat gat tgt cga tgt          1986
Asn Asp Thr Ile Cys Phe Asn Leu Asp Gly Gly Tyr Asp Cys Arg Cys
615                 620                 625                 630 cct cat gga aag aat tgc aca ggg gac tgc atc cat gat gga aaa gtt          2034
Pro His Gly Lys Asn Cys Thr Gly Asp Cys Ile His Asp Gly Lys Val
            635                 640                 645 aag cac aat ggt cag att tgg gtg ttg gaa aat gac agg tgc tct gtg          2082
Lys His Asn Gly Gln Ile Trp Val Leu Glu Asn Asp Arg Cys Ser Val
                650                 655                 660 tgc tca tgt cag aat gga ttc gtt atg tgt cga cgg atg gtc tgt gac          2130
Cys Ser Cys Gln Asn Gly Phe Val Met Cys Arg Arg Met Val Cys Asp
            665                 670                 675 tgt gag aat ccc aca gtt gat ctt ttt tgc tgc cct gaa tgt gac cca          2178
Cys Glu Asn Pro Thr Val Asp Leu Phe Cys Cys Pro Glu Cys Asp Pro
680                 685                 690 agg ctt agt agt cag tgc ctc cat caa aat ggg gaa act ttg tat aac          2226
Arg Leu Ser Ser Gln Cys Leu His Gln Asn Gly Glu Thr Leu Tyr Asn
695                 700                 705                 710 agt ggt gac acc tgg gtc cag aat tgt caa cag tgc cgc tgc ttg caa          2274
Ser Gly Asp Thr Trp Val Gln Asn Cys Gln Gln Cys Arg Cys Leu Gln
            715                 720                 725 ggg gaa gtt gat tgt tgg ccc ctg cct tgc cca gat gtg gag tgt gaa          2322
Gly Glu Val Asp Cys Trp Pro Leu Pro Cys Pro Asp Val Glu Cys Glu
                730                 735                 740 ttc agc att ctc cca gag aat gag tgc tgc ccg cgc tgt gtc aca gac          2370
Phe Ser Ile Leu Pro Glu Asn Glu Cys Cys Pro Arg Cys Val Thr Asp
            745                 750                 755
```

```
cct tgc cag gct gac acc atc cgc aat gac atc acc aag act tgc ctg      2418
Pro Cys Gln Ala Asp Thr Ile Arg Asn Asp Ile Thr Lys Thr Cys Leu
760                 765                 770 gac gaa atg aat gtg gtt cgc ttc acc ggg tcc tct tgg atc aaa cat      2466
Asp Glu Met Asn Val Val Arg Phe Thr Gly Ser Ser Trp Ile Lys His
775                 780                 785                 790 ggc act gag tgt act ctc tgc cag tgc aag aat ggc cac atc tgt tgc      2514
Gly Thr Glu Cys Thr Leu Cys Gln Cys Lys Asn Gly His Ile Cys Cys
                795                 800                 805 tca gtg gat cca cag tgc ctt cag gaa ctg tgaagttaac tgtctcatgg        2564
Ser Val Asp Pro Gln Cys Leu Gln Glu Leu
            810                 815 gagatttctg ttaaaagaat gttctttcat taaaagacca aaaagaagtt aaaacttaaa    2624
ttgggtgatt tgtgggcagc taaatgcagc tttgttaata gctgagtgaa ctttcaatta    2684
tgaaatttgt ggagcttgac aaaatcacaa aaggaaaatt actgggcaa aattagacct     2744 caagtctgcc tctactgtgt ctcacatcac catgtagaag aatgggcgta cagtatatac    2804
cgtgacatcc tgaaccctgg atagaaagcc tgagcccatt ggatctgtga agcctctag     2864 cttcactggt gcagaaaatt ttcctctaga tcagaatctt cagaatcagt taggttcctc    2924
actgcaagaa ataaaatgtc aggcagtgaa tgaattatat tttcagaagt aaagcaaaga    2984
agctataaca tgttatgtac agtacactct gaaaagaaat ctgaaacaag ttattgtaat    3044
gataaaaata atgcacaggc atggttactt aatattttct aacaggaaaa gtcatcccta    3104
tttccttgtt ttactgcact taatattatt tggttgaatt tgttcagtat aagctcgttc    3164
ttgtgcaaaa ttaaataaat atttctctta cctt                                3198
```

<210> SEQ ID NO 40
<211> LENGTH: 499
<212> TYPE: PRT
<213> ORGANISM: Homo sapiens

<400> SEQUENCE: 40

```
Met Glu Leu Ser Glu Pro Val Val Glu Asn Gly Glu Val Glu Met Ala
1               5                   10                  15

Leu Glu Glu Ser Trp Glu His Ser Lys Glu Val Ser Glu Ala Glu Pro
            20                  25                  30

Gly Gly Gly Ser Ser Gly Asp Ser Gly Pro Pro Glu Glu Ser Gly Gln
        35                  40                  45

Glu Met Met Glu Glu Lys Glu Glu Ile Arg Lys Ser Lys Ser Val Ile
    50                  55                  60

Val Pro Ser Gly Ala Pro Lys Lys Glu His Val Asn Val Val Phe Ile
65                  70                  75                  80

Gly His Val Asp Ala Gly Lys Ser Thr Ile Gly Gly Gln Ile Met Phe
                85                  90                  95

Leu Thr Gly Met Ala Asp Lys Arg Thr Leu Glu Lys Tyr Glu Arg Glu
            100                 105                 110

Ala Glu Glu Lys Asn Arg Glu Thr Trp Tyr Leu Ser Trp Ala Leu Asp
        115                 120                 125

Thr Asn Gln Glu Glu Arg Asp Lys Gly Lys Thr Val Glu Val Gly Arg
    130                 135                 140

Ala Tyr Phe Glu Thr Glu Arg Lys His Phe Thr Ile Leu Asp Ala Pro
145                 150                 155                 160

Gly His Lys Ser Phe Val Pro Asn Met Ile Gly Gly Ala Ser Gln Ala
                165                 170                 175

Asp Leu Ala Val Leu Val Ile Ser Ala Arg Lys Gly Glu Phe Glu Thr
```

```
                            180                 185                 190
Gly Phe Glu Lys Gly Gly Gln Thr Arg Glu His Ala Met Phe Gly Lys
            195                 200                 205

Thr Ala Gly Val Lys His Leu Ile Val Leu Ile Asn Lys Met Asp Asp
        210                 215                 220

Pro Thr Val Asn Trp Gly Ile Glu Arg Tyr Glu Cys Lys Glu Lys
225                 230                 235                 240

Leu Val Pro Phe Leu Lys Lys Val Gly Phe Ser Pro Lys Asp Ile
                245                 250                 255

His Phe Met Pro Cys Ser Gly Leu Thr Gly Ala Asn Ile Lys Glu Gln
            260                 265                 270

Ser Asp Phe Cys Pro Trp Tyr Thr Gly Leu Pro Phe Ile Pro Tyr Leu
        275                 280                 285

Asn Asn Leu Pro Asn Phe Asn Arg Ser Ile Asp Gly Pro Ile Arg Leu
    290                 295                 300

Pro Ile Val Asp Lys Tyr Lys Asp Met Gly Thr Val Val Leu Gly Lys
305                 310                 315                 320

Leu Glu Ser Gly Ser Ile Phe Lys Gly Gln Gln Leu Val Met Met Pro
                325                 330                 335

Asn Lys His Asn Val Glu Val Leu Gly Ile Leu Ser Asp Asp Thr Glu
            340                 345                 350

Thr Asp Phe Val Ala Pro Gly Glu Asn Leu Lys Ile Arg Leu Lys Gly
        355                 360                 365

Ile Glu Glu Glu Glu Ile Leu Pro Gly Phe Ile Leu Cys Asp Pro Ser
    370                 375                 380

Asn Leu Cys His Ser Gly Arg Thr Phe Asp Val Gln Ile Val Ile Ile
385                 390                 395                 400

Glu His Lys Ser Ile Ile Cys Pro Gly Tyr Asn Ala Val Leu His Ile
                405                 410                 415

His Thr Cys Ile Glu Val Gly Ile Thr Ala Leu Ile Ser Leu Val
            420                 425                 430

Asp Lys Lys Ser Gly Glu Lys Ser Lys Thr Arg Pro Arg Phe Val Lys
        435                 440                 445

Gln Asp Gln Val Cys Ile Ala Arg Leu Arg Thr Ala Gly Thr Ile Cys
    450                 455                 460

Leu Glu Thr Phe Lys Asp Phe Pro Gln Met Gly Arg Phe Thr Leu Arg
465                 470                 475                 480

Asp Glu Gly Lys Thr Ile Ala Ile Gly Lys Val Leu Lys Leu Val Pro
                485                 490                 495

Glu Lys Asp

<210> SEQ ID NO 41
<211> LENGTH: 1497
<212> TYPE: DNA
<213> ORGANISM: Homo sapiens

<400> SEQUENCE: 41
atggaacttt cagaacctgt tgtagaaaat ggagaggtgg aaatggccct agaagaatca      60
tgggagcaca gtaaagaagt aagtgaagcc gagcctgggg gtggttcctc gggagattca    120
gggcccccag aagaaagtgg ccaggaaatg atggaggaaa agaggaaat aagaaaatcc     180 aaatctgtga tcgtacccte aggtgcacct aagaagaac acgtaaatgt agtattcatt    240
ggccatgtag acgctggcaa gtcaaccatc ggaggacaga taatgttttt gactggaatg    300
gctgacaaaa gaacactgga gaaatatgaa agagaagctg aggaaaaaaa cagagaaacc    360
```

```
tggtatttgt cctgggcctt agatacaaat caggaggaac gagacaaggg taaaacagtc    420
gaagtgggtc gtgcctattt tgaaacagaa aggaaacatt tcacaatttt agatgcccct    480
ggccacaaga gttttgtccc aaatatgatt ggtggtgctt ctcaagctga tttggctgtg    540
ctggtcatct ctgccaggaa aggagagttt gaaactggat ttgaaaaagg tggacagaca    600
agagaacatg cgatgtttgg caaaacggca ggagtaaaac atttaatagt gcttattaat    660
aagatggatg atcccacagt aaattggggc atcgagagat atgaagaatg taaagaaaaa    720
ctggtgccct ttttgaaaaa agtaggcttt agtccaaaaa aggacattca ctttatgccc    780
tgctcaggac tgaccggagc aaatattaaa gagcagtcag atttctgccc ttggtacact    840
ggattaccat ttattccgta tttgaataac ttgccaaact tcaacagatc aattgatgga    900
ccaataagac tgccaattgt ggataagtac aaagatatgg gcactgtggt cctgggaaag    960
ctggaatccg ggtccatttt taaaggccag cagctcgtga tgatgccaaa caagcacaat   1020
gtagaagttc ttggaatact ttctgatgat actgaaactg attttgtagc cccaggtgaa   1080
aacctcaaaa tcagactgaa gggaattgaa gaagaagaga tcttccagaa attcatactt   1140
tgtgatccta gtaacctctg ccattctgga cgcacgtttg atgttcagat agtgattatt   1200
gagcacaaat ccatcatctg cccaggttat aatgcggtgc tgcacattca tacttgtatt   1260
gaggaagttg agataacagc gttaatctcc ttggtagaca aaaaatcagg ggaaaaagt   1320 aagacacgac cccgcttcgt gaaacaagat caagtatgca ttgctcgttt aaggacagca   1380
ggaaccatct gcctcgagac gttcaaagat tttcctcaga tgggtcgttt tactttaaga   1440
gatgagggta agaccattgc aattggaaaa gttctgaaat tggtcccaga gaaggac      1497

<210> SEQ ID NO 42
<211> LENGTH: 2057
<212> TYPE: DNA
<213> ORGANISM: Homo sapiens
<220> FEATURE:
<221> NAME/KEY: CDS
<222> LOCATION: (144)..(1640)

<400> SEQUENCE: 42
tcccggccgg ctccggcagc aacgatgaag cctgcaccgg cgcgggatac cctcaaggta     60
aaaggatggg acgggggggca cctgtggaac cttcccgaga ggaaccgtta gtgtcgcttg    120
aaggttccaa ttcagccgtt acc atg gaa ctt tca gaa cct gtt gta gaa aat    173
                            Met Glu Leu Ser Glu Pro Val Val Glu Asn
                             1               5                  10 gga gag gtg gaa atg gcc cta gaa gaa tca tgg gag cac agt aaa gaa      221
Gly Glu Val Glu Met Ala Leu Glu Glu Ser Trp Glu His Ser Lys Glu
            15                  20                  25 gta agt gaa gcc gag cct ggg ggt ggt tcc tcg gga gat tca ggg ccc      269
Val Ser Glu Ala Glu Pro Gly Gly Gly Ser Ser Gly Asp Ser Gly Pro
        30                  35                  40 cca gaa gaa agt ggc cag gaa atg atg gag gaa aaa gag gaa ata aga      317
Pro Glu Glu Ser Gly Gln Glu Met Met Glu Glu Lys Glu Glu Ile Arg
    45                  50                  55 aaa tcc aaa tct gtg atc gta ccc tca ggt gca cct aag aaa gaa cac      365
Lys Ser Lys Ser Val Ile Val Pro Ser Gly Ala Pro Lys Lys Glu His
60                  65                  70 gta aat gta gta ttc att ggc cat gta gac gct ggc aag tca acc atc      413
Val Asn Val Val Phe Ile Gly His Val Asp Ala Gly Lys Ser Thr Ile
        75                  80                  85                  90 gga gga cag ata atg ttt ttg act gga atg gct gac aaa aga aca ctg      461
Gly Gly Gln Ile Met Phe Leu Thr Gly Met Ala Asp Lys Arg Thr Leu
```

```
                         95                  100                 105
gag aaa tat gaa aga gaa gct gag gaa aaa aac aga gaa acc tgg tat       509
Glu Lys Tyr Glu Arg Glu Ala Glu Glu Lys Asn Arg Glu Thr Trp Tyr
            110                 115                 120 ttg tcc tgg gcc tta gat aca aat cag gag gaa cga gac aag ggt aaa       557
Leu Ser Trp Ala Leu Asp Thr Asn Gln Glu Glu Arg Asp Lys Gly Lys
            125                 130                 135 aca gtc gaa gtg ggt cgt gcc tat ttt gaa aca gaa agg aaa cat ttc       605
Thr Val Glu Val Gly Arg Ala Tyr Phe Glu Thr Glu Arg Lys His Phe
        140                 145                 150 aca att tta gat gcc cct ggc cac aag agt ttt gtc cca aat atg att       653
Thr Ile Leu Asp Ala Pro Gly His Lys Ser Phe Val Pro Asn Met Ile
155                 160                 165                 170 ggt ggt gct tct caa gct gat ttg gct gtg ctg gtc atc tct gcc agg       701
Gly Gly Ala Ser Gln Ala Asp Leu Ala Val Leu Val Ile Ser Ala Arg
                175                 180                 185 aaa gga gag ttt gaa act gga ttt gaa aaa ggt gga cag aca aga gaa       749
Lys Gly Glu Phe Glu Thr Gly Phe Glu Lys Gly Gly Gln Thr Arg Glu
            190                 195                 200 cat gcg atg ttt ggc aaa acg gca gga gta aaa cat tta ata gtg ctt       797
His Ala Met Phe Gly Lys Thr Ala Gly Val Lys His Leu Ile Val Leu
            205                 210                 215 att aat aag atg gat gat ccc aca gta aat tgg ggc atc gag aga tat       845
Ile Asn Lys Met Asp Asp Pro Thr Val Asn Trp Gly Ile Glu Arg Tyr
220                 225                 230 gaa gaa tgt aaa gaa aaa ctg gtg ccc ttt ttg aaa aaa gta ggc ttt       893
Glu Glu Cys Lys Glu Lys Leu Val Pro Phe Leu Lys Lys Val Gly Phe
235                 240                 245                 250 agt cca aaa aag gac att cac ttt atg ccc tgc tca gga ctg acc gga       941
Ser Pro Lys Lys Asp Ile His Phe Met Pro Cys Ser Gly Leu Thr Gly
                255                 260                 265 gca aat att aaa gag cag tca gat ttc tgc cct tgg tac act gga tta       989
Ala Asn Ile Lys Glu Gln Ser Asp Phe Cys Pro Trp Tyr Thr Gly Leu
            270                 275                 280 cca ttt att ccg tat ttg aat aac ttg cca aac ttc aac aga tca att      1037
Pro Phe Ile Pro Tyr Leu Asn Asn Leu Pro Asn Phe Asn Arg Ser Ile
            285                 290                 295 gat gga cca ata aga ctg cca att gtg gat aag tac aaa gat atg ggc      1085
Asp Gly Pro Ile Arg Leu Pro Ile Val Asp Lys Tyr Lys Asp Met Gly
300                 305                 310 act gtg gtc ctg gga aag ctg gaa tcc ggg tcc att ttt aaa ggc cag      1133
Thr Val Val Leu Gly Lys Leu Glu Ser Gly Ser Ile Phe Lys Gly Gln
315                 320                 325                 330 cag ctc gtg atg atg cca aac aag cac aat gta gaa gtt ctt gga ata      1181
Gln Leu Val Met Met Pro Asn Lys His Asn Val Glu Val Leu Gly Ile
                335                 340                 345 ctt tct gat gat act gaa act gat ttt gta gcc cca ggt gaa aac ctc      1229
Leu Ser Asp Asp Thr Glu Thr Asp Phe Val Ala Pro Gly Glu Asn Leu
            350                 355                 360 aaa atc aga ctg aag gga att gaa gaa gaa gag att ctt cca gaa ttc      1277
Lys Ile Arg Leu Lys Gly Ile Glu Glu Glu Glu Ile Leu Pro Glu Phe
            365                 370                 375 ata ctt tgt gat cct agt aac ctc tgc cat tct gga cgc acg ttt gat      1325
Ile Leu Cys Asp Pro Ser Asn Leu Cys His Ser Gly Arg Thr Phe Asp
        380                 385                 390 gtt cag ata gtg att att gag cac aaa tcc atc atc tgc cca ggt tat      1373
Val Gln Ile Val Ile Ile Glu His Lys Ser Ile Ile Cys Pro Gly Tyr
395                 400                 405                 410 aat gcg gtg ctg cac att cat act tgt att gag gaa gtt gag ata aca      1421
Asn Ala Val Leu His Ile His Thr Cys Ile Glu Glu Val Glu Ile Thr
```

```
                     415                 420                 425
gcg tta atc tcc ttg gta gac aaa aaa tca ggg gaa aaa agt aag aca        1469
Ala Leu Ile Ser Leu Val Asp Lys Lys Ser Gly Glu Lys Ser Lys Thr
            430                 435                 440 cga ccc cgc ttc gtg aaa caa gat caa gta tgc att gct cgt tta agg        1517
Arg Pro Arg Phe Val Lys Gln Asp Gln Val Cys Ile Ala Arg Leu Arg
                445                 450                 455 aca gca gga acc atc tgc ctc gag acg ttc aaa gat ttt cct cag atg        1565
Thr Ala Gly Thr Ile Cys Leu Glu Thr Phe Lys Asp Phe Pro Gln Met
        460                 465                 470 ggt cgt ttt act tta aga gat gag ggt aag acc att gca att gga aaa        1613
Gly Arg Phe Thr Leu Arg Asp Glu Gly Lys Thr Ile Ala Ile Gly Lys
475                 480                 485                 490 gtt ctg aaa ttg gtc cca gag aag gac taagcaattt tcttgatgcc             1660
Val Leu Lys Leu Val Pro Glu Lys Asp
                495 tctgcaagat actgtgagga gaattgacag caaaagttca ccacctactc ttatttactg     1720 cccattgatt gactttctt catatttgc aaagagaaat tcacagcaa aaattcatgt        1780 tttgtcagct ttctcatgtt gagatctgtt atgtcactga tgaatttacc ctcaagtttc     1840 cttcctctgt accactctgc ttccttggac aatatcagta atagctttgt aagtgatgtg     1900 gacgtaattg cctacagtaa taaaaaaata atgtacttta atttttcatt ttcttttagg     1960 atatttagac caccttgtt ccacgcaaac cagagtgtgt cagtgtttgt gtgtgtgtta      2020 aaatgataac taacatgtga ataaaatact ccatttg                              2057

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Primer P1

<400> SEQUENCE: 43
acaccaatcc agtagccagg cttg                                              24

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Primer P2

<400> SEQUENCE: 44
cactcgagaa tctgtgagac ctacatacat gacg                                   34

<210> SEQ ID NO 45
<211> LENGTH: 21
<212> TYPE: PRT
<213> ORGANISM: Artificial Sequence
<220> FEATURE:
<221> NAME/KEY: misc_feature
<222> LOCATION: (2)..(20)
<223> OTHER INFORMATION: Xaa can be any naturally occurring amino acid

<400> SEQUENCE: 45

Cys Xaa Glu Cys Gly Lys Ala Phe Xaa Gln Lys Ser Xaa Leu Xaa Xaa
  1               5                  10                  15

His Gln Arg Xaa His
             20

<210> SEQ ID NO 46
```

```
<211> LENGTH: 7
<212> TYPE: PRT
<213> ORGANISM: Bovine sp.

<400> SEQUENCE: 46

Val Leu Asn Ile Ser Leu Trp
 1               5

<210> SEQ ID NO 47
<211> LENGTH: 17
<212> TYPE: PRT
<213> ORGANISM: Bovine sp.

<400> SEQUENCE: 47

Thr Leu Met Glu Leu Leu Asn Gln Met Asp Gly Phe Asp Thr Leu His
 1               5                  10                  15

Arg

<210> SEQ ID NO 48
<211> LENGTH: 14
<212> TYPE: PRT
<213> ORGANISM: Bovine sp.
<220> FEATURE:
<221> NAME/KEY: misc_feature
<222> LOCATION: (11)..(13)
<223> OTHER INFORMATION: Xaa can be any naturally occurring amino acid

<400> SEQUENCE: 48

Ala Val Ser Asp Phe Val Val Ser Glu Tyr Xaa Met Xaa Ala
 1               5                  10

<210> SEQ ID NO 49
<211> LENGTH: 9
<212> TYPE: PRT
<213> ORGANISM: Bovine sp.
<220> FEATURE:
<221> NAME/KEY: misc_feature
<222> LOCATION: (9)..(9)
<223> OTHER INFORMATION: Xaa can be any naturally occurring amino acid

<400> SEQUENCE: 49

Glu Val Asp Pro Leu Val Tyr Asn Xaa
 1               5

<210> SEQ ID NO 50
<211> LENGTH: 11
<212> TYPE: PRT
<213> ORGANISM: Bovine sp.

<400> SEQUENCE: 50

His Gly Glu Ile Asp Tyr Glu Ala Ile Val Lys
 1               5                  10

<210> SEQ ID NO 51
<211> LENGTH: 25
<212> TYPE: PRT
<213> ORGANISM: Bovine sp.
<220> FEATURE:
<221> NAME/KEY: misc_feature
<222> LOCATION: (3)..(23)
<223> OTHER INFORMATION: Xaa can be any naturally occurring amino acid

<400> SEQUENCE: 51

Leu Ser Xaa Gly Phe Asn Gly Ala Asp Leu Arg Asn Val Xaa Thr Glu
 1               5                  10                  15

Ala Gly Met Phe Ala Ile Xaa Ala Asp
             20                  25
```

```
<210> SEQ ID NO 52
<211> LENGTH: 21
<212> TYPE: PRT
<213> ORGANISM: Bovine sp.
<220> FEATURE:
<221> NAME/KEY: misc_feature
<222> LOCATION: (20)..(20)
<223> OTHER INFORMATION: Xaa can be any naturally occurring amino acid

<400> SEQUENCE: 52

Met Ile Met Ala Thr Asn Arg Pro Asp Thr Leu Asp Pro Ala Leu Leu
1               5                   10                  15

Arg Pro Gly Xaa Leu
            20

<210> SEQ ID NO 53
<211> LENGTH: 16
<212> TYPE: PRT
<213> ORGANISM: Bovine sp.

<400> SEQUENCE: 53

Ile His Ile Asp Leu Pro Asn Glu Gln Ala Arg Leu Asp Ile Leu Lys
1               5                   10                  15

<210> SEQ ID NO 54
<211> LENGTH: 11
<212> TYPE: PRT
<213> ORGANISM: Bovine sp.

<400> SEQUENCE: 54

Ala Thr Asn Gly Pro Arg Tyr Val Val Val Gly
1               5                   10

<210> SEQ ID NO 55
<211> LENGTH: 7
<212> TYPE: PRT
<213> ORGANISM: Bovine sp.

<400> SEQUENCE: 55

Glu Ile Asp Gly Arg Leu Lys
1               5

<210> SEQ ID NO 56
<211> LENGTH: 14
<212> TYPE: PRT
<213> ORGANISM: Bovine sp.

<400> SEQUENCE: 56

Ala Leu Gln Ser Val Gly Gln Ile Val Gly Glu Val Leu Lys
1               5                   10

<210> SEQ ID NO 57
<211> LENGTH: 8
<212> TYPE: PRT
<213> ORGANISM: Bovine sp.

<400> SEQUENCE: 57

Ile Leu Ala Gly Pro Ile Thr Lys
1               5

<210> SEQ ID NO 58
<211> LENGTH: 16
<212> TYPE: PRT
<213> ORGANISM: Bovine sp.
<220> FEATURE:
```

```
<221> NAME/KEY: misc_feature
<222> LOCATION: (1)..(2)
<223> OTHER INFORMATION: Xaa can be any naturally occurring amino acid

<400> SEQUENCE: 58

Xaa Xaa Val Ile Glu Leu Pro Leu Thr Asn Pro Glu Leu Phe Gln Gly
  1               5                  10                  15

<210> SEQ ID NO 59
<211> LENGTH: 9
<212> TYPE: PRT
<213> ORGANISM: Bovine sp.

<400> SEQUENCE: 59

Val Val Ser Ser Ser Leu Val Asp Lys
  1               5

<210> SEQ ID NO 60
<211> LENGTH: 7
<212> TYPE: PRT
<213> ORGANISM: Bovine sp.

<400> SEQUENCE: 60

Ala Leu Gln Asp Tyr Arg Lys
  1               5

<210> SEQ ID NO 61
<211> LENGTH: 7
<212> TYPE: PRT
<213> ORGANISM: Bovine sp.

<400> SEQUENCE: 61

Glu His Arg Glu Gln Leu Lys
  1               5

<210> SEQ ID NO 62
<211> LENGTH: 12
<212> TYPE: PRT
<213> ORGANISM: Bovine sp.

<400> SEQUENCE: 62

Lys Leu Glu Ser Lys Leu Asp Tyr Lys Pro Val Arg
  1               5                  10

<210> SEQ ID NO 63
<211> LENGTH: 5
<212> TYPE: PRT
<213> ORGANISM: Bovine sp.

<400> SEQUENCE: 63

Leu Val Pro Thr Arg
  1               5

<210> SEQ ID NO 64
<211> LENGTH: 11
<212> TYPE: PRT
<213> ORGANISM: Bovine sp.

<400> SEQUENCE: 64

Ala Lys Glu Glu Glu Ile Glu Ala Gln Ile Lys
  1               5                  10

<210> SEQ ID NO 65
<211> LENGTH: 10
<212> TYPE: PRT
<213> ORGANISM: Bovine sp.
```

<400> SEQUENCE: 65

Ala Asn Tyr Glu Val Leu Glu Ser Gln Lys
1               5                   10

<210> SEQ ID NO 66
<211> LENGTH: 11
<212> TYPE: PRT
<213> ORGANISM: Bovine sp.

<400> SEQUENCE: 66

Val Glu Asp Ala Leu His Gln Leu His Ala Arg
1               5                   10

<210> SEQ ID NO 67
<211> LENGTH: 8
<212> TYPE: PRT
<213> ORGANISM: Bovine sp.

<400> SEQUENCE: 67

Asp Val Asp Leu Tyr Gln Val Arg
1               5

<210> SEQ ID NO 68
<211> LENGTH: 13
<212> TYPE: PRT
<213> ORGANISM: Bovine sp.

<400> SEQUENCE: 68

Gln Ser Gln Gly Leu Ser Pro Ala Gln Ala Phe Ala Lys
1               5                   10

<210> SEQ ID NO 69
<211> LENGTH: 21
<212> TYPE: PRT
<213> ORGANISM: Bovine sp.

<400> SEQUENCE: 69

Ala Gly Ser Gln Ser Gly Gly Ser Pro Glu Ala Ser Gly Val Thr Val
1               5                   10                  15

Ser Asp Val Gln Glu
            20

<210> SEQ ID NO 70
<211> LENGTH: 12
<212> TYPE: PRT
<213> ORGANISM: Bovine sp.
<220> FEATURE:
<221> NAME/KEY: misc_feature
<222> LOCATION: (5)..(5)
<223> OTHER INFORMATION: Xaa can be any naturally occurring amino acid

<400> SEQUENCE: 70

Gly Leu Leu Gly Xaa Asn Ile Ile Pro Leu Gln Arg
1               5                   10

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Primer P1

<400> SEQUENCE: 71
ttgaagaatg atgcattagg aaccac                                        26

<210> SEQ ID NO 72
<211> LENGTH: 34
<212> TYPE: DNA
<213> ORGANISM: Artificial Sequence
<220> FEATURE:
<223> OTHER INFORMATION: Description of Artificial Sequence: Primer P2

<400> SEQUENCE: 72
cactcgagtg gctggatttc aatttctcca gtag                          34

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Primer P3

<400> SEQUENCE: 73
gtcgagctag ccatctcctc ttcg                                    24

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Primer P4

<400> SEQUENCE: 74
catgggcgac aggttccgag acc                                     23

<210> SEQ ID NO 75
<211> LENGTH: 9
<212> TYPE: PRT
<213> ORGANISM: Homo sapiens

<400> SEQUENCE: 75

Lys Gly Ile Pro Ser Phe Trp Leu Thr
  1               5

<210> SEQ ID NO 76
<211> LENGTH: 9
<212> TYPE: PRT
<213> ORGANISM: Saccharomyces sp.

<400> SEQUENCE: 76

Lys Gly Ile Pro Glu Phe Trp Leu Thr
  1               5

<210> SEQ ID NO 77
<211> LENGTH: 10
<212> TYPE: PRT
<213> ORGANISM: Homo sapiens

<400> SEQUENCE: 77

Asp Ser Phe Phe Asn Phe Ala Pro Pro
  1               5                   10

<210> SEQ ID NO 78
<211> LENGTH: 9
<212> TYPE: PRT
<213> ORGANISM: Saccharomyces sp.

<400> SEQUENCE: 78

Glu Ser Phe Phe Asn Phe Ser Pro
  1               5

```
<210> SEQ ID NO 79
<211> LENGTH: 14
<212> TYPE: PRT
<213> ORGANISM: Artificial Sequence
<220> FEATURE:
<221> NAME/KEY: misc_feature
<222> LOCATION: (2)..(11)
<223> OTHER INFORMATION: Xaa can be any naturally occurring amino acid

<400> SEQUENCE: 79

Glu Xaa Xaa Lys Glu Xaa Pro Glu Val Lys Xaa Glu Glu Lys
 1               5                  10

<210> SEQ ID NO 80
<211> LENGTH: 5
<212> TYPE: PRT
<213> ORGANISM: HIV-1

<400> SEQUENCE: 80

Gly Arg Lys Lys Arg
 1               5

<210> SEQ ID NO 81
<211> LENGTH: 5
<212> TYPE: PRT
<213> ORGANISM: Homo sapiens

<400> SEQUENCE: 81

Lys Lys Lys Arg Lys
 1               5

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: A1 Primer

<400> SEQUENCE: 82
cctaaaaagt gtctaagtgc cagtt                                              25

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: A2 Primer

<400> SEQUENCE: 83
tcagtgaaag ggaaggtaga acac                                               24

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: P1 Primer

<400> SEQUENCE: 84
taatgaattt cattttagga ggtcgg                                             26

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: P2 Primer
```

<400> SEQUENCE: 85
atcttttggg aaagtaagat gagcc                                        25

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: C1 Primer

<400> SEQUENCE: 86
ggagactcac ctgctaatgt t                                            21

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: C4 Primer

<400> SEQUENCE: 87
ctcaaaagca gtctcttggc                                              20

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Primer A

<400> SEQUENCE: 88
atgggagata cagtagtgga gc                                           22

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Primer B

<400> SEQUENCE: 89
tcacatgatg ccgttggtga g                                            21

<210> SEQ ID NO 90
<211> LENGTH: 51
<212> TYPE: DNA
<213> ORGANISM: Homo sapiens

<400> SEQUENCE: 90
tggatcaagc caatacaaga ttcttgtgaa attacgactg atagtggcat g           51

<210> SEQ ID NO 91
<211> LENGTH: 117
<212> TYPE: DNA
<213> ORGANISM: Homo sapiens

<400> SEQUENCE: 91
tccatttggg aacaggagcg agtgcccctt tggatcaagc catacaagat tcttgtgatt  60
tcggctgata gtggcatgat tgaaccagtg gtcaatgctg tgtccatcca tcaggtg    117

<210> SEQ ID NO 92
<211> LENGTH: 31
<212> TYPE: DNA
<213> ORGANISM: Artificial Sequence

```
<220> FEATURE:
<223> OTHER INFORMATION: Description of Artificial Sequence: Primer C1

<400> SEQUENCE: 92
ctcagatcta tgggagatac agtagtggag c                                    31

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Primer C2

<400> SEQUENCE: 93
tcgagatctt cacatgatgc cgttggtgag                                      30

<210> SEQ ID NO 94
<211> LENGTH: 28
<212> TYPE: DNA
<213> ORGANISM: Artificial Sequence
<220> FEATURE:
<223> OTHER INFORMATION: Description of Artificial Sequence: P1 Primer

<400> SEQUENCE: 94
gatttgtgct caataatcac tatctgaa                                        28

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: P2 Primer

<400> SEQUENCE: 95
ggttactagg atcacaaagt atgaattctg gaa                                  33

<210> SEQ ID NO 96
<211> LENGTH: 5
<212> TYPE: PRT
<213> ORGANISM: HIV-1

<400> SEQUENCE: 96

Tyr Arg Lys Lys Arg
 1               5
```

HUMAN SKELETAL MUSCLE-SPECIFIC UBIQUITIN-CONJUGATING ENZYME

CROSS-REFERENCE TO RELATED APPLICATIONS

This Application is a Divisional of U.S. application Ser. No. 11/593,525 filed Nov. 7, 2006 (now U.S. Pat. No. 7,674,889), which is a Divisional of U.S. application Ser. No. 10/781,841 filed Feb. 20, 2004 (now abandoned), which is a Divisional of U.S. application Ser. No. 10/342,276 filed Jan. 15, 2003 (now U.S. Pat. No. 7,420,048), which is a Divisional of U.S. application Ser. No. 09/976,165 filed Oct. 15, 2001 (now U.S. Pat. No. 6,562,947), which is a Divisional of U.S. application Ser. No. 09/565,538 filed May 5, 2000 (now U.S. Pat. No. 6,333,404), which is a Divisional of U.S. application Ser. No. 09/273,565 filed Mar. 22, 1999 (now U.S. Pat. No. 6,166,190), which is a Divisional of U.S. application Ser. No. 09/055,699 filed Apr. 7, 1998 (now U.S. Pat. No. 6,005,088), which in turn is a Divisional of U.S. application Ser. No. 08/820,170, filed Mar. 19, 1997 (now U.S. Pat. No. 5,831,058), the disclosure of each of which is incorporated herein by reference.

TECHNICAL FIELD

The present invention relates to a gene useful as an indicator in the prophylaxis, diagnosis and treatment of diseases in humans. More particularly, it relates to a novel human gene analogous to rat, mouse, yeast, nematode and known human genes, among others, and utilizable, after cDNA analysis thereof, chromosome mapping of cDNA and function analysis of cDNA, in gene diagnosis using said gene and in developing a novel therapeutic method.

BACKGROUND ART

The genetic information of a living thing has been accumulated as sequences (DNA) of four bases, namely A, C, G and T, which exist in cell nuclei. Said genetic information has been preserved for line preservation and ontogeny of each individual living thing.

In the case of human being, the number of said bases is said to be about 3 billion ($3 \times 10^9$) and supposedly there are 50 to 100 thousand genes therein. Such genetic information serves to maintain biological phenomena in that regulatory proteins, structural proteins and enzymes are produced via such route that mRNA is transcribed from a gene (DNA) and then translated into a protein. Abnormalities in said route from gene to protein translation are considered to be causative of abnormalities of life supporting systems, for example in cell proliferation and differentiation, hence causative of various diseases.

As a result of gene analyses so far made, a number of genes which may be expected to serve as useful materials in drug development, have been found, for example genes for various receptors such as insulin receptor and LDL receptor, genes involved in cell proliferation and differentiation and genes for metabolic enzymes such as proteases, ATPase and superoxide dismutases.

However, analysis of human genes and studies of the functions of the genes analyzed and of the relations between the genes analyzed and various diseases have been just begun and many points remain unknown. Further analysis of novel genes, analysis of the functions thereof, studies of the relations between the genes analyzed and diseases, and studies for applying the genes analyzed to gene diagnosis or for medicinal purposes, for instance, are therefore desired in the relevant art.

If such a novel human gene as mentioned above can be provided, it will be possible to analyze the level of expression thereof in each cell and the structure and function thereof and, through expression product analysis and other studies, it may become possible to reveal the pathogenesis of a disease associated therewith, for example a genopathy or cancer, or diagnose and treat said disease, for instance. It is an object of the present invention to provide such a novel human gene.

For attaining the above object, the present inventors made intensive investigations and obtained the findings mentioned below. Based thereon, the present invention has now been completed.

DISCLOSURE OF THE INVENTION

Thus, the present inventors synthesized cDNAs based on mRNAs extracted from various tissues, inclusive of human fetal brain, adult blood vessels and placenta, constructed libraries by inserting them into vectors, allowing colonies of *Escherichia coli* transformed with said libraries to form on agar medium, picked up colonies at random and transferred to 96-well micro plates and registered a large number of human gene-containing *E. coli* clones.

Each clone thus registered was cultivated on a small size, DNA was extracted and purified, the four base-specifically terminating extension reactions were carried out by the dideoxy chain terminator method using the cDNA extracted as a template, and the base sequence of the gene was determined over about 400 bases from the 5' terminus thereof using an automatic DNA sequencer. Based on the thus-obtained base sequence information, a novel family gene analogous to known genes of animal and plant species such as bacteria, yeasts, nematodes, mice and humans was searched for.

The method of the above-mentioned cDNA analysis is detailedly described in the literature by Fujiwara, one of the present inventors (Fujiwara, Tsutomu, Saibo Kogaku (*Cell Engineering*), 14:645-654 (1995)).

Among this group, there are novel receptors, DNA binding domain-containing transcription regulating factors, signal transmission system factors, metabolic enzymes and so forth. Based on the homology of the novel gene of the present invention as obtained by gene analysis to the genes analogous thereto, the product of the gene, hence the function of the protein, can approximately be estimated by analogy. Furthermore, such functions as enzyme activity and binding ability can be investigated by inserting the candidate gene into an expression vector to give a recombinant.

According to the present invention, there are provided a novel human gene characterized by containing a nucleotide sequence coding for an amino acid sequence defined by SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37 or SEQ ID NO:40, a human gene characterized by containing the nucleotide sequence defined by SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38 or SEQ ID NO:41, respectively coding for the amino acid sequence mentioned above, and a novel human gene characterized by the nucleotide sequence defined by SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39 or SEQ ID NO:42.

The symbols used herein for indicating amino acids, peptides, nucleotides, nucleotide sequences and so on are those recommended by IUPAC and IUB or in "Guideline for drafting specifications etc., including nucleotide sequences or amino acid sequences" (edited by the Japanese Patent Office), or those in conventional use in the relevant field of art.

As specific examples of such gene of the present invention, there may be mentioned genes deducible from the DNA sequences of the clones designated as "GEN-501D08", "GEN-080G01", "GEN-025F07", "GEN-076C09", "GEN-331G07", "GEN-163D09", "GEN-078D05TA13", "GEN-423A12", "GEN-092E10", "GEN-428B12", "GEN-073E07", "GEN-093E05" and "GEN-077A09" shown later herein in Examples 1 to 11. The respective nucleotide sequences are as shown in the sequence listing.

These clones have an open reading frame comprising nucleotides (nucleic acid) respectively coding for the amino acids shown in the sequence listing. Their molecular weights were calculated at the values shown later herein in the respective examples. Hereinafter, these human genes of the present invention are sometimes referred to as the designation used in Examples 1 to 11.

In the following, the human gene of the present invention is described in further detail.

As mentioned above, each human gene of the present invention is analogous to rat, mouse, yeast, nematode and known human genes, among others, and can be utilized in human gene analysis based on the information about the genes analogous thereto and in studying the function of the gene analyzed and the relation between the gene analyzed and a disease. It is possible to use said gene in gene diagnosis of the disease associated therewith and in exploitation studies of said gene for medicinal purposes.

The gene of the present invention is represented in terms of a single-stranded DNA sequence, as shown under SEQ ID NO:2. It is to be noted, however, that the present invention also includes a DNA sequence complementary to such a single-stranded DNA sequence and a component comprising both. The sequence of the gene of the present invention as shown under SEQ ID NO:3n−1 (where n is an integer of 1 to 14) is merely an example of the codon combination encoding the respective amino acid residues. The gene of the present invention is not limited thereto but can of course have a DNA sequence in which the codons are arbitrarily selected and combined for the respective amino acid residues. The codon selection can be made in the conventional manner, for example taking into consideration the codon utilization frequencies in the host to be used (*Nucl. Acids Res.*, 9:43-74 (1981)).

The gene of the present invention further includes DNA sequences coding for functional equivalents derived from the amino acid sequence mentioned above by partial amino acid or amino acid sequence substitution, deletion or addition. These polypeptides may be produced by spontaneous modification (mutation) or may be obtained by posttranslational modification or by modifying the natural gene (of the present invention) by a technique of genetic engineering, for example by site-specific mutagenesis (*Methods in Enzymology*, 154: 350, 367-382 (1987); ibid., 100:468 (1983); *Nucleic Acids Research*, 12:9441 (1984); Zoku Seikagaku Jikken Koza (Sequel to Experiments in Biochemistry) 1, "Idensi Kenkyu-ho (Methods in Gene Research) II", edited by the Japan Biochemical Society, p. 105 (1986) or synthesizing mutant DNAs by a chemical synthetic technique such as the phostriester method or phosphoamidite method (*J. Am. Chem. Soc.*, 89:4801 (1967); ibid., 91:3350 (1969); *Science*, 150: 178 (1968); *Tetrahedron Lett.*, 22:1859 (1981); ibid., 24:245 (1983)), or by utilizing the techniques mentioned above in combination.

The protein encoded by the gene of the present invention can be expressed readily and stably by utilizing said gene, for example inserting it into a vector for use with a microorganism and cultivating the microorganism thus transformed.

The protein obtained by utilizing the gene of the present invention can be used in specific antibody production. In this case, the protein producible in large quantities by the genetic engineering technique mentioned above can be used as the component to serve as an antigen. The antibody obtained may be polyclonal or monoclonal and can be advantageously used in the purification, assay, discrimination or identification of the corresponding protein.

The gene of the present invention can be readily produced based on the sequence information thereof disclosed herein by using general genetic engineering techniques (cf., e.g., Molecular Cloning, 2nd Ed., Cold Spring Harbor Laboratory Press (1989); Zoku Seikagaku Jikken Koza, "Idenshi Kenkyu-ho I, II and III", edited by the Japan Biochemical Society (1986)).

This can be achieved, for example, by selecting a desired clone from a human cDNA library (prepared in the conventional manner from appropriate cells of origin in which the gene is expressed) using a probe or antibody specific to the gene of the present invention (e.g., *Proc. Natl. Acad. Sci. USA*, 78:6613 (1981); *Science*, 222:778 (1983)).

The cells of origin to be used in the above method are, for example, cells or tissues in which the gene in question is expressed, or cultured cells derived therefrom. Separation of total RNA, separation and purification of mRNA, conversion to (synthesis of) cDNA, cloning thereof and so on can be carried out by conventional methods. cDNA libraries are also commercially available and such cDNA libraries, for example various cDNA libraries available from Clontech Lab. Inc. can also be used in the above method.

Screening of the gene of the present invention from these cDNA libraries can be carried out by the conventional method mentioned above. These screening methods include, for example, the method comprising selecting a cDNA clone by immunological screening using an antibody specific to the protein produced by the corresponding cDNA, the technique of plaque or colony hybridization using probes selectively binding to the desired DNA sequence, or a combination of these. As regards the probe to be used here, a DNA sequence chemically synthesized based on the information about the DNA sequence of the present invention is generally used. It is of course possible to use the gene of the present invention or fragments thereof as the proble.

Furthermore, a sense primer and an antisense primer designed based on the information about the partial amino acid sequence of a natural extract isolated and purified from cells or a tissue can be used as probes for screening.

For obtaining the gene of the present invention, the technique of DNA/RNA amplification by the PCR method (*Science*, 230:1350-1354 (1984)) can suitably be employed. Particularly when the full-length cDNA can hardly be obtained from the library, the RACE method (rapid amplification of cDNA ends; Jikken Igaku (*Experimental Medicine*), 12(6): 35-38 (1994)], in particular the 5'RACE method (Frohman, M. A., et al., *Proc. Natl. Acad. Sci. USA*, 85:8998-9002 (1988)) is preferably employed. The primers to be used in such PCR method can be appropriately designed based on the sequence information of the gene of the present invention as disclosed herein and can be synthesized by a conventional method.

The amplified DNA/RNA fragment can be isolated and purified by a conventional method as mentioned above, for example by gel electrophoresis.

The nucleotide sequence of the thus-obtained gene of the present invention or any of various DNA fragments can be determined by a conventional method, for example the dideoxy method (*Proc. Natl. Acad. Sci. USA*, 74:5463-5467 (1977)) or the Maxam-Gilbert method (*Methods in Enzymology*, 65:499 (1980)). Such nucleotide sequence determination can be readily performed using a commercially available sequence kit as well.

When the gene of the present invention is used and conventional techniques of recombinant DNA technology (see, e.g., *Science*, 224:1431 (1984); *Biochem. Biophys. Res. Comm.*, 130:692 (1985); *Proc. Natl. Acad. Sci. USA*, 80:5990 (1983) and the references cited above) are followed, a recombinant protein can be obtained. More detailedly, said protein can be produced by constructing a recombinant DNA enabling the gene of the present invention to be expressed in host cells, introducing it into host cells for transformation thereof and cultivating the resulting transformant.

In that case, the host cells may be eukaryotic or prokaryotic. The eukaryotic cells include vertebrate cells, yeast cells and so on, and the vertebrate cells include, but are not limited to, simian cells named COS cells (*Cell*, 23:175-182 (1981)), Chinese hamster ovary cells and a dihydrofolate reductase-deficient cell line derived therefrom (*Proc. Natl. Acad. Sci. USA*, 77:4216-4220 (1980)) and the like, which are frequently used.

As regards the expression vector to be used with vertebrate cells, an expression vector having a promoter located upstream of the gene to be expressed, RNA splicing sites, a polyadenylation site and a transcription termination sequence can be generally used. This may further have an origin of replication as necessary. As an example of said expression vector, there may be mentioned pSV2dhfr (*Mol. Cell. Biol.*, 1:854 (1981)), which has the SV40 early promoter. As for the eukaryotic microorganisms, yeasts are generally and frequently used and, among them, yeasts of the genus *Saccharomyces* can be used with advantage. As regards the expression vector for use with yeasts and other eukaryotic microorganisms, pAM82 (*Proc. Natl. Acad. Sci. USA*, 80:1-5 (1983)), which has the acid phosphatase gene promoter, for instance, can be used.

Furthermore, a prokaryotic gene fused vector can be preferably used as the expression vector for the gene of the present invention. As specific examples of said vector, there may be mentioned pGEX-2TK and pGEX-4T-2 which have a GST domain (derived from *S. japonicum*) with a molecular weight of 26,000.

*Escherichia coli* and *Bacillus subtilis* are generally and preferably used as prokaryotic hosts. When these are used as hosts in the practice of the present invention, an expression plasmid derived from a plasmid vector capable of replicating in said host organisms and provided in this vector with a promoter and the SD (Shine and Dalgarno) sequence upstream of said gene for enabling the expression of the gene of the present invention and further provided with an initiation codon (e.g., ATG) necessary for the initiation of protein synthesis is preferably used. The *Escherichia coli* strain K12, among others, is preferably used as the host *Escherichia coli*, and pBR322 and modified vectors derived therefrom are generally and preferably used as the vector, while various known strains and vectors can also be used. Examples of the promoter which can be used are the tryptophan (trp) promoter, lpp promoter, lac promoter and PL/PR promoter.

The thus-obtained desired recombinant DNA can be introduced into host cells for transformation by using various general methods. The transformant obtained can be cultured by a conventional method and the culture leads to expression and production of the desired protein encoded by the gene of the present invention. The medium to be used in said culture can suitably be selected from among various media in conventional use according to the host cells employed. The host cells can be cultured under conditions suited for the growth thereof.

In the above manner, the desired recombinant protein is expressed and produced and accumulated or secreted within the transformant cells or extracellularly or on the cell membrane.

The recombinant protein can be separated and purified as desired by various separation procedures utilizing the physical, chemical and other properties thereof (cf., e.g., "Seikagaku (Biochemistry) Data Book II", pages 1175-1259, 1st Edition, 1st Printing, published Jun. 23, 1980, by Tokyo Kagaku Dojin; *Biochemistry*, 25(25):8274-8277 (1986); *Eur. J. Biochem.*, 163:313-321 (1987)). Specifically, said procedures include, among others, ordinary reconstitution treatment, treatment with a protein precipitating agent (salting out), centrifugation, osmotic shock treatment, sonication, ultrafiltration, various liquid chromatography techniques such as molecular sieve chromatography (gel filtration), adsorption chromatography, ion exchange chromatography, affinity chromatography and high-performance liquid chromatography (HPLC), dialysis and combinations thereof. Among them, affinity chromatography utilizing a column with the desired protein bound thereto is particularly preferred.

Furthermore, on the basis of the sequence information about the gene of the present invention as revealed by the present invention, for example by utilizing part or the whole of said gene, it is possible to detect the expression of the gene of the present invention in various human tissues. This can be performed by a conventional method, for example by RNA amplification by RT-PCR (reverse transcribed-polymerase chain reaction) (Kawasaki, E. S., et al., Amplification of RNA, in PCR Protocol, A guide to methods and applications, Academic Press, Inc., San Diego, 21-27 (1991)), or by northern blotting analysis (Molecular Cloning, Cold Spring Harbor Laboratory (1989)), with good results.

The primers to be used in employing the above-mentioned PCR method are not limited to any particular ones provided that they are specific to the gene of the present invention and enable the gene of the present invention alone to be specifically amplified. They can be designed or selected appropriately based on the gene information provided by the present invention. They can have a partial sequence comprising about 20 to 30 nucleotides according to the established practice. Suitable examples are as shown in Examples 1 to 11.

Thus, the present invention also provides primers and/or probes useful in specifically detecting such novel gene.

By using the novel gene provided by the present invention, it is possible to detect the expression of said gene in various tissues, analyze the structure and function thereof and, further, produce the human protein encoded by said gene in the manner of genetic engineering. These make it possible to analyze the expression product, reveal the pathology of a disease associated therewith, for example a genopathy or cancer, and diagnose and treat the disease.

The following drawings are referred to in the examples.

EXAMPLES

Figure 1:
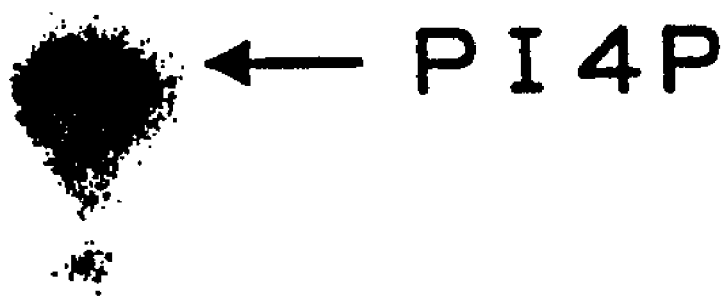
FIG. 1 shows the result obtained by testing the PI4 kinase activity of NPIK in Example 9.
Figure 1:

The following examples illustrate the present invention in further detail.

Example 1

GDP Dissociation Stimulator Gene (1) Cloning and DNA Sequencing of GDP Dissociation Stimulator Gene mRNAs extracted from the tissues of human fetal brain, adult blood vessels and placenta were purchased from Clontech and used as starting materials.

cDNA was synthesized from each mRNA and inserted into the vector λZAPII (Stratagene) to thereby construct a cDNA library (Otsuka GEN Research Institute, Otsuka Pharmaceutical Co., Ltd.).

Human gene-containing *Escherichia coli* colonies were allowed to form on agar medium by the in vivo excision technique (Short, J. M., et al., *Nucleic Acids Res.*, 16:7583-7600 (1988)). Colonies were picked up at random and human gene-containing *Escherichia coli* clones were registered on 96-well micro plates. The clones registered were stored at −80° C.

Each of the clones registered was cultured overnight in 1.5 ml of LB medium, and DNA was extracted and purified using a model PI-100 automatic plasmid extractor (Kurabo). Contaminant *Escherichia coli* RNA was decomposed and removed by RNase treatment. The DNA was dissolved to a final volume of 30 µl. A 2-µl portion was used for roughly checking the DNA size and quantity using a minigel, 7 µl was used for sequencing reactions and the remaining portion (21 µl) was stored as plasmid DNA at 4° C.

This method, after slight changes in the program, enables extraction of the cosmid, which is useful also as a probe for FISH (fluorescence in situ hybridization) shown later in the examples.

Then, the dideoxy terminator method of Sanger et al. (Sanger, F., et al., *Proc. Natl. Acad. Sci. USA*, 74:5463-5467 (1977)) using T3, T7 or a synthetic oligonucleotide primer or the cycle sequence method (Carothers, A. M., et al., *Bio. Techniques*, 7:494-499 (1989)) comprising the dideoxy chain terminator method plus PCR method was carried out. These are methods of terminating the extension reaction specifically to the four bases using a small amount of plasmid DNA (about 0.1 to 0.5 µg) as a template.

The sequence primers used were FITC (fluorescein isothiocyanate)-labeled ones. Generally, about 25 cycles of reaction were performed using Taq polymerase. The PCR products were separated on a polyacrylamide urea gel and the fluorescence-labeled DNA fragments were submitted to an automatic DNA sequencer (ALF™ DNA Sequencer; Pharmacia) for determining the sequence of about 400 bases from the 5' terminus side of cDNA.

Since the 3' nontranslational region is high in heterogeneity for each gene and therefore suited for discriminating individual genes from one another, sequencing was performed on the 3' side as well depending on the situation.

The vast sum of nucleotide sequence information obtained from the DNA sequencer was transferred to a 64-bit DEC 3400 computer for homology analysis by the computer. In the homology analysis, a data base (GenBank, EMBL) was used for searching according to the UWGCG FASTA program (Pearson, W. R. and Lipman, D. J., *Proc. Natl. Acad. Sci. USA*, 85:2444-2448 (1988)).

As a result of arbitrary selection by the above method and of cDNA sequence analysis, a clone designated as GEN-501D08 and having a 0.8 kilobase insert was found to show a high level of homology to the C terminal region of the human Ral guanine nucleotide dissociation stimulator (RalGDS) gene. Since RalGDS is considered to play a certain role in signal transmission pathways, the whole nucleotide sequence of the cDNA insert portion providing the human homolog was further determined.

Low-molecular GTPases play an important role in transmitting signals for a number of cell functions including cell proliferation, differentiation and transformation (Bourne, H. R. et al., *Nature*, 348:125-132 (1990); Bourne et al., *Nature*, 349:117-127 (1991)).

It is well known that, among them, those proteins encoded by the ras gene family function as molecular switches or, in other words, the functions of the ras gene family are regulated by different conditions of binding proteins such as biologically inactive GDP-binding proteins or active GDP-binding proteins, and that these two conditions are induced by GTPase activating proteins (GAPs) or GDS. The former enzymes induce GDP binding by stimulating the hydrolysis of bound GTP and the latter enzyme induces the regular GTP binding by releasing bound GDP (Bogusuki, M. S, and McCormick, F., *Nature*, 366:643-654 (1993)).

RalGDS was first discovered as a member of the ras gene family lacking in transforming activity and as a GDP dissociation stimulator specific to RAS (Chardin, P. and Tavitian, A., *EMBO J.*, 5:2203-2208 (1986); Albright, C. F., et al., *EMBO J.*, 12:339-347 (1993)).

In addition to Ral, RalGDS was found to function, through interaction with these proteins, as an effector molecule for N-ras, H-ras, K-ras and Rap (Spaargaren, M. and Bischoff, J. R., *Proc. Natl. Acad. Sci. USA*, 91:12609-12613 (1994)).

The nucleotide sequence of the cDNA clone designated as GEN-501D08 is shown under SEQ ID NO:3, the nucleotide sequence of the coding region of said clone under SEQ ID NO:2, and the amino acid sequence encoded by said nucleotide sequence under SEQ ID NO:1.

This cDNA comprises 842 nucleotides, including an open reading frame comprising 366 nucleotides and coding for 122 amino acids. The translation initiation codon was found to be located at the 28th nucleotide residue.

Comparison between the RalGDS protein known among conventional databases and the amino acid sequence deduced from said cDNA revealed that the protein encoded by this cDNA is homologous to the C terminal domain of human RalGDS. The amino acid sequence encoded by this novel gene was found to be 39.5% identical with the C terminal domain of RalGDS which is thought to be necessary for binding to ras.

Therefore, it is presumable, as mentioned above, that this gene product might interact with the ras family proteins or have influence on the ras-mediated signal transduction pathways. However, this novel gene is lacking in the region coding for the GDS activity domain and the corresponding protein seems to be different in function from the GDS protein. This gene was named human RalGDS by the present inventors.

(2) Northern Blot Analysis

The expression of the RalGDS protein mRNA in normal human tissues was evaluated by Northern blotting using, as a probe, the human cDNA clone labeled by the random oligonucleotide priming method.

The Northern blot analysis was carried out with a human MTN blot (Human Multiple Tissue Northern blot; Clontech, Palo Alto, Calif., USA) according to the manufacturer's protocol.

Thus, the PCR amplification product from the above GEN-501D08 clone was labeled with [$^{32}$P]-dCTP (random-primed DNA labeling kit, Boehringer-Mannheim) for use as a probe.

For blotting, hybridization was performed overnight at 42° C. in a solution comprising 50% formamide/5×SSC/50×Denhardt's solution/0.1% SDS (containing 100 µg/ml denatured salmon sperm DNA). After washing with two portions of 2×SSC/0.01% SDS at room temperature, the membrane filter was further washed three times with 0.1×SSC/0.05% SDS at 50° C. for 40 minutes. An X-ray film (Kodak) was exposed to the filter at −70° C. for 18 hours.

As a result, it was revealed that a 900-bp transcript had been expressed in all the human tissues tested. In addition, a 3.2-kb transcript was observed specifically in the heart and skeletal muscle. The expression of these transcripts differing in size may be due either to alternative splicing or to cross hybridization with homologous genes.

(3) Cosmid Clone and Chromosome Localization by Fish

FISH was performed by screening a library of human chromosomes cloned in the cosmid vector pWE15 using, as a probe, the 0.8-kb insert of the cDNA clone (Sambrook, J., et al., *Molecular Cloning*, 2nd Ed., pp. 3.1-3.58, Cold Spring Harbor Laboratory Press, Cold Spring Harbor, N.Y. (1989)).

FISH for chromosome assignment was carried out by the method of Inazawa et al. which comprises G-banding pattern comparison for confirmation (Inazawa, J., et al., *Genomics*, 17:153-162 (1993)).

For use as a probe, the cosmid DNA (0.5 µg) obtained from chromosome screening and corresponding to GEN-501D08 was labeled with biotin-16-dUTP by nick translation.

To eliminate the background noise due to repetitive sequences, 0.5 µl of sonicated human placenta DNA (10 mg/ml) was added to 9.5 µl of the probe solution. The mixture was denatured at 80° C. for 5 minutes and admixed with an equal volume of 4×SSC containing 20% dextransulfate. Then, a denatured slide was sown with the hybridization mixture and, after covering with paraffin, incubated in a wet chamber at 37° C. for 16 to 18 hours. After washing with 50% formamide/2×SSC at 37° C. for 15 minutes, the slide was washed with 2×SSC for 15 minutes and further with 1×SSC for 15 minutes.

The slide was then incubated in 4×SSC supplemented with "1% Block Ace" (trademark; Dainippon Pharmaceutical) containing avidin-FITC (5 µg/ml) at 37° C. for 40 minutes. Then, the slide was washed with 4×SSC for 10 minutes and with 4×SSC containing 0.05% Triton X-100® for 10 minutes and immersed in an antifading PPD solution (prepared by adjusting 100 mg of PPD (Wako Catalog No. 164-015321) and 10 ml of PBS(−) (pH 7.4) to pH 8.0 with 0.5 M Na$_2$CO$_3$/0.5 M NaHCO$_3$ (9:1, v/v) buffer (pH 9.0) and adding glycerol to make a total volume of 100 ml) containing 1% DABCO (1% DABCO (Sigma) in PBS(−):glycerol 1:9 (v:v)), followed by counter staining with DAPI (4,6-diamino-2-phenylindole; Sigma).

With more than 100 tested cells in the metaphase, a specific hybridization signal was observed on the chromosome band at 6p21.3, without any signal on other chromosomes. It was thus confirmed that the RalGDS gene is located on the chromosome 6p21.3.

By using the novel human RalGDS-associated gene of the present invention as obtained in this example, the expression of said gene in various tissues can be detected and the human RalGDS protein can be produced in the manner of genetic engineering. These are expected to enable studies on the roles of the expression product protein and ras-mediated signals in transduction pathways as well as pathological investigations of diseases in which these are involved, for example cancer, and the diagnosis and treatment of such diseases. Furthermore, it becomes possible to study the development and progress of diseases involving the same chromosomal translocation of the RalGDS protein gene of the present invention, for example tonic spondylitis, atrial septal defect, pigmentary retinopathy, aphasia and the like.

Example 2

Cytoskeleton-Associated Protein 2 Gene (CKAP2 Gene)

(1) Cytoskeleton-Associated Protein 2 Gene Cloning and DNA Sequencing cDNA clones were arbitrarily chosen from a human fetal brain cDNA library in the same manner as in Example 1 were subjected to sequence analysis and, as a result, a clone having a base sequence containing the CAP-glycine domain of the human cytoskeleton-associated protein (CAP) gene and highly homologous to several CAP family genes was found and named GEN-080G01.

Meanwhile, the cytoskeleton occurs in the cytoplasm and just inside the cell membrane of eukaryotic cells and is a network structure comprising complicatedly entangled filaments. Said cytoskeleton is constituted of microtubules composed of tubulin, microfilaments composed of actin, intermediate filaments composed of desmin and vimentin, and so on. The cytoskeleton not only acts as supportive cellular elements but also isokinetically functions to induce morphological changes of cells by polymerization and depolymerization in the fibrous system. The cytoskeleton binds to intracellular organelles, cell membrane receptors and ion channels and thus plays an important role in intracellular movement and locality maintenance thereof and, in addition, is said to have functions in activity regulation and mutual information transmission. Thus it supposedly occupies a very important position in physiological activity regulation of the whole cell. In particular, the relation between canceration of cells and qualitative changes of the cytoskeleton attracts attention since cancer cells differ in morphology and recognition response from normal cells.

The activity of this cytoskeleton is modulated by a number of cytoskeleton-associated proteins (CAPs). One group of CAPs is characterized by a glycine motif highly conserved and supposedly contributing to association with microtubules (CAP-GLY domain; Riehemann, K. and Song, C., *Trends Biochem. Sci.*, 18:82-83 (1993)).

Among the members of this group of CAPs, there are CLIP-170, 150 kDa DAP (dynein-associated protein, or dynactin), *D. melanogaster* GLUED, *S. cerevisiae* BIK1, restin (Bilbe, G., et al., *EMBO J.*, 11:2103-2113 (1992)); Hilliker, C., et al., *Cytogenet. Cell Genet.*, 65:172-176 (1994)) and *C. elegans* 13.5 kDa protein (Wilson, R., et al., *Nature*, 368:32-38 (1994)). Except for the last two proteins, direct or indirect evidences have suggested that they could interact with microtubules.

The above-mentioned CLIP-170 is essential for the in vitro binding of endocytic vesicles to microtubules and colocalizes with endocytic organelles (Rickard, J. E. and Kreis, T. E., *J. Biol. Chem.*, 18:82-83 (1990); Pierre, P., et al., *Cell,* 70:887 900 (1992)).

The above-mentioned dynactin is one of the factors constituting the cytoplasmic dynein motor, which functions in retrograde vesicle transport (Schroer, T. A. and Sheetz, M. P., *J. Cell Biol.*, 115:1309-1318 (1991)) or probably in the movement of chromosomes during mitosis (Pfarr, C. M., et al., *Nature,* 345:263-265 (1990); Steuer, E. R., et al., *Nature,* 345:266-268 (1990); Wordeman, L., et al., *J. Cell Biol.*, 114: 285-294 (1991)).

GLUED, the *Drosophila* homolog of mammalian dynactin, is essential for the viability of almost all cells and for the proper organization of some neurons (Swaroop, A., et al., *Proc. Natl. Acad. Sci. USA,* 84:6501-6505 (1987); Holzbaur, E. L. P., et al., *Nature,* 351:579-583 (1991)).

BIK1 interacts with microtubules and plays an important role in spindle formation during mitosis in yeasts (Trueheart, J., et al., *Mol. Cell. Biol.*, 7:2316-2326 (1987); Berlin, V., et al., *J. Cell Biol.*, 111:2573-2586 (1990)).

At present, these genes are classified under the term CAP family (CAPs).

As a result of database searching, the above-mentioned cDNA clone of 463-bp (excluding the poly-A signal) showed significant homology in nucleotide sequence with the restin and CLIP-170 encoding genes. However, said clone was lacking in the 5' region as compared with the restin gene and, therefore, the technique of 5' RACE (Frohman, M. A., et al., *Proc. Natl. Acad. Sci. USA,* 85:8998-9002 (1988)) was used to isolate this missing segment.

(2) 5' RACE (5' Rapid Amplification of cDNA Ends)

A cDNA clone containing the 5' portion of the gene of the present invention was isolated for analysis by the 5' RACE technique using a commercial kit (5'-Rapid AmpliFinder RACE kit, Clontech) according to the manufacturer's protocol with minor modifications, as follows.

The gene-specific primer P1 and primer P2 used here were synthesized by the conventional method and their nucleotide sequences are as shown below in Table 1. The anchor primer used was the one attached to the commercial kit.

TABLE 1

| Primer | Nucleotide sequence |
|---|---|
| Primer P1 | 5'-ACACCAATCCAGTAGCCAGGCTTG-3' (SEQ ID NO: 43) |
| Primer P2 | 5'-CACTCGAGAATCTGTGAGACCTACATACATGACG-3' (SEQ ID NO: 44) | cDNA was obtained by reverse transcription of 0.1 µg of human fetal brain poly(A)+RNA by the random hexamer technique using reverse transcriptase (Superscript™ II, Life Technologies) and the cDNA was amplified by the first PCR using the P1 primer and anchor primer according to Watanabe et al. (Watanabe, T., et al., *Cell Genet.*, in press).

Thus, to 0.1 µg of the above-mentioned cDNA were added 2.5 mM dNTP/1× Taq buffer (Takara Shuzo)/0.2 µM P1 primer, 0.2 µM adaptor primer/0.25 unit ExTaq enzyme (Takara Shuzo) to make a total volume of 50 µl, followed by addition of the anchor primer. The mixture was subjected to PCR. Thus, 35 cycles of amplification were performed under the conditions: 94° C. for 45 seconds, 60° C. for 45 seconds, and 72° C. for 2 minutes. Finally, the mixture was heated at 72° C. for 5 minutes.

Then, 1 µl of the 50-µl first PCR product was subjected to amplification by the second PCR using the specific nested P2 primer and anchor primer. The second PCR product was analyzed by 1.5% agarose gel electrophoresis.

Upon agarose gel electrophoresis, a single band, about 650 nucleotides in size, was detected. The product from this band was inserted into a vector (pT7Blue®T-Vector, Novagen) and a plurality of clones with an insert having an appropriate size were selected.

Six of the 5' RACE clones obtained from the PCR product had the same sequence but had different lengths. By sequencing two overlapping cDNA clones, GEN-080G01 and GEN-080G0149, the protein-encoding sequence and 5' and 3' flanking sequences, 1015 nucleotides in total length, were determined. Said gene was named cytoskeleton-associated protein 2 gene (CKAP2 gene).

The nucleotide sequence obtained from the above-mentioned two overlapping cDNA clones GEN-080G01 and GEN-080G0149 is shown under SEQ ID NO:6, the nucleotide sequence of the coding region of said clone under SEQ ID NO:5, and the amino acid sequence encoded by said nucleotide sequence under SEQ ID NO:4.

As shown under SEQ ID NO:6, the CKAP2 gene had a relatively GC-rich 5' noncoding region, with incomplete triplet repeats, (CAG)4(CGG)4(CTG)(CGG), occurring at nucleotides 40-69.

ATG located at nucleotides 274-276 is the presumable start codon. A stop codon (TGA) was situated at nucleotides 853-855. A polyadenylation signal (ATTAAA) was followed by 16 nucleotides before the poly(A) start. The estimated open reading frame comprises 579 nucleotides coding for 193 amino acid residues with a calculated molecular weight of 21,800 daltons.

The coding region was further amplified by RT-PCR, to eliminate the possibility of the synthetic sequence obtained being a cDNA chimera.

(2) Similarity of CKAP2 to Other CAPs

While sequencing of CKAP2 revealed homology with the sequences of restin and CLIP-170, the homologous region was limited to a short sequence corresponding to the CAP-GLY domain. On the amino acid level, the deduced CKAP2 was highly homologous to five other CAPs in this domain.

CKAP2 was lacking in such other motif characteristics of some CAPs as the alpha helical rod and zinc finger motif. The alpha helical rod is thought to contribute to dimerization and to increase the microtubule binding capacity (Pierre, P., et al., *Cell,* 70:887-900 (1992)). The lack of the alpha helical domain might mean that CKAP2 be incapable of homo or hetero dimer formation.

Paralleling of the CAP-GLY domains of these proteins revealed that other conserved residues other than glycine residues are also found in CKAP2. CAPs having a CAP-GLY domain are thought to be associated with the activities of cellular organelles and the interactions thereof with microtubules. Since it contains a CAP-GLY domain, as mentioned above, CKAP2 is placed in the family of CAPs.

Studies with mutants of Glued have revealed that the Glued product plays an important role in almost all cells (Swaroop, A., et al., *Proc. Natl. Acad. Sci. USA,* 84:6501-6505 (1987)) and that it has other neuron-specific functions in neuronal cells (Meyerowitz, E. M. and Kankel, D. R., *Dev. Biol.*, 62:112-142 (1978)). These microtubule-associated proteins are thought to function in vesicle transport and mitosis. Because of the importance of the vesicle transport system in neuronal cells, defects in these components might lead to aberrant neuronal systems.

In view of the above, CKAP2 might be involved in specific neuronal functions as well as in fundamental cellular functions.

(3) Northern Blot Analysis

The expression of human CKAP2 mRNA in normal human tissues was examined by Northern blotting in the same manner as in Example 1 (2) using the GEN-080G01 clone (corresponding to nucleotides 553-1015) as a probe.

As a result, in all the eight tissues tested, namely human heart, brain, placenta, lung, liver, skeletal muscle, kidney and pancreas, a 1.0 kb transcript agreeing in size with the CKAP2 cDNA was detected. Said 1.0 kb transcript was expressed at significantly higher levels in heart and brain than in the other tissues examined. Two weak bands, 3.4 kb and 4.6 kb, were also detected in all the tissues examined.

According to the Northern blot analysis, the 3.4 kb and 4.6 kb transcripts might possibly be derived from the same gene coding for the 1.0 kb CKAP2 by alternative splicing or transcribed from other related genes. These characteristics of the transcripts may indicate that CKAP2 might also code for a protein having a CAP-GLY domain as well as an alpha helix.

(4) Cosmid Cloning and Chromosomal Localization by Direct R-Banding FISH

Two cosmids corresponding to the CKAP2 cDNA were obtained. These two cosmid clones were subjected to direct R-banding FISH in the same manner as in Example 1 (3) for chromosomal locus mapping of CKAP2.

For suppressing the background due to repetitive sequences, a 20-fold excessive amount of human Cot-I DNA (BRL) was added as described by Lichter et al. (Lichter, P., et al., *Proc. Natl. Acad. Sci. USA*, 87:6634-6638 (1990)). A Provia 100 film (Fuji ISO 100; Fuji Photo Film) was used for photomicrography.

As a result, CKAP2 was mapped on chromosome bands 19q13.11-q13.12.

Two autosomal dominant neurological diseases have been localized to this region by linkage analysis: CADASIL (cerebral autosomal dominant arteriopathy with subcortical infarcts and leukoencephalopathy) between the DNA markers D19S221 and D19S222, and FHM (familial hemiplegic migraine) between D19S215 and D19S216. These two diseases may be allelic disorders in which the same gene is involved (Tournier-Lasserve, E., et al., *Nature Genet.*, 3:256-259 (1993); Joutel, A., et al., *Nature Genet.*, 5:40-45 (1993)).

Although no evidence is available to support CKAP2 as a candidate gene for FHM or CADASIL, it is conceivable that its mutation might lead to some or other neurological disease.

By using the novel human CKAP2 gene of the present invention as obtained in this example, it is possible to detect the expression of said gene in various tissues or produce the human CKAP2 gene in the manner of genetic engineering. Through these, it becomes possible to analyze the functions of the human CKAP2 system or human CKAP2, which is involved in diverse activities essential to cells, as mentioned above, to diagnose various neurological diseases in which said system or gene is involved, for example familial migraine, and to screen out and evaluate a therapeutic or prophylactic drug therefor.

Example 3

OTK27 Gene (1) OTK27 Gene Cloning and DNA Sequencing

As a result of sequence analysis of cDNA clones arbitrarily selected from a human fetal brain cDNA library in the same manner as in Example 1 (1) and database searching, a cDNA clone, GEN-025F07, coding for a protein highly homologous to NHP2, a yeast nucleoprotein (*Saccharomyces cerevisiae*; Kolodrubetz, D. and Burgum, A., *YEAST*, 7:79-90 (1991)), was found and named OTK27.

Nucleoproteins are fundamental cellular constituents of chromosomes, ribosomes and so forth and are thought to play an essential role in cell multiplication and viability. The yeast nucleoprotein NHP2, a high-mobility group (HMG)-like protein, like HMG, has reportedly a function essential for cell viability (Kolodrubetz, D. and Burgum, A., *YEAST*, 7:79-90 (1991)).

The novel human gene, OTK27 gene, of the present invention, which is highly homologous to the above-mentioned yeast NHP2 gene, is supposed to be similar in function.

The nucleotide sequence of said GEN-025F07 clone was found to comprise 1493 nucleotides, as shown under SEQ ID NO:9, and contain an open reading frame comprising 384 nucleotides, as shown under SEQ ID NO:8, coding for an amino acid sequence comprising 128 amino acid residues, as shown under SEQ ID NO:7. The initiation codon was located at nucleotides 95-97 of the sequence shown under SEQ ID NO:9, and the termination codon at nucleotides 479-481.

At the amino acid level, the OTK27 protein was highly homologous (38%) to NHP2. It was 83% identical with the protein deduced from the cDNA from *Arabidopsis thaliana*; Newman, T., unpublished; GENEMBL Accession No. T14197).

(2) Northern Blot Analysis

For examining the expression of human OTK27 mRNA in normal human tissues, the insert in the OTK27 cDNA was amplified by PCR, the PCR product was purified and labeled with [$^{32}$P]-dCTP (random-primed DNA labeling kit, Boehringer Mannheim), and Northern blotting was performed using the labeled product as a probe in the same manner as in Example 1 (2).

As a result of the Northern blot analysis, two bands corresponding to possible transcripts from this gene were detected at approximately 1.6 kb and 0.7 kb. Both sizes of transcript were expressed in all normal adult tissues examined. However, the expression of the 0.7 kb transcript was significantly reduced in brain and was of higher levels in heart, skeletal muscle and testicle than in other tissues examined.

For further examination of these two transcripts, eleven cDNA clones were isolated from a testis cDNA library and their DNA sequences were determined in the same manner as in Example 1 (1).

As a result, in six clones, the sequences were found to be in agreement with that of the 0.7 kb transcript, with a poly(A) sequence starting at around the 600th nucleotide, namely at the 598th nucleotide in two of the six clones, at the 606th nucleotide in three clones, and at the 613th nucleotide in one clone.

In these six clones, the "TATAAA" sequence was recognized at nucleotides 583-588 as a probable poly(A) signal. The upstream poly(A) signal "TATAAA" of this gene was recognized as little influencing in brain and more effective in the three tissues mentioned above than in other tissues. The possibility was considered that the stability of each transcript vary from tissue to tissue.

Results of zoo blot analysis indicated that this gene is well conserved also in other vertebrates. Since this gene is expressed ubiquitously in normal adult tissues and conserved among a wide range of species, the gene product is likely to play an important physiological role. The evidence that yeasts lacking in NHP2 are nonviable suggests that the human homolog may also be essential to cell viability.

(3) Chromosomal Localization of OTK27 by Direct R-Banding FISH

One cosmid clone corresponding to the cDNA OTK27 was isolated from a total human genomic cosmid library (5-genome equivalent) using the OTK27 cDNA insert as a probe and subjected to FISH in the same manner as in Example 1 (3) for chromosomal localization of OTK27.

As a result, two distinct spots were observed on the chromosome band 12q24.3.

The OTK27 gene of the present invention can be used in causing expression thereof and detecting the OTK27 protein, a human nucleoprotein, and thus can be utilized in the diagnosis and pathologic studies of various diseases in which said protein is involved and, because of its involvement in cell proliferation and differentiation, in screening out and evaluating therapeutic and preventive drugs for cancer.

Example 4

OTK18 Gene (1) OTK18 Gene Cloning and DNA Sequencing

Zinc finger proteins are defined as constituting a large family of transcription-regulating proteins in eukaryotes and carry evolutionarily conserved structural motifs (Kadonaga, J. T., et al., *Cell,* 51:1079-1090 (1987); Klung, A. and Rhodes, D., *Trends Biol. Sci.,* 12:464-469 (1987); Evans, R. M. and Hollenberg, S. M., *Cell,* 52:1-3 (1988)).

The zinc finger, a loop-like motif formed by the interaction between the zinc ion and two residues, cysteine and histidine residues, is involved in the sequence-specific binding of a protein to RNA or DNA. The zinc finger motif was first identified within the amino acid sequence of the *Xenopus* transcription factor IIIA (Miller, J., et al., *EMBO J.,* 4:1609-1614 (1986)).

The $C_2H_2$ finger motif is in general tandemly repeated and contains an evolutionarily conserved intervening sequence of 7 or 8 amino acids. This intervening stretch was first identified in the Kruppel segmentation gene of *Drosophila* (Rosenberg, U. B., et al., *Nature,* 319:336-339 (1986)). Since then, hundreds of $C_2H_2$ zinc finger protein-encoding genes have been found in vertebrate genomes.

As a result of sequence analysis of cDNA clones arbitrarily selected from a human fetal brain cDNA library in the same manner as in Example 1 (1) and database searching, several zinc finger structure-containing clones were identified and, further, a clone having a zinc finger structure of the Kruppel type was found.

Since this clone lacked the 5' portion of the transcript, plaque hybridization was performed with a fetal brain cDNA library using, as a probe, an approximately 1.8 kb insert in the cDNA clone, whereby three clones were isolated. The nucleotide sequences of these were determined in the same manner as in Example 1 (1).

Among the three clones, the one having the largest insert spans 3,754 nucleotides including an open reading frame of 2,133 nucleotides coding for 711 amino acids. It was found that said clone contains a novel human gene coding for a peptide highly homologous in the zinc finger domain to those encoded by human ZNF41 and the *Drosophila* Kruppel gene. This gene was named OTK18 gene (derived from the clone GEN-076C09).

The nucleotide sequence of the cDNA clone of the OTK18 gene is shown under SEQ ID NO:12, the coding region-containing nucleotide sequence under SEQ ID NO:11, and the predicted amino acid sequence encoded by said OTK18 gene under SEQ ID NO:10.

It was found that the amino acid sequence of OTK18 as deduced from SEQ ID NO:12 contains 13 finger motifs on its carboxy side.

(2) Comparison with Other Zinc Finger Motif-Containing Genes

Comparison among OTK18, human ZNF41 and the *Drosophila* Kruppel gene revealed that each finger motif is for the most part conserved in the consensus sequence $CXECGKAFXQKSXLX_2HQRXH$ (SEQ ID NO:45).

Comparison of the consensus sequence of the zinc finger motifs of OTK18 with those of human ZNF41 and the *Drosophila* Kruppel gene revealed that the Kruppel type motif is well conserved in the OTK18-encoded protein. However, the sequence similarities were limited to zinc finger domains and no significant homologies were found with regard to other regions.

The zinc finger domain interacts specifically with the target DNA, recognizing an about 5 bp sequence to thereby bind to the DNA helix (Rhodes, D. and Klug, A., *Cell,* 46:123-132 (1986)).

Based on the idea that, in view of the above, the multiple module (tandem repetitions of zinc finger) can interact with long stretches of DNA, it is presumable that the target DNA of this gene product containing 13 repeated zinc finger units would be a DNA fragment with a length of approximately 65 bp.

(3) Northern Blot Analysis

Northern blot analysis was performed as described in Example 1 (2) for checking normal human tissues for expression of the human OTK18 mRNA therein by amplifying the insert of the OTK18 cDNA by PCR, purifying the PCR product, labeling the same with [$^{32}$P]-dCTP (random-primed DNA labeling kit, Boehringer Mannheim) and using an MTN blot with the labeled product as a probe.

The results of Northern blot analysis revealed that the transcript of OTK18 is approximately 4.3 kb long and is expressed ubiquitously in various normal adult tissues. However, the expression level in the liver and in peripheral blood lymphocytes seemed to be lower than in other organs tested.

(4) Cosmid Cloning and Chromosomal Localization by Direct R-Banding FISH

Chromosomal localization of OTK18 was carried out as described in Example 1 (3).

As a result, complete twin spots were identified with 8 samples while 23 samples showed an incomplete signal or twin spots on either or both homologs. All signals appeared at the q13.4 band of chromosome 19. No twin spots were observed on any other chromosomes.

The results of FISH thus revealed that this gene is localized on chromosomal band 19q13.4. This region is known to contain many DNA segments that hybridize with oligonucleotides corresponding to zinc finger domains (Hoovers, J. M. N., et al., *Genomics,* 12:254-263 (1992)). In addition, at least one other gene coding for a zinc finger domain has been identified in this region (Marine, J.-C., et al., *Genomics,* 21:285-286 (1994)).

Hence, the chromosome 19q13 is presumably a site of grouping of multiple genes coding for transcription-regulating proteins.

When the novel human OTK18 gene provided by this example is used, it becomes possible to detect expression of said gene in various tissues and produce the human OTK18 protein in the manner of genetic engineering. Through these, it is possible to analyze the functions of the human transcription regulating protein gene system or human transcription regulating proteins, which are deeply involved in diverse activities fundamental to cells, as mentioned above, to diagnose various diseases with which said gene is associated, for example malformation or cancer resulting from a developmental or differentiation anomaly, and mental or nervous disorder resulting from a developmental anomaly in the nervous system, and further to screen out and evaluate therapeutic or prophylactic drugs for these diseases.

Example 5

Genes Encoding Human 26S Proteasome Constituent P42 Protein and P27 Protein (1) Cloning and DNA Sequencing of Genes Respectively Encoding Human 26S Proteasome Constituent P42 Protein and P27 Protein Proteasome, which is a multifunctional protease, is an enzyme occurring widely in eukaryotes from yeasts to humans and decomposing ubiquitin-binding proteins in cells in an energy-dependent manner. Structurally, said proteasome is constituted of 20S proteasome composed of various constituents with a molecular weight of 21 to 31 kilodaltons and a group of PA700 regulatory proteins composed of various constituents with a molecular weight of 30 to 112 kilodaltons and showing a sedimentation coefficient of 22S and, as a whole, occurs as a macromolecule with a molecular weight of about 2 million daltons and a sedimentation coefficient of 26S (Rechsteiner, M., et al., *J. Biol. Chem.*, 268: 6065-6068 (1993); Yoshimura, T., et al., *J. Struct. Biol.*, 111: 200-211 (1993); Tanaka, K., et al., *New Biologist*, 4:173-187 (1992)).

Despite structural and mechanical analyses thereof, the whole picture of proteasome is not yet fully clear. However, according to studies using yeasts and mice in the main, it reportedly has the functions mentioned below and its functions are becoming more and more elucidated.

The mechanism of energy-dependent proteolysis in cells starts with selection of proteins by ubiquitin binding. It is not 20S proteasome but 26S proteasome that has ubiquitin-conjugated protein decomposing activity which is ATP-dependent (Chu-Ping et al., *J. Biol. Chem.*, 269:3539-3547 (1994)). Hence, human 26S proteasome is considered to be useful in elucidating the mechanism of energy-dependent proteolysis.

Factors involved in the cell cycle regulation are generally short in half-life and in many cases they are subject to strict quantitative control. In fact, it has been made clear that the oncogene products Mos, Myc, Fos and so forth can be decomposed by 26S proteasome in an energy- and ubiquitin-dependent manner (Ishida, N., et al., *FEBS Lett.*, 324:345-348 (1993); Hershko, A. and Ciechanover, A., *Annu. Rev. Biochem.*, 61:761-807 (1992)) and the importance of proteasome in cell cycle control is being recognized.

Its importance in the immune system has also been pointed out. It is suggested that proteasome is positively involved in class I major histocompatible complex antigen presentation (Michalek, M. T., et al., *Nature*, 363:552-554 (1993)) and it is further suggested that proteasome may be involved in Alzheimer disease, since the phenomena of abnormal accumulation of ubiquitin-conjugated proteins in the brain of patients with Alzheimer disease (Kitaguchi, N., et al., *Nature*, 361:530-532 (1988)). Because of its diverse functions such as those mentioned above, proteasome attracts attention from the viewpoint of its utility in the diagnosis and treatment of various diseases.

A main function of 26S proteasome is ubiquitin-conjugated protein decomposing activity. In particular, it is known that cell cycle-related gene products such as oncogene products and cyclins, typically c-Myc, are degraded via ubiquitin-dependent pathways. It has also been observed that the proteasome gene is expressed abnormally in liver cancer cells, renal cancer cells, leukemia cells and the like as compared with normal cells (Kanayama, H., et al., *Cancer Res.*, 51:6677-6685 (1991)) and that proteasome is abnormally accumulated in tumor cell nuclei. Hence, constituents of proteasome are expected to be useful in studying the mechanism of such canceration and in the diagnosis or treatment of cancer.

Also, it is known that the expression of proteasome is induced by interferon γ and so on and is deeply involved in antigen presentation in cells (Aki, M., et al., *J. Biochem.*, 115:257-269 (1994)). Hence, constituents of human proteasome are expected to be useful in studying the mechanism of antigen presentation in the immune system and in developing immunoregulating drugs.

Furthermore, proteasome is considered to be deeply associated with ubiquitin abnormally accumulated in the brain of patients with Alzheimer disease. Hence, it is suggested that constituents of human proteasome should be useful in studying the cause of Alzheimer disease and in the treatment of said disease.

In addition to the utilization of expectedly multifunctional proteasome as such in the above manner, it is probably possible to produce antibodies using constituents of proteasome as antigens and use such antibodies in diagnosing various diseases by immunoassay. Its utility in this field of diagnosis is thus also a focus of interest.

Meanwhile, a protein having the characteristics of human 26S proteasome is disclosed, for example in Japanese Unexamined Patent Publication No. 292964/1993 and rat proteasome constituents are disclosed in Japanese Unexamined Patent Publication Nos. 268957/1993 and 317059/1993. However, no human 26S proteasome constituents are known. Therefore, the present inventors made a further search for human 26S proteasome constituents and successfully obtained two novel human 26S proteasome constituents, namely human 26S proteasome constituent P42 protein and human S26 proteasome constituent P27 protein, and performed cloning and DNA sequencing of the corresponding genes in the following manner.

(1) Purification of Human 26S Proteasome Constituents P42 Protein and P27 Protein Human proteasome was purified using about 100 g of fresh human kidney and following the method of purifying human proteasome as described in Japanese Unexamined Patent Publication No. 292964/1993, namely by column chromatography using BioGel A-1.5 m (5×90 cm, Bio-Rad), hydroxyapatite (1.5×15 cm, Bio-Rad) and Q-Sepharose (1.5× 15 cm, Pharmacia) and glycerol density gradient centrifugation.

The thus-obtained human proteasome was subjected to reversed phase high performance liquid chromatography (HPLC) using a Hitachi model L6200 HPLC system. A Shodex RS Pak D4-613 (0.6×15 cm, Showa Denko) was used and gradient elution was performed with the following two solutions:

First solution: 0.06% trifluoroacetic acid; and
Second solution: 0.05% trifluoroacetic acid, 70% acetonitrile.

An aliquot of each eluate fraction was subjected to 8.5% SDS-polyacrylamide electrophoresis under conditions of reduction with dithiothreitol. The P42 protein and P27 protein thus detected were isolated and purified.

The purified P42 and P27 proteins were respectively digested with 1 μg of trypsin in 0.1 M Tris buffer (pH 7.8) containing 2 M urea at 37° C. for 8 hours and the partial peptide fragments obtained were separated by reversed phase HPLC and their sequences were determined by Edman degradation. The results obtained are as shown below in Table 2.

TABLE 2

| Partial protein | | Amino acid sequence |
|---|---|---|
| P42 | (1) | VLNISLW (SEQ ID NO: 46) |
| | (2) | TLMELLNQMDGFDTLHR (SEQ ID NO: 47) |
| | (3) | AVSDFVVSEYXMAXA (SEQ ID NO: 48) |
| | (4) | EVDPLVYNX (SEQ ID NO: 49) |
| | (5) | HGEIDYEAIVK (SEQ ID NO: 50) |
| | (6) | LSXGFNGADLRNVXTEAGMFAIXAD (SEQ ID NO: 51) |
| | (7) | MIMATNRPDTLDPALLRPGXL (SEQ ID NO: 52) |
| | (8) | IHIDLPNEQARLDILK (SEQ ID NO: 53) |
| | (9) | ATNGPRYVVVG (SEQ ID NO: 54) |
| | (10) | EIDGRLK (SEQ ID NO: 55) |
| | (11) | ALQSVGQIVGEVLK (SEQ ID NO: 56) |
| | (12) | ILAGPITK (SEQ ID NO: 57) |
| | (13) | XXVIELPLTNPELFQG (SEQ ID NO: 58) |
| | (14) | VVSSSLVDK (SEQ ID NO: 59) |
| | (15) | ALQDYRK (SEQ ID NO: 60) |
| | (16) | EHREQLK (SEQ ID NO: 61) |
| | (17) | KLESKLDYKPVR (SEQ ID NO: 62) |
| P27 | (1) | LVPTR (SEQ ID NO: 63) |
| | (2) | AKEEEIEAQIK (SEQ ID NO: 64) |
| | (3) | ANYEVLESQK (SEQ ID NO: 65) |
| | (4) | VEDALHQLHAR (SEQ ID NO: 66) |
| | (5) | DVDLYQVR (SEQ ID NO: 67) |
| | (6) | QSQGLSPAQAFAK (SEQ ID NO: 68) |
| | (7) | AGSQSGGSPEASGVTVSDVQE (SEQ ID NO: 69) |
| | (8) | GLLGXNIIPLQR (SEQ ID NO: 70) |

(2) cDNA Library Screening, Clone Isolation and cDNA Nucleotide Sequence Determination As mentioned in Example 1 (1), the present inventors have a database comprising about 30,000 cDNA data as constructed based on large-scale DNA sequencing using human fetal brain, arterial blood vessel and placenta cDNA libraries.

Based on the amino acid sequences obtained as mentioned above in (1), computer searching was performed with the FASTA program (search for homology between said amino acid sequences and the amino acid sequences estimated from the database). As regards P42, a clone (GEN-331G07) showing identity with regard to two amino acid sequences ((2) and (7) shown in Table 2) was screened out and, as regards P27, a clone (GEN-163D09) showing identity with regard to two amino acid sequences ((1) and (8) shown in Table 2) was found.

For each of these clones, the 5' side sequence was determined by 5' RACE and the whole sequence was determined, in the same manner as in Example 2 (2).

As a result, it was revealed that the above-mentioned P42 clone GEN-331G07 comprises a 1,566-nucleotide sequence as shown under SEQ ID NO:15, inclusive of a 1,167-nucleotide open reading frame as shown under SEQ ID NO:14, and that the amino acid sequence encoded thereby is the one shown under SEQ ID NO:13 and comprises 389 amino acid residues.

The results of computer homology search revealed that the P42 protein is significantly homologous to the AAA (ATPase associated with a variety of cellular activities) protein family (e.g., P45, TBP1, TBP7, S4, MSS1, etc.). It was thus suggested that it is a new member of the AAA protein family.

As for the P27 clone GEN-163D09, it was revealed that it comprises a 1,128-nucleotide sequence as shown under SEQ ID NO:18, including a 669-nucleotide open reading frame as shown under SEQ ID NO:17 and that the amino acid sequence encoded thereby is the one shown under SEQ ID NO:16 and comprises 223 amino acid residues.

As regards the P27 protein, homology search using a computer failed to reveal any homologous gene among public databases. Thus, the gene in question is presumably a novel gene having an unknown function.

Originally, the above-mentioned P42 and P27 gene products were both purified as regulatory subunit components of proteasome complex. Therefore, these are expected to play an important role in various biological functions through proteolysis, for example a role in energy supply through decomposition of ATP and, hence, they are presumably useful not only in studying the function of human 26S proteasome but also in the diagnosis and treatment of various diseases caused by lowering of said biological functions, among others.

Example 6

BNAP Gene (1) BNAP Gene Cloning and DNA Sequencing

The nucleosome composed of DNA and histone is a fundamental structure constituting chromosomes in eukaryotic cells and is well conserved over borders among species. This structure is closely associated with the processes of replication and transcription of DNA. However, the nucleosome formation is not fully understood as yet. Only certain specific factors involved in nucleosome assembly (NAPs) have been identified. Thus, two acidic proteins, nucleoplasmin and N1, are already known to facilitate nucleosome construction (Kleinschmidt, J. A., et al., *J. Biol. Chem.*, 260:1166-1176 (1985); Dilworth, S. M., et al., *Cell*, 51:1009-1018 (1987)).

A yeast gene, NAP-I, was isolated using a monoclonal antibody and recombinant proteins derived therefrom were tested as to whether they have nucleosome assembling activity in vivo.

More recently, a mouse NAP-I gene, which is a mammalian homolog of the yeast NAP-I gene was cloned (Okuda, A.; registered in database under the accession number D12618). Also cloned were a mouse gene, DN38 (Kato, K., *Eur. J. Neurosci.*, 2:704-711 (1990)) and a human nucleosome assembly protein (hNRP) (Simon, H. U., et al., *Biochem. J.*, 297:389-397 (1994)). It was shown that the hNRP gene is expressed in many tissues and is associated with T lymphocyte proliferation.

The present inventors performed sequence analysis of cDNA clones arbitrarily chosen from a human fetal brain cDNA library in the same manner as in Example 1 (1), followed by searches among databases and, as a result, made it clear that a 1,125-nucleotide cDNA clone (free of poly(A)), GEN-078D05, is significantly homologous to the mouse NAP-I gene, which is a gene for a nucleosome assembly protein (NAP) involved in nucleosome construction, a mouse partial cDNA clone, DN38, and hNRP.

Since said clone GEN-078D05 was lacking in the 5' region, 5' RACE was performed in the same manner as in Example 2 (2) to obtain the whole coding region. For this 5' RACE, primers P1 and P2 respectively having the nucleotide sequences shown below in Table 3.

TABLE 3

| Primer | Nucleotide sequence |
| --- | --- |
| Primer P1 | 5'-TTGAAGAATGATGCATTAGGAACCAC-3' (SEQ ID NO: 71) |
| Primer P2 | 5'-CACTCGAGTGGCTGGATTTCAATTTCTCCAGTAG-3' (SEQ ID NO: 72) |

After the first 5' RACE, a single band corresponding to a sequence length of 1,300 nucleotides was obtained. This product was inserted into pT7Blue® T-Vector and several clones appropriate in insert size were selected.

Ten 5' RACE clones obtained from two independent PCR reactions were sequenced and the longest clone GEN-078D05TA13 (about 1,300 nucleotides long) was further analyzed.

Both strands of the two overlapping cDNA clones GEN-078D05 and GEN-078D05TA13 were sequenced, whereby it was confirmed that the two clones did not yet cover the whole coding region. Therefore, a further second 5' RACE was carried out. For the second 5' RACE, two primers, P3 and P4, respectively having the sequences shown below in Table 4 were used.

TABLE 4

| Primer | Nucleotide sequence |
| --- | --- |
| Primer P3 | 5'-GTCGAGCTAGCCATCTCCTCTTCG-3' (SEQ ID NO: 73) |

TABLE 4-continued

| Primer | Nucleotide sequence |
| --- | --- |
| Primer P4 | 5'-CATGGGCGACAGGTTCCGAGACC-3' (SEQ ID NO: 74) |

A clone, GEN-078D0508, obtained by the second 5' RACE was 300 nucleotides long. This clone contained an estimable initiation codon and three preceding in-frame termination codons. From these three overlapping clones, it became clear that the whole coding region comprises 2,636 nucleotides. This gene was named brain-specific nucleosome assembly protein (BNAP) gene.

The BNAP gene contains a 1,518-nucleotide open reading frame shown under SEQ ID NO:20. The amino acid encoded thereby comprises 506 amino acid residues, as shown under SEQ ID NO:19, and the nucleotide sequence of the whole cDNA clone of BNAP is as shown under SEQ ID NO:21.

As shown under SEQ ID NO:21, the 5' noncoding region of said gene was found to be generally rich in GC. Candidate initiation codon sequences were found at nucleotides Nos. 266-268, 287-289 and 329-331. These three sequences all had well conserved sequences in the vicinity of the initiation codons (Kozak, M., *J. Biol. Chem.*, 266:19867-19870 (1991)).

According to the scanning model, the first ATG (nucleotides Nos. 266-268) of the cDNA clone may be the initiation codon. The termination codon was located at nucleotides Nos. 1784-1786.

The 3' noncoding redion was generally rich in AT and two polyadenylation signals (AATAAA) were located at nucleotides Nos. 2606-2611 and 2610-2615, respectively.

The longest open reading frame comprised 1,518 nucleotides coding for 506 amino acid residues and the calculated molecular weight of the BNAP gene product was 57,600 daltons.

Hydrophilic plots indicated that BNAP is very hydrophilic, like other NAPs.

For recombinant BNAP expression and purification and for eliminating the possibility that the BNAP gene sequence might give three chimera clones in the step of 5' RACE, RT-PCR was performed using a sequence comprising nucleotides Nos. 326-356 as a sense primer and a sequence comprising nucleotides Nos. 1758-1786 as an antisenses primer.

As a result, a single product of about 1,500 bp was obtained and it was thus confirmed that said sequence is not a chimera but a single transcript.

(2) Comparison Between BNAP and NAPs

The amino acid sequence deduced from BNAP showed 46% identity and 65% similarity to hNRP.

The deduced BNAP gene product had motifs characteristic of the NAPs already reported and of BNAP. In general, half of the C terminus was well conserved in humans and yeasts.

The first motif (domain I) is KGIPDYWLI (corresponding to amino acid residues Nos. 309-317 (of SEQ ID NO:19)). This was observed also in hNRP (KGIPSFWLT (SEQ ID NO:75)) and in yeast NAP-I (KGIPEFWLT (SEQ ID NO:76)).

The second motif (domain II) is ASFFNFFSPP (corresponding to amino acid residues Nos. 437-446 (of SEQ ID NO:19)) and this was expressed as DSFFNFFAPP (SEQ ID NO:77) in hNRP and as ESFFNFFSP (SEQ ID NO:78) in yeast NAP-I.

These two motifs were also conserved in the deduced mouse NAP-I and DN38 peptides. Both conserved motifs were each a hydrophilic cluster, and the Cys in position 402 was also found conserved.

Half of the N terminus had no motifs strictly conserved from yeasts to mammalian species, while motifs conserved among mammalian species were found.

For instance, HDLERKYA (corresponding to amino acid residues Nos. 130 to 137 (of SEQ ID NO:19)) and IINAEYEPTEEECEW (corresponding to amino acid residues Nos. 150-164 (of SEQ ID NO:19)), which may be associated with mammal-specific functions, were found strictly conserved.

NAPs had acidic stretches, which are believed to be readily capable of binding to histone or other basic proteins. All NAPs had three acidic stretches but the locations thereof were not conserved.

BNAP has not such three acidic stretches but, instead, three repeated sequences (corresponding to amino acid residues Nos. 194-207, 208-221 and 222-235) with a long acidic cluster, inclusive of 41 amino acid residues out of 98 amino acid residues, the consensus sequence being ExxKExPEVKxEEK (SEQ ID NO:79) (each x being a nonconserved, mostly hydrophobic, residue).

Furthermore, it was revealed that the BNAP sequence had several BNAP-specific motifs. Thus, an extremely serine-rich doamin (corresponding to amino acid residues Nos. 24-72) with 33 (67%) of 49 amino acid residues being serine residues was found in the N-terminus portion. On the nucleic acid level, they were reflected as incomplete repetitions of AGC.

Following this serine-rich region, there appeared a basic domain (corresponding to amino acid residues Nos. 71-89) comprising 10 basic amino acid residues among 19 residues.

BNAP is supposed to be localized in the nucleus. Two possible signals localized in the nucleus were observed (NLSs). The first signal was found in the basic domain of BNAP and its sequence YRKKR (SEQ ID NO:96) (corresponding to amino acid residues Nos. 75-79) was similar to NLS (GRKKR (SEQ ID NO:80)) of Tat of HIV-1. The second signal was located in the C terminus and its sequence KKYRK (corresponding to amino acid residues Nos. 502-506 (of SEQ ID NO:19)) was similar to NLS (KKKRK (SEQ ID NO:81)) of the large T antigen of SV40. The presence of these two presumable NLSs suggested the localization of BNAP in the nucleus. However, the possibility that other basic clusters might act as NLSs could not be excluded.

BNAP has several phosphorylation sites and the activity of BNAP may be controlled through phosphorylation thereof.

(3) Northern Blot Analysis

Northern blot analysis was performed as described in Example 1 (2). Thus, the clone GEN-078D05TA13 (corresponding to nucleotides Nos. 323 to 1558 in the BNAP gene sequence) was amplified by PCR, the PCR product was purified and labeled with [$^{32}$P]-dCTP (random-primed DNA labeling kit, Boehringer Mannheim), and the expression of BNAP mRNA in normal human tissues was examined using an MTN blot with the labeled product as a probe.

As a result of Northern blot analysis, a 3.0 kb transcript of BNAP was detected (8-hour exposure) in the brain among eight human adult tissues tested, namely heart, brain, placenta, lung, liver, skeletal muscle, kidney and pancreas and, after longer exposure (24 hours), a dim band of the same size was detected in the heart.

BNAP was found equally expressed in several sites of brain tested whereas, in other tissues, no signal was detected at all even after 72 hours of exposure. hNRP mRNA was found expressed everywhere in the human tissues tested whereas the expression of BNAP mRNA was tissue-specific.

(4) Radiation Hybrid Mapping

Chromosomal mapping of the BNAP clone was performed by means of radiation hybrid mapping (Cox, D. R., et al., *Science,* 250:245-250 (1990)).

Thus, a total human genome radiation hybrid clone (G3RH) panel was purchased from Research Genetics, Inc., AL, USA and PCR was carried out for chromosomal mapping analysis according to the product manual using two primers, A1 and A2, respectively having the nucleotide sequences shown in Table 5.

TABLE 5

| Primer | Nucleotide sequence |
| --- | --- |
| A1 primer | 5'-CCTAAAAAGTGTCTAAGTGCCAGTT-3' (SEQ ID NO: 82) |
| A2 primer | 5'-TCAGTGAAAGGGAAGGTAGAACAC-3' (SEQ ID NO: 83) |

The results obtained were analyzed utilizing softwares usable on the Internet (Boehnke, M., et al., *Am. J. Hum. Genet.,* 46:581-586 (1991)).

As a result, the BNAP gene was found strongly linked to the marker DXS990 (LOD=1000, cR8000=−0.00). Since DXS990 is a marker localized on the chromosome Xq21.3-q22, it was established that BNAP is localized to the chromosomal locus Xq21.3-q22 where genes involved in several signs or symptoms of X-chromosome-associated mental retardation are localized.

The nucleosome is not only a fundamental chromosomal structural unit characteristic of eukaryotes but also a gene expression regulating unit. Several results indicate that genes with high transcription activity are sensitive to nuclease treatment, suggesting that the chromosome structure changes with the transcription activity (Elgin, S. C. R., *J. Biol. Chem.,* 263:19259-19262 (1988)).

NAP-I has been cloned in yeast, mouse and human and is one of the factors capable of promoting nucleosome construction in vivo. In a study performed on their sequences, NAPs containing the epitope of the specific antibody 4A8 were detected in human, mouse, frog, *Drosophila* and yeast (*Saccharomyces cerevisiae*) (Ishimi, Y., et al., *Eur. J. Biochem.,* 162:19-24 (1987)).

In these experiments, NAPs, upon SDS-PAGE analysis, electrophoretically migrated to positions corresponding to a molecular weight between 50 and 60 kDa, whereas the recombinant BNAP slowly migrated to a position of about 80 kDa. The epitope of 4A8 was shown to be localized in the second, well-conserved, hydrophobic motif. And, it was simultaneously shown that the triplet FNF is important as a part of the epitope (Fujii-Nakata, T., et al., *J. Biol. Chem.,* 267:20980-20986 (1992)).

BNAP also contained this consensus motif in domain II. The fact that domain II is markedly hydrophobic and the fact that domain II can be recognized by the immune system suggest that it is probably presented on the BNAP surface and is possibly involved in protein-protein interactions.

Domain I, too, may be involved in protein-protein interactions. Considering that these are conserved generally among NAPs, though to a relatively low extent, it is conceivable that they must be essential for nucleosome construction, although the functional meaning of the conserved domains is still unknown.

The hNRP gene is expressed in thyroid gland, stomach, kidney, intestine, leukemia, lung cancer, mammary cancer and so on (Simon, H. U., et al., *Biochem. J.,* 297:389-397

(1994)). Like that, NAPs are expressed everywhere and are thought to be playing an important role in fundamental nucleosome formation.

BNAP may be involved in brain-specific nucleosome formation and an insufficiency thereof may cause neurological diseases or mental retardation as a result of deviated functions of neurons.

BNAP was found strongly linked to a marker on the X-chromosome q21.3-q22 where sequences involved in several symptoms of X-chromosome-associated mental retardation are localized. This center-surrounding region of X-chromosome was rich in genes responsible for α-thalassemia, mental retardation (ATR-X) or some other forms of mental retardation (Gibbons, R. J., et al., Cell, 80:837-845 (1995)). Like the analysis of the ATR-X gene which seems to regulate the nucleosome structure, the present inventors suppose that BNAP may be involved in a certain type of X-chromosome-linked mental retardation.

According to this example, the novel BNAP gene is provided and, when said gene is used, it is possible to detect the expression of said gene in various tissues and to produce the BNAP protein by the technology of genetic engineering. Through these, it is possible to study the brain nucleosome formation deeply involved, as mentioned above, in variegated activities essential to cells as well as the functions of cranial nerve cells and to diagnose various neurological diseases or mental retardation in which these are involved and screen out and evaluate drugs for the treatment or prevention of such diseases.

Example 7

Human Skeletal Muscle-Specific Ubiquitin-Conjugating Enzyme Gene (UBE2G Gene)

The ubiquitin system is a group of enzymes essential for cellular processes and is conserved from yeast to human. Said system is composed of ubiquitin-activating enzymes (UBAs), ubiquitin-conjugating enzymes (UBCs), ubiquitin protein ligases (UBRs) and 26S proteasome particles.

Ubiquitin is transferred from the above-mentioned UBAs to several UBCs, whereby it is activated. UBCs transfer ubiquitins to target proteins with or without the participation of UBRs. These ubiquitin-conjugated target proteins are said to induce a number of cellular responses, such as protein degradation, protein modification, protein translocation, DNA repair, cell cycle control, transcription control, stress responses, etc. and immunological responses (Jentsch, S., et al., Biochim. Biophys. Acta, 1089:127-139 (1991); Hershko, A. and Ciechanover, A., Annu. Rev. Biochem., 61:761-807 (1992); Jentsch, S., Annu. Rev. Genet., 26:179-207 (1992); Ciechanover, A., Cell, 79:13-21 (1994)).

UBCs are key components of this system and seem to have distinct substrate specificities and modulate different functions. For example, Saccharomyces cerevisiae UBC7 is induced by cadmium and involved in resistance to cadmium poisoning (Jungmann, J., et al., Nature, 361:369-371 (1993)). Degradation of MAT-α2 is also executed by UBC7 and UBC6 (Chen, P., et al., Cell, 74:357-369 (1993)).

The novel gene obtained in this example is UBC7-like gene strongly expressed in human skeletal muscle. In the following, cloning and DNA sequencing thereof are described.

(1) Cloning and DNA Sequencing of Human Skeletal Muscle-Specific Ubiquitin-Conjugating Enzyme Gene (UBE2G Gene)

Following the same procedure as in Example 1 (1), cDNA clones were arbitrarily selected from a human fetal brain cDNA library and subjected to sequence analysis, and database searches were performed. As a result, a cDNA clone, GEN-423A12, was found to have a significantly high level of homology to the genes coding for ubiquitin-conjugating enzymes (UBCs) in various species.

Since said GEN-423A12 clone was lacking in the 5' side, 5' RACE was performed in the same manner as in Example 2 (2) to obtain an entire coding region.

For said 5' RACE, two primers, P1 and P2, respectively having the nucleotide sequences shown in Table 6 were used.

TABLE 6

| Primer | Nucleotide sequence |
|---|---|
| P1 primer | 5'-TAATGAATTTCATTTTAGGAGGTCGG-3' (SEQ ID NO: 84) |
| P2 primer | 5'-ATCTTTTGGGAAAGTAAGATGAGCC-3' (SEQ ID NO: 85) |

The 5' RACE product was inserted into pT7Blue® T-Vector and clones with an insert proper in size were selected.

Four of the 5' RACE clones obtained from two independent PCR reactions contained the same sequence but were different in length.

By sequencing the above clones, the coding sequence and adjacent 5'- and 3'-flanking sequences of the novel gene were determined.

As a result, it was revealed that the novel gene has a total length of 617 nucleotides. This gene was named human skeletal muscle-specific ubiquitin-conjugating enzyme gene (UBE2G gene).

To exclude the conceivable possibility that this sequence was a chimera clone, RT-PCR was performed in the same manner as in Example 6 (1) using the sense primer to amplify said sequence from the human fetal brain cDNA library. As a result, a single PCR product was obtained, whereby it was confirmed that said sequence is not a chimera one.

The UBE2G gene contains an open reading frame of 510 nucleotides, which is shown under SEQ ID NO:23, the amino acid sequence encoded thereby comprises 170 amino acid residues, as shown under SEQ ID NO:22, and the nucleotide sequence of the entire UBE2G cDNA is as shown under SEQ ID NO:24.

As shown under SEQ ID NO:24, the estimable initiation codon was located at nucleotides Nos. 19-21, corresponding to the first ATG triplet of the cDNA clone. Since no preceding in-frame termination codon was found, it was deduced that this clone contains the entire open reading frame on the following grounds.

Thus, (a) the amino acid sequence is highly homologous to S. cerevisiae UBC7 and said initiation codon agrees with that of yeast UBC7, supporting said ATG as such. (b) The sequence AGGATGA (nucleotide Nos. 18-24 in the sequence shown under SEQ ID NO:24) is similar to the consensus sequence (A/G)CCATGG around the initiation codon (Kozak, M., J. Biol. Chem., 266:19867-19870 (1991)).

(2) Comparison in Amino Acid Sequence Between UBE2G and UBCs

Comparison in amino acid sequence between UBE2G and UBCs suggested that the active site cystein capable of binding to ubiquitin should be the 90th residue cystein. The peptides encoded by these genes seem to belong to the same family.

(3) Northern Blot Analysis

Northern blot analysis was carried out as described in Example 1 (2). Thus, the entire sequence of UBE2G was amplified by PCR, the PCR product was purified and labeled with [$^{32}$P]-dCTP (random-primed DNA labeling kit, Boehringer Mannheim) and the expression of UBE2G mRNA in normal human tissues using the labeled product as a probe. The membrane used was an MTN blot.

As a result of the Northern blot analysis, 4.4 kb, 2.4 kb and 1.6 kb transcripts could be detected in all 16 human adult tissues, namely heart, brain, placenta, lung, liver, skeletal muscle, kidney, pancreas, spleen, thyroid gland, urinary bladder, testis, ovary, small intestine, large intestine and peripheral blood leukocyte, after 18 hours of exposure. Strong expression of these transcripts was observed in skeletal muscle.

(4) Radiation Hybrid Mapping

Chromosomal mapping of the UBE2G clone was performed by radiation hybrid mapping in the same manner as in Example 6 (4).

The primers C1 and C4 used in PCR for chromosomal mapping analysis respectively correspond to nucleotides Nos. 415-435 and nucleotides Nos. 509-528 in the sequence shown under SEQ ID NO:24 and their nucleotide sequences are as shown below in Table 7.

TABLE 7

| Primer | Nucleotide sequence |
| --- | --- |
| C1 primer | 5'-GGAGACTCACCTGCTAATGTT-3' (SEQ ID NO: 86) |
| C4 primer | 5'-CTCAAAAGCAGTCTCTTGGC-3' (SEQ ID NO: 87) |

As a result, the UBE2G gene was found linked to the markers D1S446 (LOD=12.52, cR8000=8.60) and D1S235 (LOD=9.14, cR8000=22.46). These markers are localized to the chromosome bands 1q42.13-q42.3.

UBE2G was expressed strongly in skeletal muscle and very weakly in all other tissues examined. All other UBCs are involved in essential cellular functions, such as cell cycle control, and those UBCs are expressed ubiquitously. However, the expression pattern of UBE2G might suggest a muscle-specific role thereof.

While the three transcripts differing in size were detected, attempts failed to identify which corresponds to the cDNA clone. The primary structure of the UBE2G product showed an extreme homology to yeast UBC7. On the other hand, nematode UBC7 showed strong homology to yeast UBC7. It is involved in degradation of the repressor and further confers resistance to cadmium in yeasts. The similarities among these proteins suggest that they belong to the same family.

It is speculated that UBE2G is involved in degradation of muscle-specific proteins and that a defect in said gene could lead to such diseases as muscular dystrophy. Recently, another proteolytic enzyme, calpain 3, was found to be responsible for limb-girdle muscular dystrophy type 2A (Richard, I., et al., Cell, 81:27-40 (1995)). At the present, the chromosomal location of UBE2G suggests no significant relationship with any hereditary muscular disease but it is likely that a relation to the gene will be unearthed by linkage analysis in future.

In accordance with this example, the novel UBE2G gene is provided and the use of said gene enables detection of its expression in various tissues and production of the UBE2G protein by the technology of genetic engineering. Through these, it becomes possible to study the degradation of muscle-specific proteins deeply involved in basic activities variegated and essential to cells, as mentioned above, and the functions of skeletal muscle, to diagnose various muscular diseases in which these are involved and further to screen out and evaluate drugs for the treatment and prevention of such diseases.

Example 8

TMP-2 Gene (1) TMP-2 Gene Cloning and DNA Sequencing

Following the procedure of Example 1 (1), cDNA clones were arbitrarily selected from a human fetal brain cDNA library and subjected to sequence analysis, and database searches were performed. As a result, a clone (GEN-092E10) having a cDNA sequence highly homologous to a transmembrane protein gene (accession No.: U19878) was found out.

Membrane protein genes have so far been cloned in frog (*Xenopus laevis*) and human. These are considered to be a gene for a transmembrane type protein having a follistatin module and an epidermal growth factor (EGF) domain (accession No.: U19878).

The sequence information of the above protein gene indicated that the GEN-092E10 clone was lacking in the 5' region, so that the λgt10 cDNA library (human fetal brain 5'-STRETCH PLUS cDNA; Clontech) was screened using the GEN-092E10 clone as a probe, whereby a cDNA clone containing a further 5' upstream region was isolated.

Both strands of this cDNA clone were sequenced, whereby the sequence covering the entire coding region became clear. This gene was named TMP-2 gene.

The TMP-2 gene was found to contain an open reading frame of 1,122 nucleotides, as shown under SEQ ID NO:26, encoding an amino acid sequence of 374 residues, as shown under SEQ ID NO:25. The nucleotide sequence of the entire TMP-2 cDNA clone comprises 1,721 nucleotides, as shown under SEQ ID NO:27.

As shown under SEQ ID NO:27, the 5' noncoding region was generally rich in GC. Several candidates for the initiation codon were found but, according to the scanning model, the 5th ATG of the cDNA clone (bases Nos. 368-370) was estimated as the initiation codon. The termination codon was located at nucleotides Nos. 1490-1492. The polyadenylation signal (AATAAA) was located at nucleotides Nos. 1703-1708. The calculated molecular weight of the TMP-2 gene product was 41,400 daltons.

As mentioned above, the transmembrane genes have a follistatin module and an EGF domain. These motifs were also found conserved in the novel human gene of the present invention.

The TMP-2 gene of the present invention presumably plays an important role in cell proliferation or intercellular communication, since, on the amino acid level, said gene shows homology, across the EGF domain, to TGF-α (transforming growth factor-α; Derynck, R., et al., *Cell*, 38:287-297 (1984)), beta-cellulin (Igarashi, K. and Folkman, J., *Science*, 259:1604-1607 (1993)), heparin-binding EGF-like growth factor (Higashiyama, S., et al., *Science*, 251:936-939 (1991)) and schwannoma-derived growth factor (Kimura, H., et al., *Nature*, 348:257-260 (1990)).

(2) Northern Blot Analysis

Northern blot analysis was carried out as described in Example 1 (2). Thus, the clone GEN-092E10 was amplified by PCR, the PCR product was purified and labeled with [$^{32}$P]-dCTP (random-primed DNA labeling kit, Boehringer Mannheim), and the expression of TMP-2 mRNA in normal human tissues was examined using an MTN blot with the labeled product as a probe.

As a result, high levels of expression were detected in brain and prostate gland. Said TMP-2 gene mRNA was about 2 kb in size.

According to the present invention, the novel human TMP-2 gene is provided and the use of said gene makes it possible to detect the expression of said gene in various tissues or produce the human TMP-2 protein by the technology of genetic engineering and, through these, it becomes possible to study brain tumor and prostatic cancer, which are closely associated with cell proliferation or intercellular communication, as mentioned above, to diagnose these diseases and to screen out and evaluate drugs for the treatment and prevention of such diseases.

Example 9

Human NKIK Gene (1) Human NPIK Gene Cloning and DNA Sequencing

Following the procedures of Example 1 and Example 2, cDNA clones were arbitrarily selected from a human fetal brain cDNA library and subjected to sequence analysis, and database searches were performed. As a result, two cDNA clones highly homologous to the gene coding for an amino acid sequence conserved in phosphatidylinositol 3 and 4 kinases (Kunz, J., et al., Cell, 73:585-596 (1993)) were obtained. These were named GEN-428B12c1 and GEN-428B12c2 and the entire sequences of these were determined as in the foregoing examples.

As a result, the GEN-428B12c1 cDNA clone and the GEN-428B12c2 clone were found to have coding sequences differing by 12 amino acid residues at the 5' terminus, the GEN-428B12c1 cDNA clone being longer by 12 amino acid residues.

The GEN-428B12c1 cDNA sequence of the human NPIK gene contained an open reading frame of 2,487 nucleotides, as shown under SEQ ID NO:32, encoding an amino acid sequence comprising 829 amino acid residues, as shown under SEQ ID NO:31. The nucleotide sequence of the full-length cDNA clone comprised 3,324 nucleotides as shown under SEQ ID NO:33.

The estimated initiation codon was located, as shown under SEQ ID NO:33, at nucleotides Nos. 115-117 corresponding to the second ATG triplet of the cDNA clone. The termination codon was located at nucleotides Nos. 2602-2604 and the polyadenylation signal (AATAAA) at Nos. 3305-3310.

On the other hand, the GEN-428B12c2 cDNA sequence of the human NPIK gene contained an open reading frame of 2,451 nucleotides, as shown under SEQ ID NO:29. The amino acid sequence encoded thereby comprised 817 amino acid residues, as shown under SEQ ID NO:28. The nucleotide sequence of the full-length cDNA clone comprised 3,602 nucleotides, as shown under SEQ ID NO:30.

The estimated initiation codon was located, as shown under SEQ ID NO:30, at nucleotides Nos. 429-431 corresponding to the 7th ATG triplet of the cDNA clone. The termination codon was located at nucleotides Nos. 2880-2882 and the polyadenylation signal (AATAAA) at Nos. 3583-3588.

(2) Northern Blot Analysis

Northern blot analysis was carried out as described in Example 1 (2). Thus, the entire sequence of human NPIK was amplified by PCR, the PCR product was purified and labeled with [$^{32}$P]-dCTP (random-primed DNA labeling kit, Boehringer Mannheim), and normal human tissues were examined for expression of the human NPIK mRNA using the MTN blot membrane with the labeled product as a probe.

As a result, the expression of the human NPIK gene was observed in 16 various human adult tissues examined and an about 3.8 kb transcript and an about 5 kb one could be detected.

Using primer A having the nucleotide sequence shown below in Table 8 and containing the initiation codon of the GEN-428B12c2 cDNA and primer B shown in Table 8 and containing the termination codon, PCR was performed with Human Fetal Brain Marathon-Ready cDNA (Clontech) as a template, and the nucleotide sequence of the PCR product was determined.

TABLE 8

| Primer | Nucleotide sequence |
|---|---|
| Primer A | 5'-ATGGGAGATACAGTAGTGGAGC-3' (SEQ ID NO: 88) |
| Primer B | 5'-TCACATGATGCCGTTGGTGAG-3' (SEQ ID NO: 89) |

As a result, it was found that the human NPIK mRNA expressed included one lacking in nucleotides Nos. 1060-1104 of the GEN-428B12c1 cDNA sequence (SEQ ID NO:33) (amino acids Nos. 316-330 of the amino acid sequence under SEQ ID NO:31) and one lacking in nucleotides Nos. 1897-1911 of the GEN-428B12c1 cDNA sequence (SEQ ID NO:33) (amino acids Nos. 595-599 of the amino acid sequence under SEQ ID NO:31).

It was further revealed that polymorphism existed in this gene (428B12c1.fasta), as shown below in Table 9, in the region of bases Nos. 1941-1966 of the GEN-428B12c1 cDNA sequence shown under SEQ ID NO:33, whereby a mutant protein was encoded which resulted from the mutation of IQDSCEITT (amino acid residues Nos. 610-618 in the amino acid sequence (SEQ ID NO:31) encoded by GEN-428B12c1) into YKILVISA.

TABLE 9

```
                                           1930         1940         1950    1959
                                      TGGATCAAGCCAATACAAGATTCTTGTGAA
                                      |||||||||||| ||||||||||||||||
       TCCATTTGGGAACAGGAGCGAGTGCCCCTTTGGATCAAGCC-ATACAAGATTCTTGTG--
      1900        1910        1920        1930        1940        1950

1960        1970        1980
         ATTACGACTGATAGTGGCATG (SEQ ID NO: 90)
         ||| || ||||||||||||||
         ATTTCGGCTGATAGTGGCATGATTGAACCAGTGGTCAATGCTG
        1960        1970        1980        1990        2000

TGTCCATCCATCAGGTG (SEQ ID NO: 91)
         2010
```

(3) Chromosomal Mapping of Human NPIK Gene by FISH

Chromosomal mapping of the human NPIK gene was carried out by FISH as described in Example 1 (3).

As a result, it was found that the locus of the human NPIK gene is in the chromosomal position 1q21.1-q21.3.

The human NPIK gene, a novel human gene, of the present invention included two cDNAs differing in the 5' region and capable of encoding 829 and 817 amino acid residues, as mentioned above. In view of this and further in view of the findings that the mRNA corresponding to this gene includes two deletable sites and there occurs polymorphism in a specific region corresponding to amino acid residues Nos. 610-618 of the GEN-428B12c1 amino acid sequence (SEQ ID NO:31), whereby a mutant protein is encoded, it is conceivable that human NPIK includes species resulting from a certain number of combinations, namely human NPIK, deletion-containing human NPIK, human NPIK mutant and/or deletion-containing human NPIK mutant.

Recently, several proteins belonging to the family including the above-mentioned PI3 and 4 kinases have protein kinase activity (Dhand, R., et al., *EMBO J.*, 13:522-533 (1994); Stack, J. H. and Emr, S. D., *J. Biol. Chem.*, 269: 31552-31562 (1994); Hartley, K. O., et al., Cell, 82:848-856 (1995)).

It was also revealed that a protein belonging to this family is involved in DNA repair (Hartley, K. O., et al., *Cell*, 82:849-856 (1995)) and is a causative gene of ataxia (Savitsky, K., et al., *Science,* 268:1749-1753 (1995)).

It can be anticipated that the human NPIK gene-encoded protein highly homologous to the family of these PI kinases is a novel enzyme phosphorylating lipids or proteins.

According to this example, the novel human NPIK gene is provided. The use of said gene makes it possible to detect the expression of said gene in various tissues and manufacture the human NPIK protein by the technology of genetic engineering and, through these, it becomes possible to study lipid- or protein-phosphorylating enzymes such as mentioned above, study DNA repairing, study or diagnose diseases in which these are involved, for example cancer, and screen out and evaluate drugs for the treatment or prevention thereof.

(4) Construction of an Expression Vector for Fusion Protein

To subclone the coding region for a human NPIK gene (GEN-428B12c2), first of all, two primers, C1 and C2, having the sequences shown below in Table 10 were formed based on the information on the DNA sequences obtained above in (1).

TABLE 10

| Primer | Nucleotide sequence |
| --- | --- |
| Primer C1 | 5'-CTCAGATCTATGGGAGATACAGTAGTGGAGC-3' (SEQ ID NO: 92) |
| Primer C2 | 5'-TCGAGATCTTCACATGATGCCGTTGGTGAG-3' (SEQ ID NO: 93) |

Both of the primers C1 and C2 have a BglII site, and primer C2 is an antisense primer.

Using these two primers, cDNA derived from human fetal brain mRNA was amplified by PCR to provide a product having a length of about 2500 bases. The amplified cDNA was precipitated from ethanol and inserted into pT7BlueT-Vector (product of Novagen) and subcloning was completed. The entire sequence was determined in the same manner as above in Examples. As a result, it was revealed that this gene had polymorphism shown above in Table 9.

The above cDNA was cleaved by BglII and subjected to agarose gel electrophoresis. The cDNA was then excised from agarose gel and collected using GENECLEAN II KIT (product of Bio 101). The cDNA was inserted into pBlueBacHis2B-Vector (product of Invitrogen) at the BglII cleavage site and subcloning was completed.

The fusion vector thus obtained had a BglII cleavage site and was an expression vector for a fusion protein of the contemplated gene product (about 91 kd) and 38 amino acids derived from pBlueBacHis2B-Vector and containing a polyhistidine region and an epitope recognizing Anti-Xpress™ antibody (product of Invitrogen).

(5) Transfection into Insect Cell Sf-9

The human NPIK gene was expressed according to the Baculovirus expression system. Baculovirus is a cyclic double-stranded insect-pathogenic virus and can produce large amounts of inclusion bodies named polyhedrins in the cells of insects. Using Bac-N-Blue™ Transfection Kit utilizing this characteristic of Baculovirus and developed by Invitrogen, the Baculovirus expression was carried out.

Stated more specifically, 4 µg of pBlueBacHis2B containing the region of the human NPIK gene and 1 µg of Bac-N-Blue™ DNA (product of Invitrogen) were co-transfected into Sf-9 cells in the presence of Insectin™ liposomes (product of Invitrogen).

Prior to co-transfection, LacZ gene was incorporated into Bac-N-Blue™ DNA, so that LacZ would be expressed only when homologous recombination took place between the Bac-N-Blue™ DNA and pBlueBacHis2B. Thus when the co-transfected Sf-9 cells were incubated on agar medium, the plaques of the virus expressing the contemplated gene were easily detected as blue plaques.

The blue plaques were excised from each agar and suspended in 400 µl of medium to disperse the virus thereon. The suspension was subjected to centrifugation to give a supernatant containing the virus. Sf-9 cells were infected with the virus again to increase the titre and to obtain a large amount of infective virus solution.

(6) Preparation of Human NPIK

The expression of the contemplated human NPIK gene was confirmed three days after infection with the virus as follows.

Sf-9 cells were collected and washed with PBS. The cells were boiled with a SDS-PAGE loading buffer for 5 minutes and SDS-PAGE was performed. According to the western blot technique using Anti-Xpress™ as an antibody, the contemplated protein was detected at the position of its presumed molecular weight. By contrast, in the case of control cells uninfected with the virus, no band corresponding to human NPIK was observed in the same test.

Stated more specifically, three days after the infection of flasks (175-cm$^2$, FALCON) of semi-confluent Sf-9 cells, the cells were harvested and washed with PBS, followed by resuspension in a buffer (20 mM Tris/HCl (pH 7.5), 1 mM EDTA and 1 mM DTT). The suspended cells were lysed by 4 time-sonications for 30 seconds at 4° C. with 30 seconds intervals. The sonicated cells were subjected to centrifugation and the supernatant was collected. The protein in the supernatant was immunoprecipitated using an Anti-Xpress™ antibody and obtained as a slurry of protein A-Sepharose beads. The slurry was boiled with a SDS-PAGE loading buffer for 5 minutes. SDS-PAGE was performed for identification and quantification of NPIK. The slurry itself was subjected to the following assaying.

(7) Confirmation of PI4 Kinase Activity

NPIK was expected to have the activity of incorporation phosphoric acid at the 4-position of the inositol ring of phosphatidylinositol (PI), namely, PI4 Kinase activity.

PI4 Kinase activity of NPIK was assayed according to the method of Takenawa, et al. (Yamakawa, A. and Takenawa, T., J. *Biol. Chem.*, 263:17555-17560 (1988)) as shown below.

First prepared was a mixture of 10 μl of a NPIK slurry (20 mM Tris/HCl (pH 7.5), 1 mM EDTA, 1 mM DTT and 50% protein A beads), 10 μl of a PI solution (prepared by drying 5 mg of a PI-containing commercial chloroform solution in a stream of nitrogen onto a glass tube wall, adding 1 ml of 20 mM Tris/HCl (pH 7.5) buffer and forming micelles by sonication), 10 μl of an applied buffer (210 mM Tris/HCl (pH 7.5), 5 mM EGTA and 100 mM $MgCl_2$) and 10 μl of distilled water. Thereto was added 10 μl of an ATP solution (5 μl of 500 μM ATP, 4.9 μl of distilled water and 0.1 μl of $\gamma$-$^{32}$P ATP (6000 Ci/mmol, product of NEN Co., Ltd.)). The reaction was started at 30° C. and continued for 2, 5, 10 and minutes. The time 10 minutes was set as incubation time because a straight-line increase was observed around 10 minutes in incorporation of phosphoric acid into PI in the assaying process described below.

After completion of the reaction, PI was fractionated by the solvent extraction method and finally re-suspended in chloroform. The suspension was developed by thin layer chromatography (TLC) and the radioactivity of the reaction product at the PI4P-position was assayed using an analyzer (trade name: Bio-Image; product of Fuji Photo Film Co., Ltd.).

FIG. 1 shows the results. FIG. 1 is an analytical diagram of the results of assaying the radioactivity based on TLC as mentioned above. The right lane (2) is the fraction of Sf-9 cell cytoplasm infected with the NPIK-containing virus, whereas the left lane (1) is the fraction of uninfected Sf-9 cell cytoplasm.

Also, predetermined amounts of Triton X-100™ and adenosine were added to the above reaction system to check how such addition would affect the PI4 Kinase activity. The PI4 Kinase activity was assayed in the same manner as above.

Figure 2:
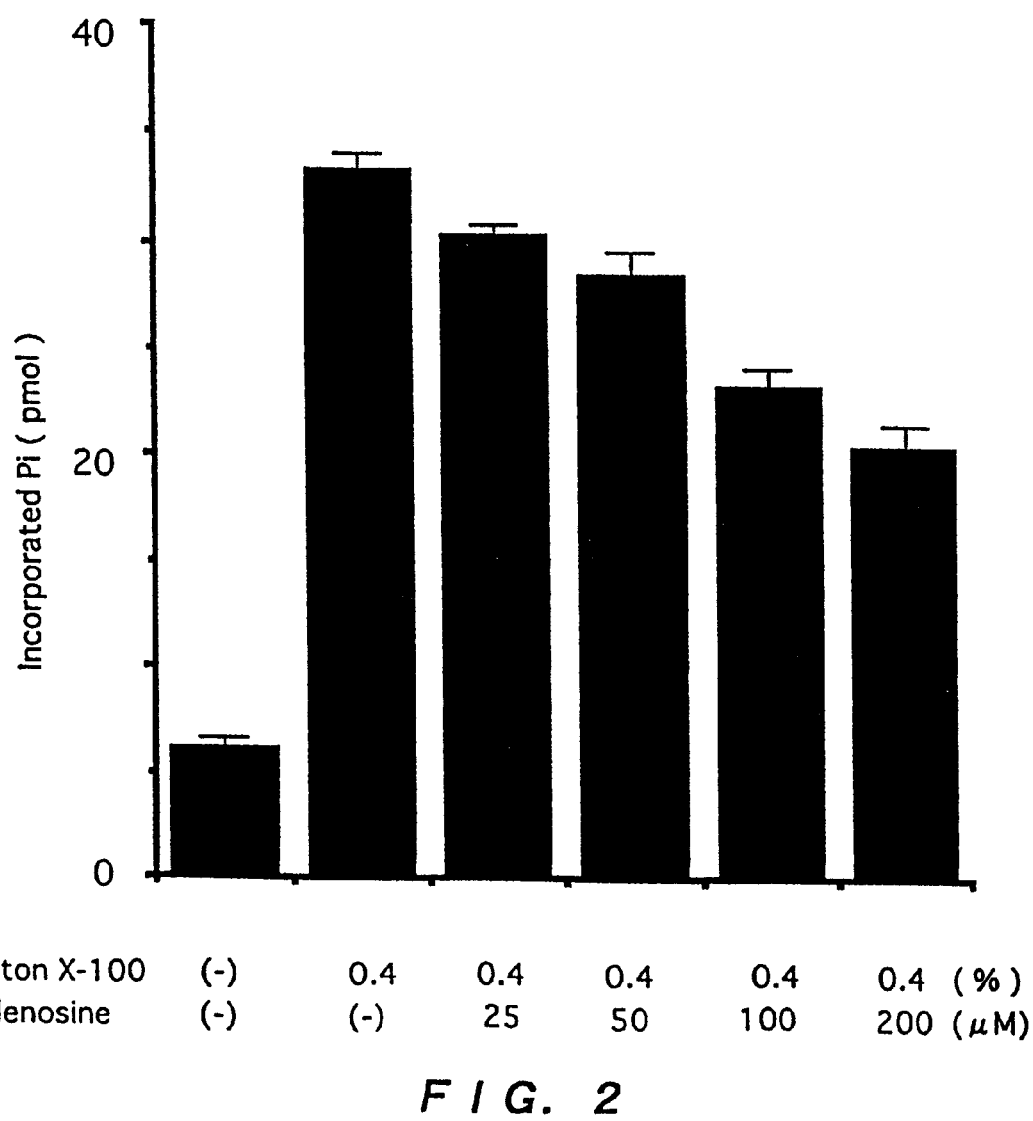
FIG. 2 shows the effect of Triton X-100® and adenosine on NPIK activity.

FIG. 2 shows the results. The results confirmed that NPIK had a typical PI4 Kinaze activity accelerated by Triton X-100™ and inhibited by adenosine.

Example 10

Nel-Related Protein Type 1 (NRP1) Gene and
Nel-Related Protein Type 2 (NRP2) Gene (1) Cloning and DNA Sequencing of NRP1 Gene and NRP2 Gene EGF-like repeats have been found in many membrane proteins and in proteins related to growth regulation and differentiation. This motif seems to be involved in protein-protein interactions.

Recently, a gene encoding nel, a novel peptide containing five EGF-like repeats, was cloned from a chick embryonic cDNA library (Matsuhashi, S., et al., *Dev. Dynamics*, 203: 212-222 (1995)). This product is considered to be a transmembrane molecule with its EGF-like repeats in the extracellular domain. A 4.5 kb transcript (nel mRNA) is expressed in various tissues at the embryonic stage and exclusively in brain and retina after hatching.

Following the procedure of Example 1 (1), cDNA clones were randomly selected from a human fetal brain cDNA library and subjected to sequence analysis, followed by database searching. As a result, two cDNA clones with significantly high homology to the above-mentioned nel were found and named GEN-073E07 and GEN-093E05, respectively.

Since both clones were lacking in the 5' portion, 5' RACE was performed in the same manner as in Example 2 (2) to obtain the entire coding regions.

As for the primers for 5' RACE, primers having an arbitrary sequence obtained from the cDNA sequences of the above clones were synthesized while the anchor primer attached to a commercial kit was used as such.

5' RACE clones obtained from the PCR were sequenced and the sequences seemingly covering the entire coding regions of both genes were obtained. These genes were respectively named nel-related protein type 1 (NRP1) gene and nel-related protein type 2 (NRP2) gene.

The NRP1 gene contains an open reading frame of 2,430 nucleotides, as shown under SEQ ID NO:35, the amino acid sequence deduced therefrom comprises 810 amino acid residues, as shown under SEQ ID NO:34, and the nucleotide sequence of the entire cDNA clone of said NRP1 gene comprises 2,977 nucleotides, as shown under SEQ ID NO:36.

On the other hand, the NRP2 gene contains an open reading frame of 2,448 nucleotides, as shown under SEQ ID NO:38, the amino acid sequence deduced therefrom comprises 816 amino acid residues, as shown under SEQ ID NO:37, and the nucleotide sequence of the entire cDNA clone of said NRP2 gene comprises 3,198 nucleotides, as shown under SEQ ID NO:39.

Furthermore, the coding regions were amplified by RT-PCR to exclude the possibility that either of the sequences obtained was a chimeric cDNA.

The deduced NRP1 and NRP2 gene products both showed highly hydrophobic N termini capable of functioning as signal peptides for membrane insertion. As compared with chick embryonic nel, they both appeared to have no hydrophobic transmembrane domain. Comparison among NRP1, NRP2 and nel with respect to the deduced peptide sequences revealed that NRP2 has 80% homology on the amino acid level and is more closely related to nel than NRP1 having 50% homology. The cysteine residues in cysteine-rich domains and EGF-like repeats were found completely conserved.

The most remarkable difference between the NRPs and the chick protein was that the human homologs lack the putative transmembrane domain of nel. However, even in this lacking region, the nucleotide sequences of NRPs were very similar to that of nel. Furthermore, the two NRPs each possessed six EGF-like repeats, whereas nel has only five.

Other unique motifs of nel as reported by Matsuhashi et al. (Matsuhashi, S., et al., *Dev. Dynamics*, 203:212-222 (1995)) were also found in the NRPs at equivalent positions. Since as mentioned above, it was shown that the two deduced NRP peptides are not transmembrane proteins, the NRPs might be secretory proteins or proteins anchored to membranes as a result of posttranslational modification.

The present inventors speculate that NRPs might function as ligands by stimulating other molecules such as EGF receptors. The present inventors further found that an extra EGF-like repeat could be encoded in nel upon frame shifting of the membrane domain region of nel.

When paralleled and compared with NRP2 and nel, the frame-shifted amino acid sequence showed similarities over the whole range of NRP2 and of nel, suggesting that NRP2 might be a human counterpart of nel. In contrast, NRP1 is considered to be not a human counterpart of nel but a homologous gene.

(2) Northern Blot Analysis

Northern blot analysis was carried out as described in Example 1 (2). Thus, the entire sequences of both clones cDNAs were amplified by PCR, the PCR products were purified and labeled with [$^{32}$P]-dCTP (random-primed DNA labeling kit, Boehringer Mannheim) and human normal tissues were examined for NRP mRNA expression using an MTN blot with the labeled products as two probes.

Sixteen adult tissues and four human fetal tissues were examined for the expression pattern of two NRPs.

As a result of the Northern blot analysis, it was found that a 3.5 kb transcript of NRP1 was weakly expressed in fetal and adult brain and kidney. A 3.6 kb transcript of NRP2 was strongly expressed in adult and fetal brain alone, with weak expression thereof in fetal kidney as well.

This suggests that NRPs might play a brain-specific role, for example as signal molecules for growth regulation. In addition, these genes might have a particular function in kidney.

(3) Chromosomal Mapping of NRP1 Gene and NRP2 Gene by FISH

Chromosomal mapping of the NRP1 gene and NRP2 gene was performed by FISH as described in Example 1 (3).

As a result, it was revealed that the chromosomal locus of the NRP1 gene is localized to 11p15.1-p15.2 and the chromosomal locus of the NRP2 gene to 12q13.11-q13.12.

According to the present invention, the novel human NRP1 gene and NRP2 gene are provided and the use of said genes makes it possible to detect the expression of said genes in various tissues and produce the human NRP1 and NRP2 proteins by the technology of genetic engineering. They can further be used in the study of the brain neurotransmission system, diagnosis of various diseases related to neurotransmission in the brain, and the screening and evaluation of drugs for the treatment and prevention of such diseases. Furthermore, the possibility is suggested that these EGF domain-containing NRPs act as growth factors in brain, hence they may be useful in the diagnosis and treatment of various kinds of intracerebral tumor and effective in nerve regeneration in cases of degenerative nervous diseases.

Example 11

GSPT1-Related Protein (GSPT1-TK) Gene (1) GSPT1-TK Gene Cloning and DNA Sequencing The human GSPT1 gene is one of the human homologous genes of the yeast GST1 gene that encodes the GTP-binding protein essential for the G1 to S phase transition in the cell cycle. The yeast GST1 gene, first identified as a protein capable of complementing a temperature-sensitive gst1 (G1-to-S transition) mutant of *Saccharomyces cerevisiae*, was isolated from a yeast genomic library (Kikuchi, Y., Shimatake, H. and Kikuchi, A., *EMBO J.*, 7:1175-1182 (1988)) and encoded a protein with a target site of cAMP-dependent protein kinases and a GTPase domain.

The human GSPT1 gene was isolated from a KB cell cDNA library by hybridization using the yeast GST1 gene as a probe (Hoshino, S., Miyazawa, H., Enomoto, T., Hanaoka, F., Kikuchi, Y., Kikuchi, A. and Ui, M., *EMBO J.*, 8:3807-3814 (1989)). The deduced protein of said GSPT1 gene, like yeast GST1, has a GTP-binding domain and a GTPase activity center, and plays an important role in cell proliferation.

Furthermore, a breakpoint for chromosome rearrangement has been observed in the GSPT1 gene located in the chromosomal locus 16p13.3 in patients with acute nonlymphocytic leukemia (ANLL) (Ozawa, K., Murakami, Y., Eki, T., Yokoyama, K., Soeda, E., Hoshino, S., Ui, M. and Hanaoka, F., *Somatic Cell and Molecular Genet.*, 18:189-194 (1992)).

cDNA clones were randomly selected from a human fetal brain cDNA library and subjected to sequence analysis as described in Example 1 (1) and database searching was performed and, as a result, a clone having a 0.3 kb cDNA sequence highly homologous to the above-mentioned GSPT1 gene was found and named GEN-077A09. The GEN-077A09 clone seemed to be lacking in the 5' region, so that 5' RACE was carried out in the same manner as in Example 2 (2) to obtain the entire coding region.

The primers used for the 5' RACE were P1 and P2 primers respectively having the nucleotide sequences shown in Table 11 as designed based on the known cDNA sequence of the above-mentioned cDNA, and the anchor primer used was the one attached to the commercial kit. Thirty-five cycles of PCR were performed under the following conditions: 94° C. for 45 seconds, 58° C. for 45 seconds and 72° C. for 2 minutes. Finally, elongation reaction was carried out at 72° C. for 7 minutes.

TABLE 11

| Primer | Nucleotide sequence |
|---|---|
| P1 primer | 5'-GATTTGTGCTCAATAATCACTATCTGAA-3' (SEQ ID NO: 94) |
| P2 primer | 5'-GGTTACTAGGATCACAAAGTATGAATTCTGGAA-3' (SEQ ID NO: 95) |

Several of the 5' RACE clones obtained from the above PCR were sequenced and the base sequence of that cDNA clone showing overlapping between the 5' RACE clones and the GEN-077A09 clone was determined to thereby reveal the sequence regarded as covering the entire coding region. This was named GSPT1-related protein "GSPT1-TK gene".

The GSPT1-TK gene was found to contain an open reading frame of 1,497 nucleotides, as shown under SEQ ID NO:41. The amino acid sequence deduced therefrom contained 499 amino acid residues, as shown under SEQ ID NO:40.

The nucleotide sequence of the whole cDNA clone of the GSPT1-TK gene was found to comprise 2,057 nucleotides, as shown under SEQ ID NO:42, and the molecular weight was calculated at 55,740 daltons.

The first methionine code (ATG) in the open reading frame had no in-frame termination codon but this ATG was surrounded by a sequence similar to the Kozak consensus sequence for translational initiation. Therefore, it was concluded that this ATG triplet occurring in positions 144-146 of the relevant sequence is the initiation codon.

Furthermore, a polyadenylation signal, AATAAA (within SEQ ID NO:42), was observed 13 nucleotides upstream from the polyadenylation site.

Human GSPT1-TK contains a glutamic acid rich region near the N terminus, and 18 of 20 glutamic acid residues occurring in this region of human GSPT1-TK are conserved and align perfectly with those of the human GSPT1 protein. Several regions (G1, G2, G3, G4 and G5) of GTP-binding proteins that are responsible for guanine nucleotide binding and hydrolysis were found conserved in the GSPT1-TK protein just as in the human GSPT1 protein.

Thus, the DNA sequence of human GSPT1-TK was found 89.4% identical, and the amino acid sequence deduced therefrom 92.4% identical, with the corresponding sequence of human GSPT1 which supposedly plays an important role in the G1 to S phase transition in the cell cycle. Said amino acid sequence showed 50.8% identity with that of yeast GST1.

(2) Northern Blot Analysis

Northern blot analysis was carried out as described in Example 1 (2). Thus, the GEN-077A09 cDNA clone was amplified by PCR, the PCR product was purified and labeled with [$^{32}$P]-dCTP (random-primed DNA labeling kit, Boehringer Mannheim), and normal human tissues were examined for the expression of GSPT1-TK mRNA therein using an MTN blot with the labeled product as a probe.

As a result of the Northern blot analysis, a 2.7 kb major transcript was detected in various tissues. The level of human GSPT1-TK expression seemed highest in brain and in testis.
(3) Chromosome Mapping of GSPT1-TK Gene by FISH Chromosome mapping of the GSPT1-TK gene was performed by FISH as described in Example 1 (3).

As a result, it was found that the GSPT1-TK gene is localized at the chromosomal locus 19p13.3. In this chromosomal localization site, reciprocal location has been observed very frequently in cases of acute lymphocytic leukemia (ALL) and acute myeloid leukemia (AML). In addition, it is reported that acute non-lymphocytic leukemia (ANLL) is associated with re-arrangements involving the human GSPT1 region (Ozawa, K., Murakami, Y., Eki, T., Yokoyama, K., Soeda, E., Hoshino, S., Ui, M. and Hanaoka, F., *Somatic Cell and Molecular Genet.*, 18:189-194 (1992)).

In view of the above, it is suggested that this gene is the best candidate gene associated with ALL and AML.

In accordance with the present invention, the novel human GSPT1-TK gene is provided and the use of said gene makes it possible to detect the expression of said gene in various tissues and produce the human GSPT1-TK protein by the technology of genetic engineering. These can be used in the studies of cell proliferation, as mentioned above, and further make it possible to diagnose various diseases associated with the chromosomal locus of this gene, for example acute myelocytic leukemia. This is because translocation of this gene may result in decomposition of the GSPT1-TK gene and further some or other fused protein expressed upon said translocation may cause such diseases.

Furthermore, it is expected that diagnosis and treatment of said diseases can be made possible by producing antibodies to such fused protein, revealing the intracellular localization of said protein and examining its expression specific to said diseases. Therefore, it is also expected that the use of the gene of the present invention makes it possible to screen out and evaluate drugs for the treatment and prevention of said diseases.

What is claimed:

1. An isolated antibody which binds to a polypeptide comprising the amino acid sequence of SEQ ID No. 37.

2. The isolated antibody according to claim 1, wherein the antibody is a polyclonal antibody or a monoclonal antibody.

* * * * *